United States Patent [19]

Wu et al.

[11] Patent Number: 5,223,525

[45] Date of Patent: Jun. 29, 1993

[54] PESTICIDAL 1-ARYLIMIDAZOLES

[75] Inventors: Tai-Teh Wu, Chapel Hill; David N. Sinodis, Cary; Philip R. Timmons, Durham; Gail S. Powell; David T. Chou, both of Raleigh; Peter W. Newsome, Chapel Hill; Lee S. Hall, Raleigh, all of N.C.

[73] Assignee: Rhone-Poulenc AG Company, Research Triangle Park, N.C.

[21] Appl. No.: 606,518

[22] Filed: Oct. 31, 1990

Related U.S. Application Data

[63] Continuation-in-part of Ser. No. 348,682, May 5, 1989, abandoned.

[51] Int. Cl.$^5$ ................ C07D 233/84; C07D 233/68; A01N 43/50
[52] U.S. Cl. .................................... 514/398; 514/399; 514/400; 548/316.4; 548/317.5; 548/318.1; 548/318.5; 548/319.5; 548/320.1; 548/320.5; 548/321.1; 548/321.5; 548/322.5; 548/323.1; 548/324.5; 548/325.1; 548/325.5; 548/327.1; 548/327.5; 548/328.1; 548/329.1; 548/331.5; 548/332.1; 548/332.5; 548/333.5; 548/334.5; 548/337.1; 548/343.1
[58] Field of Search ............... 548/337, 315, 319, 301, 548/321, 339, 342, 343, 316.4, 317.5, 318.1, 318.5, 319.5, 320.1, 320.5, 321.1, 321.5, 322.5, 323.1, 324.5, 325.1, 325.5, 327.1, 327.5, 328.1, 329.1, 331.5, 332.1, 332.5, 333.5, 334.5, 337.1, 343.1; 514/398, 399, 400, 386, 392

[56] References Cited

U.S. PATENT DOCUMENTS 4,728,653 3/1988 Campbell et al. ................ 514/312
4,755,213 7/1988 Schmierer et al. ................ 71/92
4,943,585 7/1990 Buerstinghaus et al. ............ 514/384

OTHER PUBLICATIONS

Chemical Abstracts, vol. 80(15), 82809j, 1974.

*Primary Examiner*—Mary C. Lee
*Assistant Examiner*—Lenora Miltenberger
*Attorney, Agent, or Firm*—James G. Passé

[57] ABSTRACT

The invention describes novel 1-arylimidazoles of formula (I)

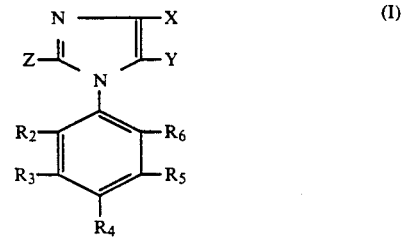

wherein typically preferred substituents are:

X is $S(O)_nR_1$, in which $R_1$ is an alkyl group, preferably a methyl group, which is fully substituted by halogen atoms, and n is 0, 1 and 2;

Y is hydrogen, halogen, alkyl, alkoxy, alkoxyalkylideneimino, alkylsulfenyl, alkylsulfinyl or alkylsulfonyl;

Z is hydrogen, halogen, alkyl, preferably methyl; and $R_2$, $R_3$, $R_4$, $R_5$ and $R_6$ are individually hydrogen, halogen or an unsubstituted or halo-substituted alkyl, alkoxy, alkylsulfenyl, alkylsulfinyl or alkylsulfonyl.

The invention further describes intermediates and processes to make the compounds, compositions of the compounds, and methods of use of the compounds for the control of arthropods (especially mites, aphids or insects), nematodes, helminths, or protozoa.

33 Claims, No Drawings

PESTICIDAL 1-ARYLIMIDAZOLES

This is a continuation-in-part application of copending application Ser. No. 07/348,682, filed May 5, 1989, now abandoned, incorporated herein by reference.

BACKGROUND OF THE INVENTION

1. Field of the Invention

The present invention relates to new 1-arylimidazoles and intermediates and processes to make the compounds. The invention further pertains to compositions of said compounds and methods, using said compounds, for the control of arthropod, nematode, helminth or protozoan pests. In particular, it pertains to the application of compounds or compositions thereof in agriculture and methods of use, particularly as pesticides, for controlling arthropods, especially mites or foliar or soil insects, without causing injury to crop plants.

2. Description of the Related Art

Various substituted imidazole compounds are known to exhibit a number of different types of pesticidal activity, including activity as herbicides, plant growth regulators, fungicides, nematicides, insecticides and biocides. Included among these are the following: European Patent Application No. EP 270061A discloses as insecticides 1-arylimidazoles that are unsubstituted in the 2 and 4 positions of the imidazole ring, which additionally has a second phenyl substituent in the 5 position. U.S. Pat. No. 4,755,213 discloses as plant growth regulators 1-arylimidazoles which are likewise unsubstituted in the 2 and 4 positions of the imidazole ring and further substituted by a carboxamide (aminocarbonyl) group in the 5 position. European Patent Application Nos. EP 277384A and EP 289066A disclose as herbicides 1-arylimidazoles which are only substituted in the 2 and 5 positions and again unsubstituted in the 4 position of the imidazole ring. Other 1-substituted imidazoles are described as insecticides in European Patent Application No. 289919A, in which case the 1-substituent is aralkyl or aralkoxy (i.e., an alkyl or alkoxy bridging group between the imidazole and aryl rings). European Patent Application No. 283173A discloses as insecticides, etc. 2-arylimidazoles in which the aryl ring is attached to the imidazole ring at a carbon atom (2-position) rather than a nitrogen atom and the 1-position nitrogen atom is substituted by hydrogen or an optionally substituted alkyl group. Australian Patent Application No. 8812-883A discloses as fungicides, insecticides, nematicides, etc., imidazole compounds which may be substituted at the 4 or 5 or both 4 and 5 positions of the imidazole ring (i.e., attachment to carbon rather than nitrogen) by an optionally substituted phenyl ring and are substituted on the 1-position nitrogen atom by a hydrogen atom or a sulfonyl group.

SUMMARY OF THE INVENTION

The present invention pertains to new and novel 1-arylimidazole compounds which exhibit outstanding pesticidal properties, especially as insecticides or miticides or both.

The compounds, including their stereo isomers, e.g. diastereomers and optical isomers, have the following general formula (I)

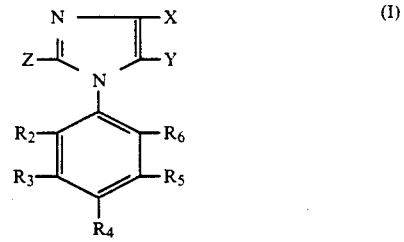

wherein:

X is a group selected from haloalkyl or haloalkoxy or an unsubstituted or halo-substituted group selected from alkylsulfenyl, alkylsulfinyl or alkylsulfonyl, wherein the defined alkyl and alkoxy moieties of each group are a linear or branched chain, containing one to four carbon atoms, and the halo-substitution of each group consists of one or more halogen atoms, which are the same or different, up to full substitution of the alkyl or alkoxy moiety;

Y and Z are each individually selected from: a hydrogen or a halogen atom; a group selected from nitro, cyano, hydroxyl (and acceptable salts thereof), sulfhydryl (and acceptable salts thereof), formyl, hydroxycarbonyl (and acceptable salts thereof), alkoxycarbonyl, aminocarbonyl, alkylaminocarbonyl, dialkylaminocarbonyl, amino, alkylamino, dialkylamino, a trialkylammonium salt, cyanoalkyl, alkoxycarbonylamino, arylcarbonylamino, alkylaminocarbonylamino, dialkylaminocarbonylamino, aminosulfonyl, alkylaminosulfonyl, dialkylaminosulfonyl, or alkoxyalkylideneimino, in which the defined alkyl and alkoxy moieties of each group are a linear or branched chain containing one to four carbon atoms; a linear or branched chain alkenyl or alkynyl group containing two to four carbon atoms; or a group selected from an unsubstituted or halo-substituted alkyl, alkoxy, alkylcarbonyl, alkylcarbonylamino, alkylsulfenyl, alkylsulfinyl or alkylsulfonyl, in which the defined alkyl and alkoxy moieties of each group are a linear or branched chain containing one to four carbon atoms and the halo-substitution consists of one or more halogen atoms, which are the same or different, up to full substitution of the alkyl or alkoxy moiety; and only one of Y and Z is a sulfur containing group; and $R_2$, $R_3$, $R_4$, $R_5$ and $R_6$ are individually selected from: a hydrogen or a halogen atom; a group selected from nitro, cyano, amino, alkylamino or dialkylamino, in which the alkyl moiety of each group is a linear or branched chain containing one to four carbon atoms; a linear or branched chain alkenyl or alkynyl group containing two to four carbon atoms, which may be substituted by one or more halogen atoms, which are the same or different, up to full substitution; or a group selected from an unsubstituted or halo-substituted alkyl, alkoxy, alkylsulfenyl, alkylsulfinyl or alkylsulfonyl, in which the defined alkyl and alkoxy moieties of each group are a linear or branched chain containing one to four carbon atoms and the halo-substitution consists of one or more halogen atoms, which are the same or different, up to full substitution of the alkyl or alkoxy moiety.

According to a preferred feature of the invention, the pesticidal compounds are selected from amongst the compounds of formula (I), wherein X is S(O)$_n$R$_1$, having the formula (IIa)

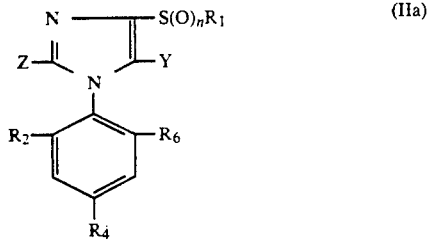

wherein:
Y and Z are individually selected from a hydrogen or halogen atom; a group selected from nitro, cyano, hydroxyl, sulfhydryl, amino, alkylamino or dialkylamino, in which the defined alkyl moiety of each group is a linear or branched chain containing one to four carbon atoms; or a group selected from an unsubstituted or fully halo-substituted alkyl, alkoxy, alkylcarbonyl, alkylcarbonylamino, alkylsulfenyl, alkylsulfinyl or alkylsulfonyl, in which the defined alkyl and alkoxy moieties of each group are a linear or branched chain, containing one to four carbon atoms, and the full halo-substitution of the alkyl or alkoxy moiety is by the same or different halogen atoms; and only one of Y and Z is a sulfur containing group;

R$_1$ is a linear or branched alkyl group of one to four carbon atoms which are unsubstituted or halo-substituted by one or more halogen atoms, which are the same or different;

R$_2$ is a hydrogen or a halogen atom or an alkyl, alkoxy, methylsulfenyl, methylsulfinyl or methylsulfonyl group;

R$_4$ is selected from a halogen atom or a group selected from trifluoromethyl, trifluoromethoxy, difluoromethoxy, trifluoromethylsulfenyl, trifluoromethylsulfinyl, trifluoromethylsulfonyl, or a linear or branched chain alkyl group containing one to four carbon atoms;

R$_6$ is a halogen atom (i.e., fluorine, chlorine or bromine); and n is 0, 1 or 2.

Amongst the compounds of formula (IIa) which are preferred are those compounds having a formula (IIa-1) wherein:
Y is a hydrogen atom, a halogen atom, amino, hydroxy, alkoxy of one to four carbon atoms, methylsulfenyl, methylsulfinyl or methylsulfonyl;

Z is a hydrogen atom, a halogen atom, or a linear or branched alkyl group of one to four carbon atoms which is optionally fully substituted by halogen atoms which are the same or different;

R$_1$ is a methyl group fully substituted by halogen atoms which are the same or different;

R$_2$ is a hydrogen atom, a halogen atom or methylsulfenyl;

R$_4$ is a halogen atom, trifluoromethyl or trifluoromethoxy; and

R$_6$ is a fluorine, chlorine or bromine atom; and n is 0, 1 or 2.

Even more specifically preferred compounds of formula (IIa-1) are those compounds having a formula (IIa-2) wherein:

Y is a hydrogen atom, a chlorine atom, a bromine atom, methylsulfenyl, methylsulfinyl or methoxy;

Z is a hydrogen atom, a chlorine atom, a bromine atom or methyl;

R$_1$ is trifluoromethyl, dichlorofluoromethyl or chlorodifluoromethyl;

R$_2$ is a hydrogen atom, a chlorine atom, a bromine atom or methylsulfenyl;

R$_4$ is a chlorine atom, a bromine atom, trifluoromethyl or trifluoromethoxy; and R$_6$ is a chlorine or bromine atom; and n is 0, 1 or 2.

The following are some of the representative preferred compounds of formula (IIa) (described subsequently in EXAMPLES 1-267) in the categories identified below:

High broad spectrum insecticidal activity

Compounds of EXAMPLES 4, 9, 20, 23, 25, 28, 29, 31, 32, 33, 34, 35, 36, 37, 38, 42, 44, 45, 60, 61, 70, 144, and 146.
Typically wherein:
Y is H;
Z is Cl or Br (or optionally may be H or CH$_3$);
R$_1$ is CF$_3$, CCl$_2$F or CClF$_2$;
n is 0, 1 or 2;
R$_2$ is Cl (or optionally may be SCH$_3$);
R$_3$ and R$_5$ are H; and
R$_4$ is CF$_3$ (or optionally may be OCF$_3$).

Good aphicidal activity

Compounds of EXAMPLES 20, 21, 41, 42, 44, 48, 122, 131, 132, 144, 163, 173, 174, 175, 196, 197, 253, 254, and 255.
Typically wherein:
Y and Z are H (or optionally may be Cl);
R$_1$ is CF$_3$, CCl$_2$F or CClF$_2$;
n is 0, 1 or 2;
R$_2$ and R$_6$ are Cl;
R$_3$ and R$_5$ are H; and
R$_4$ is CF$_3$ (or optionally may be OCF$_3$).

High aphicidal plus broad spectrum insecticidal activity

Compounds of EXAMPLES 10, 59, 60, 61, 68, and 69.
Typically wherein:
Y is H;
Z is CH$_3$;
R$_1$ is CF$_3$, CCl$_2$F or CClF$_2$;
n is 0, 1 or 2;
R$_2$ and R$_6$ are Cl;
R$_3$ and R$_5$ are H; and
R$_4$ is CF$_3$.

Good to high miticidal activity

Compounds of EXAMPLES 9, 18, 60, 61, 70, 91, 92, 95, 96, 104, 106, 109, 187, 188, 189, 190, 191, 194, 196, 197, 199, 200, 201, 202, 212, 214, 216, 217, 218, 220, 221, 224, and 225.
Typically wherein:
Y and Z are H (or optionally Z may be Cl, Br or CH$_3$ and Y optionally may be Br);
R$_1$ is CF$_3$, CCl$_2$F, CHClF or CClF$_2$;
n is 0, 1 or 2;
R$_2$ and R$_6$ are Cl (or optionally R$_2$ may be SCH$_3$);
R$_3$ and R$_5$ are H; and
R$_4$ is Cl or Br (or optionally may be CF$_3$).

Good to high soil insecticide (corn rootworm) activity

Compounds of EXAMPLES 3, 4, 5, 6, 8, 9, 12, 16, 23, 25, 26, 28, 31, 33, 34, 35, 36, 37 and 38.
Typically wherein:
Y is H, Cl, or Br (or optionally may be $SCH_3$ or $N=CHOC_2H_5$);
Z is H, Cl or Br;
$R_1$ is $CF_3$, $CCl_2F$ or $CClF_2$;
n is 0, 1 or 2;
$R_2$ and $R_6$ are Cl (or optionally $R_2$ is $SCH_3$);
$R_3$ and $R_5$ are H; and
$R_4$ is $CF_3$.
Compound of EXAMPLE 178.
Typically wherein:
Y is $SCH_3$;
Z is Cl;
$R_1$ is $CClF_2$;
$R_2$ and $R_6$ are Cl;
$R_4$ is $CF_3$; and
n is 0.

According to still a further preferred feature of the invention, there are pesticidal compounds which are highly active, particularly as insecticides and miticides, and have good safety properties during handling, use or application. Of particular interests are highly active pesticidal compounds which are safe to man or his environment. These preferred compounds are selected from amongst the compounds of formula (I), wherein X is $S(O)_nR_1$, having a formula (IIb)

$$\underset{R_4}{\underset{R_2 \diagup \!\!\!\!\! - \!\!\!\!\! \diagdown R_6}{Z \diagup \!\!\!\!\! \underset{N}{\overset{N}{\diagdown}} \!\!\!\!\! \diagdown Y}} \overset{S(O)_nR_1}{\underset{Y}{\diagup}} \qquad (IIb)$$

wherein:
Y is hydrogen, halogen, alkyl, alkoxy, alkoxyalkylideneimino, alkylsulfenyl, alkylsulfinyl or alkylsulfonyl, in which the alkyl and alkoxy moieties of each group are a linear or branched chain containing one to four carbon atoms;
Z is hydrogen or alkyl which is a linear or branched chain of one to four carbon atoms;
$R_1$ is a linear or branched chain alkyl group of one to four carbon atoms which are unsubstituted or halo-substituted by one or more halogen atoms, which are the same or different, up to full substitution of the alkyl group;
$R_2$ is halogen or alkylsulfenyl;
$R_6$ is halogen;
$R_4$ is hydrogen, halogen, haloalkyl or haloalkoxy in which the alkyl and alkoxy moieties of each group are a linear or branched chain containing one to four carbon atoms and the halo-substitution is by one or more halogen atoms, which are the same or different up to full substitution of the alkyl or alkoxy moiety; and
n is 0, 1 or 2.

In particular related to compounds of formula (IIb), there are certain specific substituent groups which appear to be beneficial in providing the safety characteristics described above. These groups include, for example:
alkyl, especially Y is methyl or ethyl;
alkoxy, especially Y is methoxy or ethoxy;
alkoxyalkylideneimino, especially Y is methoxy(or ethoxy)-methylideneimino;
alkylsulfenyl, especially Y is methylsulfenyl; and
halogen being fluorine, especially $R_4$ is fluorine.

Amongst compounds of formula (IIb) which are further preferred, including for example as miticides, are those compounds having a formula (IIb-1) wherein:
Y is H, F, Cl, Br, I, $CH_3$, $C_2H_5$, $OCH_3$, $OC_2H_5$, $N=CHOCH_3$, $N=CHOC_2H_5$, $SCH_3$, $SOCH_3$ or $SO_2CH_3$;
Z is H, $CH_3$ or $C_2H_5$;
$R_1$ is $CF_3$, $CCl_2F$, $CClF_2$, $CHCl_2$, $CHClF$ or $CHF_2$;
$R_2$ is F, Cl, Br, or $SCH_3$;
$R_6$ is F, Cl or Br;
$R_4$ is H or F; or $R_4$ is Cl, Br, I, $CF_3$ or $OCF_3$ when Y is $CH_3$, $C_2H_5$, $OCH_3$, $OC_2H_5$, $N=CHOCH_3$, $N=CHOC_2H_5$, $SCH_3$, $SOCH_3$ or $SO_2CH_3$; and
n is 0, 1 or 2.

The following are some of the representative preferred compounds of formula (IIb) (described subsequently in EXAMPLES 165-267) in the categories identified below:

High miticidal activity

Compounds of EXAMPLES 192, 203, 211, 213, 222, 223, 226, 228, 230, 231, 233, 235, 240, 244, 250, and 251.
Typically wherein:
Y is $SCH_3$, $N=CHOC_2H_5$, Cl or Br;
Z is H;
$R_1$ is $CF_3$, $CCl_2F$ or $CClF_2$;
$R_2$ and $R_6$ are Cl or Br;
$R_4$ is F; or $R_4$ is Cl or Br when Y is $SCH_3$ or $N=CHOC_2H_5$; and
n is 0.

High aphicidal activity

Compound of EXAMPLE 176.
Typically wherein:
Y is $SCH_3$;
Z is $CH_3$;
$R_1$ is $CCl_2F$;
$R_2$ and $R_6$ are Cl;
$R_4$ is $CF_3$; and
n is 0.

It is an object of the present invention to provide new compounds of the imidazole family together with processes for their preparation and intermediates thereto.

A second object of the present invention is to provide, for example, agronomically or medicinally acceptable compositions.

A third object of the present invention is to provide highly active compounds for use against: arthropods, especially mites, aphids or insects; plant nematodes; or helminth or protozoan pests. The compounds are thus advantageously used, for example, in agricultural or horticultural crops, forestry, veterinary medicine or livestock husbandry, or in public health.

A fourth object of the present invention is to provide compounds with broad spectrum activity as insecticides, miticides, aphicides or nematicides, by either soil, foliar application or seed treatment, including via systemic action.

A fifth object of the present invention is to provide compounds having high arthropod toxicity, for example: to insects in the Coleoptera order, particularly Diabrotica spp. (corn rootworm), in the Lepidoptera order, particularly Agrotis and Amathes spp. (cutworms), or in the Diptera order, particularly Delia spp. (root maggots) or *Musca domestica* (housefly); to mites in the subclass Acari, particularly *Tetranychus urticae* (twospotted spider mite), *Polyphagotarsonemus latus* (broad mite), *Phyllocoptruta oleivora* (citrus rust mite), or *Panonychus ulmi* (European red mite); or to aphids in the super family Aphidoidea, particularly *Aphis nasturtii* (buckthorn aphid).

An additional object of the present invention is to provide pesticidal compounds which are highly active, especially as insecticides or miticides, and are safe to man or his environment during handling, use, or application.

These and other objects of the invention shall become readily apparent from the detailed description of the present invention.

DESCRIPTION OF THE PREFERRED EMBODIMENTS

METHODS OR PROCESSES OF SYNTHESIS

The compounds of general formula (I) can be prepared by the application or adaptation of known methods (i.e. methods heretofore used or described in the chemical literature): generally imidazole ring formation followed wherein necessary by changing substituents. It is to be also understood that, in the description of the following process methods, the sequences for the introduction of the various groups on the imidazole ring may be performed in a different order and that suitable protecting groups may be required as will be apparent to those skilled in the art. Also compounds of general formula (I) may be converted by known methods into other compounds of general formula (I).

In the following description of process methods when symbols appearing in formulae are not specifically defined, it is to be understood that they are "as herein before defined" in accordance with the first definition of each symbol in this specification. The term "protection" shall include conversion to a suitable non-reactive group which may be reconverted when desired, as well as the addition of groups which render the functionality non-reactive. Within the process definitions, unless otherwise stated, amino refers to the unsubstituted amino group.

The invention embraces particular intermediate compounds, useful to make certain of the herein contemplated compounds. Such preferred intermediate compounds, prepared as described herein, are defined in the following methods. In particular, intermediates that are more preferred have $R_2$ to $R_6$ as defined by formula (II) of the invention or more specifically preferred $R_2$, $R_4$ and $R_6$ definitions therein.

The following synthetic Methods I to VI generally describe alternative cyclization procedures beginning with appropriately substituted N-phenylimino compounds which are cyclized by means of a basic reagent to useful and novel intermediate N-phenylimidazole compounds. This reaction (including subsequent initial derivatization of the Z and Y substituents) can be generally represented by the reaction of a compound of formula (III) with a basic agent to give a compound of formula (IV) as follows:

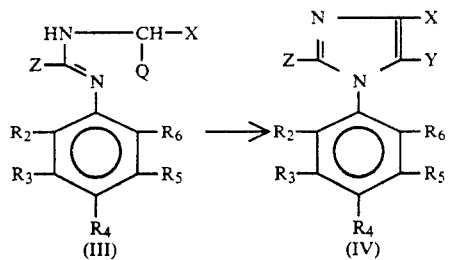

wherein for formula (III):
 $R_2$, $R_3$, $R_4$, $R_5$ and $R_6$ are as defined in formula (I);
 X is hydrogen or haloalkyl, particularly trifluoromethyl;
 Z is hydrogen, halogen, alkyl, haloalkyl, or hydroxy, optionally existing in its isomeric keto form; and
 Q is cyano or lower alkoxycarbonyl.

wherein for formula (IV):
 $R_2$, $R_3$, $R_4$, $R_5$ and $R_6$ are as defined in formula (I);
 X is hydrogen or haloalkyl, particularly trifluoromethyl;
 Y is amino; hydroxy, optionally existing in its isomeric keto form when X is hydrogen; or alkoxy or haloalkoxy, obtained by alkylation of hydroxy; and
 Z is hydrogen; halogen; alkyl; haloalkyl; hydroxy, optionally existing in its isomeric keto form when X is hydrogen and Y is imino; or alkoxy or haloalkoxy, obtained by alkylation of hydroxy.

Compounds of formula (I) of the invention can then be prepared by reaction of compounds of formula (IV) according to the subsequently described Methods introducing the various substituents, particularly X, Y and Z.

Particularly useful and novel intermediate phenyl imidazole compounds, discussed in the Methods herein for the preparation of compounds of the invention of formula (I), are specifically compounds of formulae (IV), (5), (17), (22), (27), (30)/(34), (Ia), (Ib), and (Ic). Additionally, compounds of formula (III) which are novel and useful are specifically compounds of formulae (4), (16), (21), (26), (28), and (33).

In particular, the more preferred 4-sulfenated 1-arylimidazoles ($X=S(O)_nR_1$, wherein n and $R_1$ are previously defined) of this invention can be prepared by a variety of methods. Two preferred methods are illustrated by reaction SCHEMES I and II (METHODS I and II).

Method I

According to Method I, a particularly useful compound of formula (I), namely (Ia),

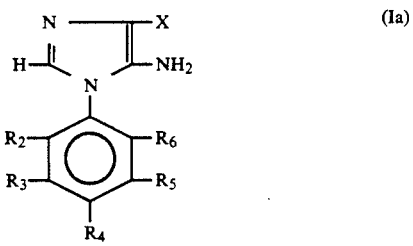

(Ia)

can be prepared wherein X, $R_2$, $R_3$, $R_4$, $R_5$ and $R_6$ are as defined in formula (I).

Method IA Compounds of general formula (I), in which X is alkylsulfenyl, haloalkylsulfenyl, alkylsulfinyl, haloalkylsulfinyl, alkylsulfonyl, and haloalkylsulfonyl, Y is amino, hydrogen, halogen, alkylsulfenyl, haloalkylsulfenyl, alkylsulfinyl, haloalkylsulfinyl, alkylsulfonyl, haloalkylsulfonyl, cyano or nitro, Z is hydrogen or halogen, and $R_2$, $R_3$, $R_4$, $R_5$ and $R_6$ are as defined in formula (I) can be prepared by procedures described in SCHEME I.

In SCHEME I the starting material, alkyl orthoformate (1), in which R' is a $C_1$ to $C_4$ alkyl group, is generally commercially available and the aniline (2) is usually also a commercial product or else it may be prepared following well-known literature procedures. The catalyst used for formimidate (3) formation is generally an inorganic acid such as hydrochloric acid or an organic acid such as p-toluenesulfonic acid. The reaction may be carried out at a temperature between about −20° C. and about 180° C., preferably between about 0° C. and about 120° C., in the presence of an inert organic solvent such as a hydrocarbon, a chlorinated hydrocarbon, an aromatic, an ether, an alcohol and the like or the alkyl orthoformate itself may be used as the solvent. The formimidate (3) may exist as a mixture of regioisomers.

The intermediate formimidine (4) is prepared by reaction of the formimidate (3) with aminoacetonitrile or the hydrochloride salt thereof in the presence of a base and in an inert organic solvent preferably capable of providing a homogeneous solution for the reactants. Typical organic and inorganic bases are alkoxides, hydroxides, hydrides, carbonates of alkali or alkaline earth metals, and amines such as diisopropylamine, tripropylamine, etc. Solvents which may be employed include inert organic solvents such as alcohols (e.g., methanol or ethanol), ethers (e.g., diethyl ether, tetrahydrofuran, dioxane or diglyme), amines (e.g., triethylamine or pyridine) or water or combinations of these solvents. The reaction is usually conducted at a temperature between about −20° C. and about 180° C., preferably between about 20° C. and about 120° C.

The intermediate formimidine (4) may either be isolated or cyclized in situ to imidazole (5) without isolation by further treatment with a base and under the conditions as described above, preferably using sodium methoxide in methanol at about 20°-25° C. Compounds of formulae (4) and (5) are new and are within the scope of the invention as intermediates in the methods or processes of synthesis of compounds of formula (I) of the invention.

The reaction of imidazole (5) with a sulfenyl halide, preferably chloride, $R_1SHalo$, in which $R_1$ is alkyl or haloalkyl, to give (6) conveniently may be conducted in an inert aprotic organic solvent such as a chlorinated hydrocarbon, a hydrocarbon, an ether, etc., preferably

SCHEME I

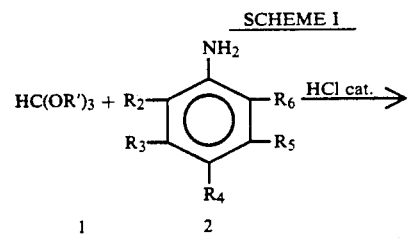

-continued
SCHEME I

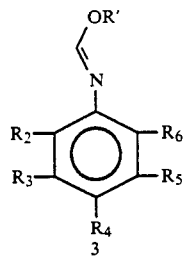

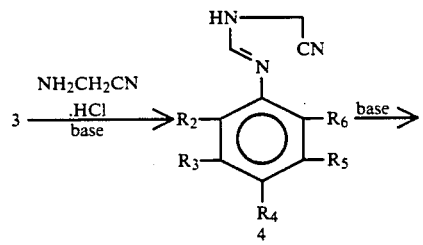

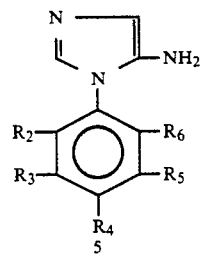

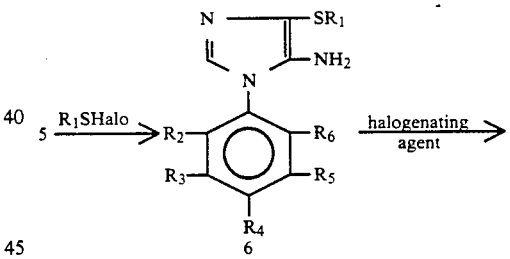

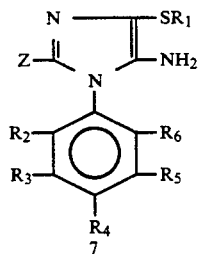

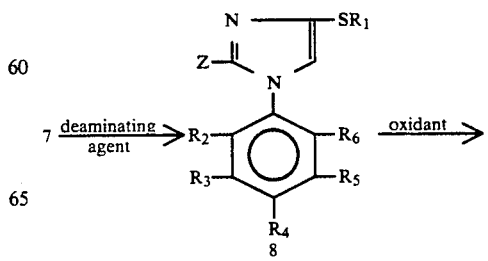

-continued
SCHEME I

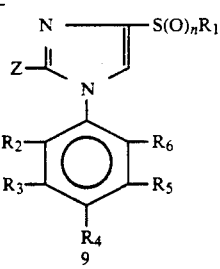
9 in dichloromethane, with or without an acid acceptor such as pyridine, any tertiary amine or an alkali metal carbonate. The reaction may be carried out between about −25° C. and about 100° C. depending on the boiling point of the sulfenyl halide reagent and the solvent.

The aminoimidazole (6) can be halogenated to the corresponding haloimidazole (7), Z is halogen, by reacting (6) with a halogenating agent such as sulfuryl chloride, thionyl chloride, chlorine or bromine and with or without an acid acceptor or a catalyst such as a Lewis acid. The reaction is conducted in an inert aprotic organic solvent such as a chlorinated hydrocarbon or an ether. The reaction may be carried out between about −50° C. and about 150° C., preferably between about −10° C. to about 110° C., depending on the reactivity of aminoimidazole (6) and the reactivity of the halogenating agent used.

The desaminoimidazole (8) may be prepared by reacting the aminoimidazole (7) with an organic nitrite, such as t-butyl nitrite, in an organic solvent such as tetrahydrofuran between about −20° C. to about 180° C., preferably between about 10° C. to about 100° C.

The oxidation of the sulfide (8), n=0, to the sulfoxide, n=1, or sulfone (9), n=2, may be carried out by using an appropriate quantity of peracetic acid, trifluoroperacetic acid, m-chloroperbenzoic acid, hydrogen peroxide, a combination of peracetic acid and hydrogen peroxide, or potassium peroxyamonosulfate which is commercially available as Oxone ®. The reaction is usually conducted in an inert organic solvent typically between about −30° C. to about 180° C.

Additionally, compounds of formula (7) of SCHEME I can be converted to other compounds of the present invention. In a first case of substitutive deamination, (7) is initially reacted with a deaminating agent, such as described for the conversion of (7) to (8), and then it is immediately reacted with a quenching agent such as bromoform, cupric chloride or dimethyl disulfide to produce a compound of general formula (I) of the invention, wherein Y is a halogen atom or an alkylsulfenyl (n=0) group, in which the alkyl is optionally halo-substituted, and Z is a halogen atom. The reaction is usually conducted in an inert organic solvent such as anhydrous acetonitrile, typically at a temperature between about −20° C. and about 180° C., preferably between about 10° C. and about 100° C. Further compounds, wherein Y are namely sulfoxides (n=1) and sulfones (n=2), of the invention can then be prepared by an oxidation reaction conducted in a similar manner for the conversion of (8) to (9).

In an alternative synthesis, a compound of formula (7) can be converted to a diazonium compound by reaction of the 5-amino substituent with nitrous acid at a temperature below about 5° C. Subsequent decomposition of the diazonium compound in the presence of, for example, cuprous chloride, bromide, cyanide or nitrite via a Sandmeyer reaction provides compounds of general formula (I) of the invention, wherein Y is, for example, a chlorine or bromine atom or a cyano or nitro group and Z is a halogen atom.

Compounds of formula (I) wherein Y is a derivatized amino group, as described in the definitions of Y in formula (I), can readily be prepared from a compound such as that of formula (6) or (7) by well known alkylation, acylation, etc., procedures. An example is a compound of formula (I), wherein Y is alkoxyalkylideneimino prepared from a compound in which Y is amino by reaction with an alkyl orthoformate, in the presence of an inorganic or organic acid catalyst at a temperature between about 0° C. to about 120° C. and optionally in an inert organic solvent, as described in Method IA above.

While the above reactions shown in synthetic Scheme I for (6) to (7) to (8) to (9) illustrate compounds (7), (8) and (9) in which Z is halogen, alternatively, the halogenation reaction of (6) to (7) can be omitted thereby providing the corresponding compounds, including compounds of formula (I) of the invention in which Z is hydrogen.

Method IB A compound of formula (I), in which X is haloalkoxy, Y is as previously defined in Method IA, preferably a hydrogen or an optionally protected amino group, Z is hydrogen or halogen, preferably hydrogen, and $R_2$, $R_3$, $R_4$, $R_5$ and $R_6$ have the meanings given in the general definition of the invention may be prepared by the following procedures:

a) A useful intermediate compound, wherein X is halogen, such as bromo, chloro or iodo, Y is preferably hydrogen, amino or a protected amino group, and $R_2$, $R_3$, $R_4$, $R_5$ and $R_6$ are as defined above, can be prepared by a commonly utilized halogenation method from a compound of formula (5) with an appropriate amount of halogenating agent such as bromine, chlorine, sulfuryl chloride, N-chlorosuccinimide or N-bromosuccinimide in a suitable solvent such as haloalkane, ether, tetrahydrofuran or acetonitrile at a reaction temperature from about −25° C. to about 100° C., preferably from about −10° C. to about 85° C. To prevent further halogenation at the 2-position of imidazolyl ring, a stoichiometric amount of halogenating agent may be used. The compound obtained may be deaminated following a procedure similar to that described in Method I to give an intermediate compound wherein Y is hydrogen and X is halogen.

b) An intermediate compound, in which X is hydroxy, Y is preferably hydrogen or a protected amino, Z is preferably hydrogen, and $R_2$, $R_3$, $R_4$, $R_5$ and $R_6$ are as defined above, may be prepared by converting the intermediate, in which X is halogen, into the corresponding Grignard reagent or the corresponding lithium derivative following commonly known procedures, then followed by treatment with oxodiperoxymolybdenum(pyridine)(hexamethylphosphoric triamide) (MoOPH) by a procedure similar to that described by N. J. Lewis et. al. in J. Org. Chem., 1977, 42, 1479. Alternatively, the Grignard reagent or the lithium derivative described above may be reacted with a trialkyl borate followed by oxidation with hydrogen peroxide or other oxidizing agents to produce the hydroxy analog by a procedure similar to that reported by M. F.

Hawthorne, J. Org. Chem., 1957, 22, 1001 or R. W. Hoffmann and K. Ditrich, Synthesis, 1983, 107.

c) A compound of formula (I), in which X is haloalkoxy, Y is preferably hydrogen or a protected amino, Z is preferably hydrogen, and $R_2$, $R_3$, $R_4$, $R_5$ and $R_6$ are as defined above, may be prepared from a corresponding compound in which X is hydroxy, Y is preferably hydrogen or protected amino, Z is preferably hydrogen, and $R_2$, $R_3$, $R_4$, $R_5$ and $R_6$ are as defined above, by various haloalkylating methods described in Synthesis of Fluoroorganic Compounds; Knunyants, I, L, and Yakobson, G. G., Ed.; Springer-Verlag: Berlin, 1985; pp 263-269, followed by a deprotection step, if necessary.

Method IC A compound of formula (I), in which X is haloalkyl, Y is as defined previously in Method IA, preferably an amino or protected amino, Z is hydrogen or halogen, preferably hydrogen, and $R_2$, $R_3$, $R_4$, $R_5$ and $R_6$ are as defined above, can be prepared from a compound of formula (5), following the sequence below:

a) Preparation of an intermediate compound, i.e. formula (11), in which X is formyl, Y is preferably amino or protected amino, Z is preferably hydrogen, and $R_2$, $R_3$, $R_4$, $R_5$, $R_6$ are as defined before, can be prepared by various methods of synthesis such as the Gattermann and Koch reaction, the Reimer-Tiemann reaction, the Vilsmeier-Haack reaction or modification of these methods. Under Vilsmeier conditions, the formylation can be carried out by treating a compound of formula (5), in which X is hydrogen, with a disubstituted formamide, such as dimethyl formamide or N-phenyl-N-methylformamide, and phosphorous oxychloride which may be replaced with a halogen acid anhydride such as thionyl chloride, oxalyl chloride or phosgene. The reaction temperature may be from about $-10°$ C. to about $200°$ C., preferably from about room temperature to about $100°$ C. Solvents to be used are those inert to the Vilsmeier Reaction and to the reagents involved, such as dichlorobenzene, carbon tetrachloride or dichloromethane. Another method of formylating a compound of formula (5) is to hydrolyze an intermediate compound, i.e. formula (10), in which X is bis(alkylthio)methyl or bis(arylthio)methyl (Ra is alkyl or aryl), by treating with an alkylnitrite, preferably isoamyl nitrite, in a suitable solvent such as a halogenated alkane, preferably dichloromethane, followed by a hydrolysis procedure similar to that reported by E. Fujita et. al, Tet. Let., 1978, 3561. Protection of the amino group with an appropriate protecting group may be necessary during the reaction with alkyl nitrites. The process for conversion of (10) to (11) may be generally represented as follows:

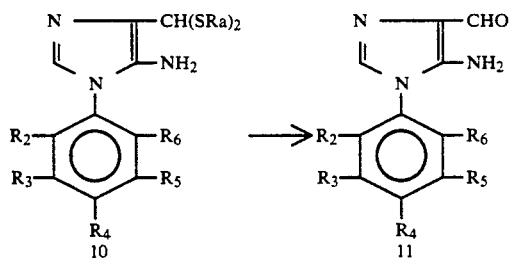

An intermediate compound, i.e. formula (10), in which X is a bis(alkylthio)methyl or bis(arylthio)methyl group, Y is preferably amino, Z is preferably hydrogen, and $R_2$, $R_3$, $R_4$, $R_5$, and $R_6$ are those herein above defined for the definition of the invention, can be prepared by reaction of a compound of the formula (5) with tris(alkylthio)methane or tris(arylthio)methane, $(RaS)_3CH$, in the presence of a thiophilic Lewis Acid, preferably a sulfonium salt, such as dimethyl-(methylthio)-sulfonium tetrafluoroborate in an aprotic solvent, at a temperature between about $-10°$ C. and about $100°$ C., optionally in the presence of an acid accepter such as pyridine. A more preferred process employs acetonitrile or dichloromethane as solvent at about $25°$ C. with tris(methylthio)methane as the tris(alkylthio)methane and dimethyl(methylthio)sulfonium tetrafluoroborate as the Lewis acid without an acid acceptor. A typical procedure is reported by R. A. Smith et. al., Synthesis, 166, 1984. The process is represented as shown below:

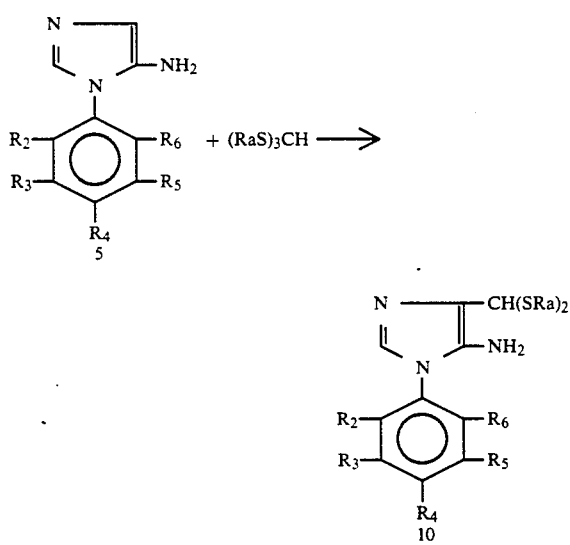

b) Preparation of an intermediate compound, i.e. formula (12), in which X is hydroxymethyl, Y is preferably amino or protected amino, Z is preferably hydrogen, and $R_2$, $R_3$, $R_4$, $R_5$ and $R_6$ have the meanings given in the definition of the invention, may be prepared by reduction of compounds of the formula (11). The reduction can be conducted with a reducing agent such as lithium aluminum hydride, sodium borohydride, aluminum isoproxide, borane and substituted boranes, and other metal hydrides in a suitable aprotic or protic solvent. For more reactive hydrides, e.g. lithium aluminum hydride, the reaction may be conducted in an inert solvent such as tetrahydrofuran, ethyl ether or dimethoxyethane, at a reaction temperature from about $-10°$ C. to about $120°$ C., preferably at a temperature from about $20°$ C. to about $100°$ C. For milder hydrides, such as sodium borohydride, the reaction may be conducted in an alcohol such as methanol at a temperature from about $-10°$ C. to about $100°$ C., preferably from about room temperature to about $75°$ C.

c) A compound, i.e. formula (13), wherein X is haloalkyl, specifically chloromethyl, fluoromethyl, bromomethyl or iodomethyl, Y is preferably amino or protected amino, Z is preferably hydrogen, and $R_2$, $R_3$, $R_4$, $R_5$, and $R_6$ have the meanings given in the definition of the invention, can be prepared from intermediate compounds of formula (12), wherein X is hydroxymethyl, by using an appropriate

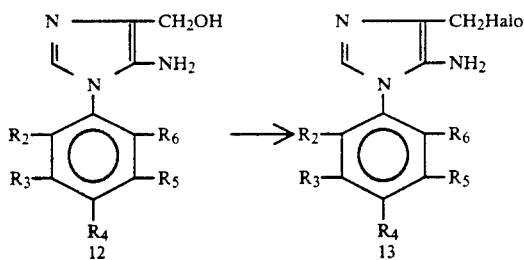

chlorinating, fluoronating or brominating agent. For chlorination, the reaction may be carried out with reagents such as thionyl chloride, phosphorous trichloride, phosphorous pentachloride or phosphorous oxychloride in dichloromethane or ethyl ether at a reaction temperature from about $-20°$ C. to about $100°$ C. The reaction can be carried out with or without the presence of an acid acceptor such as triethylamine or pyridine. For fluorination, the reaction can be conducted with dialkylaminosulfur trifluoride in a solvent such as acetonitrile, dichloromethane or glyme at a reaction temperature from about $-20°$ C. to about $100°$ C. A more preferably condition uses diethylaminosulfur trifluoride in acetonitrile at about room temperature. A representative procedure is given by W. J. Middletown, J. Org. Chem., (1975), 42, 5, 574. Other fluororinating reagents that may be used are sulfur trifluoride, bis(dialkylamino)-sulfur trifluoride or sodium or potassium fluoride in a polyhydrogen fluoride-pyridine solution. The procedure is similar to that reported by Olah and Welch, Synthesis, 653, (1974). For bromination, the reaction may be conducted with brominating agents such as bromine, n-bromosuccinimide, phosphorous tribromide or hydrogen bromide in an inert solvent such as dichloromethane or ethyl ether at a temperature from about $-20°$ C. to about $100°$ C. For iodidation, the reaction may be performed with hydrogen iodide in an inert solvent such as dichloromethane at a reaction temperature from about $-20°$ C. to about $100°$ C. The above-mentioned halogenations can be carried out with a deactivating group attached to the amino function such as an acyl group to prevent the additional halogenation at the 2-position of the imidazolyl ring.

d) Alternatively, a compound of formula (I), in which X is a haloalkyl group, Y is preferably amino, Z is preferably hydrogen, and $R_2$, $R_3$, $R_4$, $R_5$ and $R_6$ are as defined above, may be prepared from the corresponding compound in which X is a formyl group or a carboxylic function and the Y amino group is optionally protected. For example, treatment of the formyl compound with diethylaminosulfur trifluoride in a manner analogous to that described by W. J. Middleton in J. Org. Chem, 1975, 40, 574 provides the compound of formula (I) in which X is a difluoromethyl group and the other substituents are as defined above. Oxidation of the above mentioned intermediate compound, wherein X is formyl, with an oxidizing agent such as potassium permanganate in acetone-water or chromium trioxide in sulfuric acid, known as Jones' reagent, give an intermediate compound, wherein X is carboxyl, Y is preferably amino, Z is preferably hydrogen, and $R_2$, $R_3$, $R_4$, $R_5$ and $R_6$ are as defined above. Reaction of the compound above in which X is carboxyl with sulfur tetrafluoride, similar to that described by G. A. Boswell et. al. Org. Reaction, 1974, 21, 1-124, gives the compound of formula (I) in which X is a trifluoromethyl group and the other groups are as defined above.

Method II

A compound of formula (I) of the invention, wherein X and Y are as defined and prepared by the Methods IA, IB, and IC, Z is halogen, preferably chlorine, and n, $R_1$, $R_2$, $R_3$, $R_4$, $R_5$ and $R_6$ are as previously defined, can be prepared by procedures described in SCHEME II.

According to SCHEME II, intermediates of formulae (14) and (15) may be prepared in a similar manner to the method described in GB Patent Specification No. 2,203,739, incorporated herein by reference.

For the subsequent reactions, the conditions used in the alkylation of (15) to (16), the ring closure of (16) to (17) and the preferred sulfenylation substitution of (17) to (18) are similar to the ranges of reaction parameters described for related compounds, i.e., compounds of formulae (3) to give (4), (4) to give (5), and (5) to give (6), respectively, prepared according to SCHEME I. Compounds of formulae (17) and (18) of SCHEME II are analogous to compounds of formulae (5) to (7) of SCHEME I and thus compounds of formulae (17) and (18) can be converted to other compounds of the invention, wherein Z is halogen and X, Y, n, $R_1$ to $R_6$ are as defined in Method I, in a similar manner as described in SCHEME I and Method I or alternatives thereto. Compounds of formulae (16) and (17) are new and are within the scope of the invention as intermediates in the methods or processes of synthesis of compounds of formula (I) of the invention.

Method III

A compound of the formula (I), in which Z is an alkyl or halogen substituted alkyl group, and X, Y, n, $R_1$, $R_2$, $R_3$, $R_4$, $R_5$ and $R_6$ are as defined in Method I or in the definition of formula (I), can be prepared

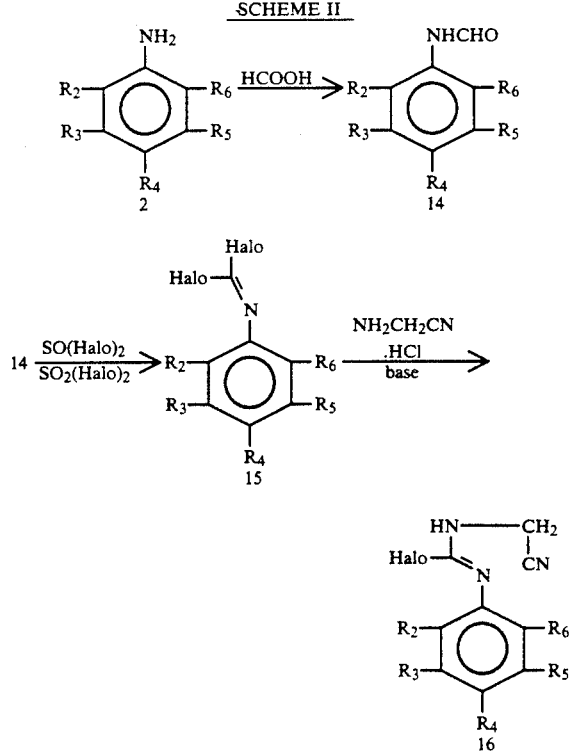

SCHEME II -continued

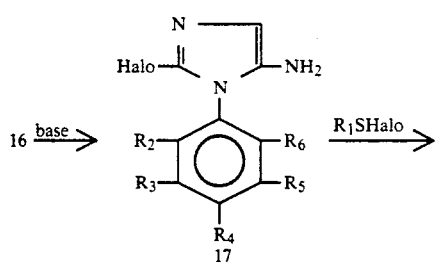

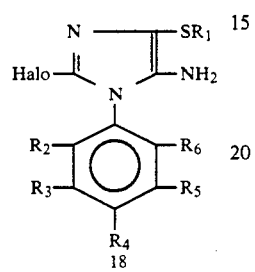

SCHEME III

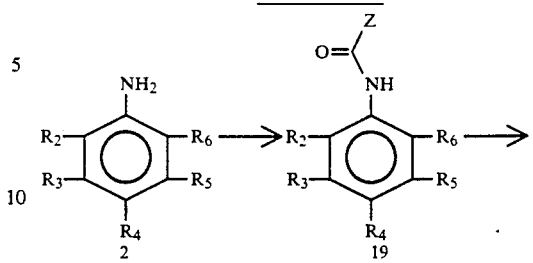

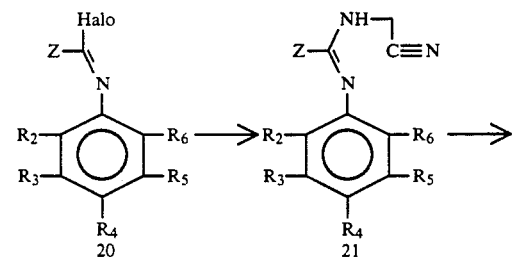

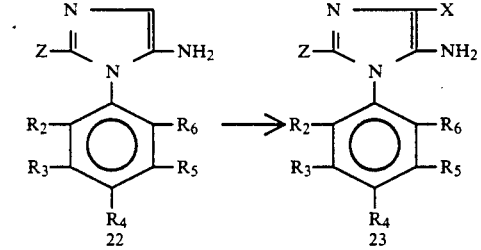

according to the SCHEME (III). The amide (19) can be prepared by well known methods using an acyl halide, anhydride or ester. When reacting with an acyl halide, a base may be used as a catalyst or the aniline is converted to the corresponding amide anion with metal hydride or metal alkane. The reaction temperature may be from about 4° C. to about 100° C. for the acyl halide reaction. When using an anhydride, the reaction may be conducted with various inorganic or organic acid catalysts, Lewis acids or basic catalysts, such as pyridine or triethylamine. The reaction temperature may be from about −10° to about 150° C. This reaction may be enhanced with a metal catalyst, such as zinc dust.

The amide (19) can be halogenated into an imido halide (20) using a halogenating agent such as phosphorous pentahalide in an inert solvent such as dichloromethane, acetonitrile or chloroform. The preferred solvents are halogented alkanes, such as chloroform and dichloromethane. The alkylation to (21) may be conducted with aminoacetonitrile or its hydrochloride salt in the presence of a base, such as a carbonate, hydroxide or trialkylamine, preferably potassium carbonate in an appropriate solvent, such as tetrahydrofuran, acetonitrile or chloroform. The ring closure to (22) can be achieved by treating the amidine (21) with a catalytic amount of a base, such as an amine or alkali, hydroxide or alkoxide in a suitable solvent, such as an alcohol or halogenated alkane. The reaction is preferably carried out with sodium methoxide in anhydrous methanol at ambient temperature. The ring closure to (22) can also be achieved in a one step reaction from (20) via (21) by using more than one equivalent of aminoacetonitrile in a suitable solvent such as chloroform at reflux temperature.

A compound of formula (23), wherein Z is alkyl or haloalkyl, Y is amino, $R_2$ to $R_6$ are as defined for general formula (I), and X is alkylsulfenyl, haloalkylsulfenyl, alkysulfinyl, haloalkylsulfinyl, alkylsulfonyl, haloalkylsulfonyl, haloalkyl or haloalkoxy, can be prepared by the procedures described in Method I.

Further compounds of the invention, wherein Y is defined by formula (I), can be prepared from a compound of formula (23) by the Methods herein described for the conversion of Y is amino into other defined Y substituents of formula (I).

Method IV

A compound of formula (I), in which X is haloalkyl, particularly perfluoroalkyl, Y is amino or may be additionally other Y substituents defined by formula (I), Z is halogen, alkyl or haloalkyl, and $R_2$, $R_3$, $R_4$, $R_5$ and $R_6$ have the meanings given in the definition of formula (I), may be prepared by the sequences described below:

The intermediate compound of formula (25) can be prepared by reacting the known iminolperfluoronitrile, (24), with a compound of formula (20) in the presence of a base catalyst such as pyridine at a reaction temperature from about −75° C. to about 100° C., preferably at the temperature from about 0° C. to about 85° C. Iminoperfluoronitriles are known compounds and various compounds of this type can be prepared according to the procedure reported by W. J. Middleton and C. G. Krespan *J. Org. Chem.*, 33, 9, 3625, (1968). The nucleophilic property of iminoperfluoronitrile with a basic catalyst has also been demonstrated in the same report. The transformation is represented by the following equation:

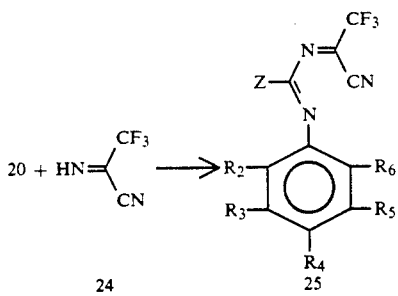

The intermediate compound of formula (25), described above, can be treated with a reducing agent, such as sodium borohydride in an inert solvent such as an alcohol or ether, at a reaction temperature from about 0° C. to about 85° C. to produce an intermediate compound of formula (26). Sodium borohydride, in general, reduces an imino function, but keeps the nitrile function unaffected (see Jerry March, "Advanced Organic Chemistry, McGraw-Hill Book Company, p. 834–835, 2nd Edition and references cited therein).

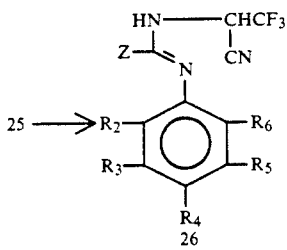

The intermediate of formula (26) can then be ring-closed in the same fashion as that described in Method I to give a compound of the invention of formula (27), wherein Z is halogen, alkyl or haloalkyl, and $R_2$ to $R_6$ are as defined in formula (I) of the invention.

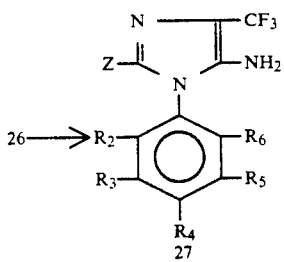

Further compounds of the invention, wherein Y is defined by formula (I), can be prepared from a compound of formula (27) by Methods described herein for the conversion of Y is amino into other defined Y substituents of formula (I).

Method V

A compound of formula (I), wherein Y is a hydroxy, alkoxy or haloalkoxy, Z is alkyl, haloalkyl or halogen, X is as defined for formula (I), preferably perhaloalkylsulfenyl, perhaloalkylsulfinyl, perhaloalkylsulfonyl, and $R_1$, n, $R_2$, $R_3$, $R_4$, $R_5$ and $R_6$ have the meanings given previously, can be prepared by the following processes:

a) A compound of the formula (28), in which Z is alkyl, haloalkyl, halogen, and $R_2$, $R_3$, $R_4$, $R_5$, and $R_6$ are herein above defined for the general definition of formula (I), can be prepared by alkylation with glycine or a glycine ester of an appropriate imino halide, such as the compound indicated by the formula (20), from SCHEME III, wherein Z is halogen, alkyl or haloalkyl. The reaction can be conducted in an inert organic solvent, such as dichloromethane, chloroform, tetrahydrofuran or ethyl ether at a reaction temperature from about −20° C. to about 150° C., depending on the size and the electronic effect of the Z group. In the subsequent reactions, the conditions for the ring closure to the compound of formula (29) (or its enolate form (30) or salts thereof, and the sulfenylation of a compound of formula (30) or salts thereof to a compound of formula (31) and salts thereof are similar to the ranges of reaction parameters described for related compounds, i.e., compounds of formula (4) to give (5), and (5) to give (6), respectively according to SCHEME I, Method I. The corresponding compound, in which Y is alkoxy or haloalkoxy, can be prepared following the well known Williamson synthesis. The ether formation can be achieved by reacting the preformed alkoxide in an inert solvent, such as ethyl ether or tetrahydrofuran, with an appropriate alkylating agent such as an alkyl halide or alkyl sulfate at a reaction temperature of about −10° C. to about 100° C., preferably at a temperature from about 4° C. to about 50° C. The ether formation may be more efficiently carried out in two phases involving use of a phase-transfer catalyst. An example of the reaction system is: water, dichloromethane, a quaternary ammonium hydroxide, a compound of formula (31) and an alkyl halide. The procedure may be similar to the one reported by Freeman and Dubois, Tet. Let, 3251 (1975). The intermediate compound of formula (30), before sulfenylation, may be optionally alkylated or haloalkylated by the methods described above followed by alkysulfenylation or haloalkylsulfenylation according to procedures parallel to those described in Method I to obtain a compound of formula (32). Compounds of formulae (31) and (32) may be oxidized by the procedures also outlined in Method I to prepare the corresponding sulfoxide (n=1) and sulfone (n=2) compounds, $X=S(O)_nR_1$, in which $R_1$ is as previously defined.

Additionally, a compound of formula (I), wherein Z is alkyl, haloalkyl or halogen, Y is hydroxy, alkoxy, or haloalkoxy and X, and $R_2$ to $R_6$ are as defined for formula (I), may be prepared from the compound of formula (30), or optionally alkoxylated or haloalkoxylated analogs thereof, by appropriate conversion of the compound in which X is hydrogen, to an X substituent defined for formula (I) by the Methods describe herein.

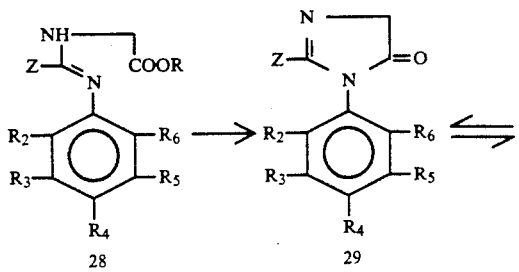

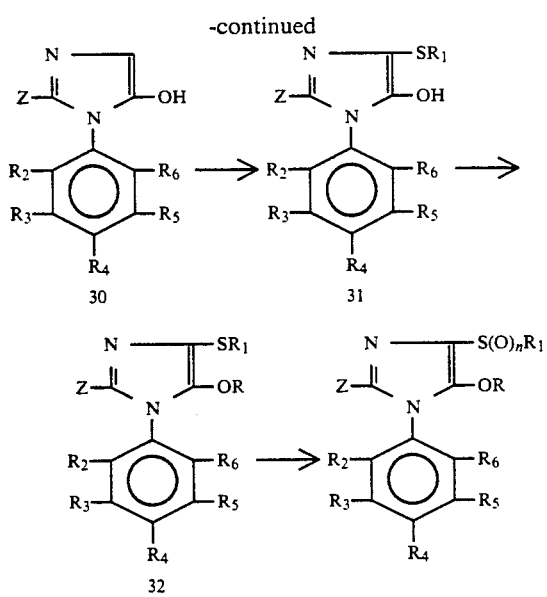

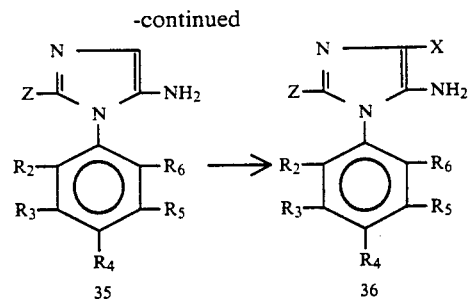

b) A compound of formula (I), in which Z is hydroxy or salts thereof, alkoxy, haloalkoxy, Y is amino, hydrogen or halogen, and X, $R_2$, $R_3$, $R_4$, $R_5$ and $R_6$ have the meanings described in the definition of the invention, may be prepared from a compound of formula (34) wherein $R_2$, $R_3$, $R_4$, $R_5$ and $R_6$ are as defined above, by the scheme described below:

The iminohydantoin (34) may be aromatized into its corresponding 2-hydroxy-5-aminoimidazole (37) or salts thereof by an appropriate PH control in a suitable solvent. The hydroxy imidazole of formula (37) or salts thereof can be sulfenylated with an appropriate sulfenyl halide, $R_1$SHalo, preferably chloride, to give a compound where Z is hydroxy, Y is amino, and X is $S(O)_nR_1$, in which n is 0 and $R_1$ is as defined, by procedures similar to those described in Method I. The corresponding desamino analog (Y is hydrogen) may be prepared by deamination with t-butylnitrite or via the diazonium intermediate following a procedure similar to that described in Method I. By the Sandmeyer reaction, the 5-halo-2-hydroxyimidazole may thus be prepared. Additionally, the sulfenylated analogs above may be deaminated to give compounds wherein X is $S(O)_nR_1$, Y is alkylsulfenyl or halogen, and Z is hydroxy or halogen.

The 2-alkoxy- or 2-haloalkoxy-3-sulfenylated-imidazole analogs (Z is alkoxy or haloalkoxy) of formula (39) may be prepared via the intermediate compound (38) which may be prepared by direct alkylation with an appropriate alkylating agent, such as alkyl iodide, haloalkyl iodide, alkyl bromide and dialkylsulfate, of a compound of formula (34)/(37) in a suitable solvent, such as tetrahydrofuran, alcohol, acetonitrile, acetone, etc., at a reaction temperature from about room temperature to about 150° C., preferably from about room temperature to about 100° C. The subsequent sulfenylation to (39) can be conducted according to a procedure similar to that described in Method I for general sulfenylation. Alternatively, the alkylation step to a compound in which Z is alkoxy or haloalkoxy may be carried out after the sulfenylation and deamination by procedures similar to those described above. If the O-alkylation is to be carried out prior to deamination an appropriate amino protection group (W) may be introduced before the O-alkylation reaction and then subsequently removed.

Additionally, from the various above compounds, wherein Z is hydroxy or salts thereof, alkoxy or haloalkoxy, X is hydrogen, and Y is

Method VI

A compound of formula (I), wherein Z is hydroxy, alkoxy, haloalkoxy or halogen, Y is the substituent defined in formula (I), particularly amino, X is the substituent defined in formula (I), particularly $S(O)_nR_1$, and n, $R_1$ and $R_2$ to $R_6$ are as previously defined, can be prepared according to the following synthetic sequences:

a) The appropriate aniline is first converted into the corresponding isocyanate by treatment of the aniline with phosgene or oxalyl chloride in an inert solvent such as dichloromethane or chloroform. The isocyanate compound is then to reacted with aminoacetonitrile to give the urea of formula (33). The urea compound of formula (33) can be ring-closed into the corresponding iminohydantoin of formula (34) or salts thereof in the presence of a base such as an alkali alkoxide or amine. The iminohydantoin can then be chlorinated with chlorinating agents such as phosphorous pentachloride, thionyl chloride, phosphorous oxychloride or phosphorous pentachloride, preferably with phosphorous pentachloride, at a reaction temperature from about −10° C. to about 180° C., preferably from about room temperature to about 100° C. The 2-halogenated imidazole (Z is halogen), (35), or salts thereof can then be alkylsulfenylated into the desired alkyl or haloalkyl sulfenyl products of formula (36), in which X is $SR_1$. These sulfenylated compounds (36) can then be further oxidized into other compounds of the invention, namely sulfoxides or sulfones, $S(O)_nR_1$ in which n is 1 or 2 and $R_1$ is as defined. The procedures for sulfenylation and oxidation are similar to those described in Method I.

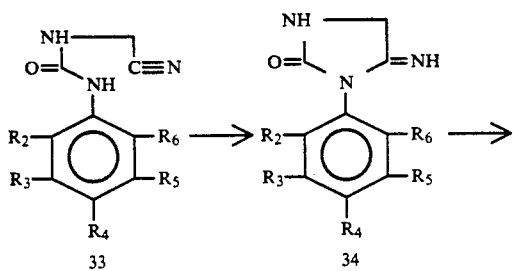

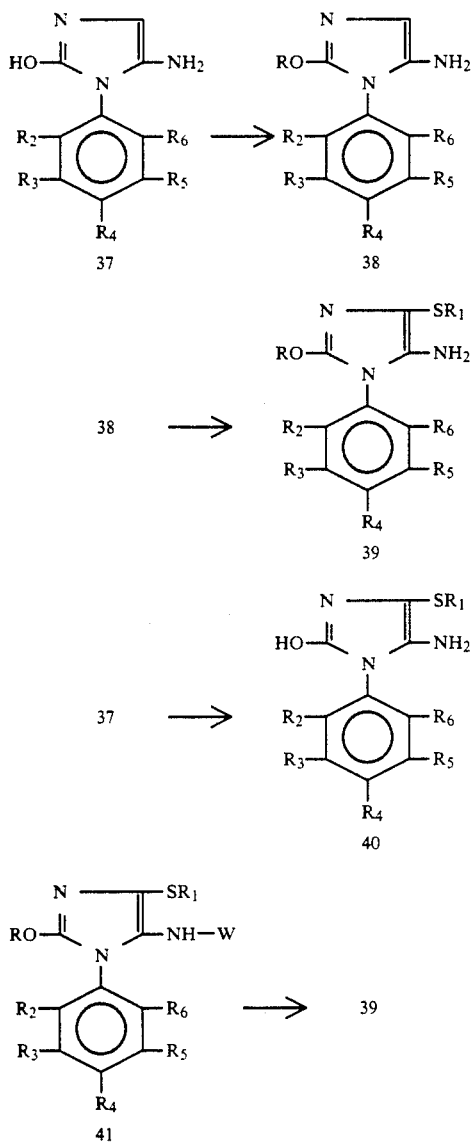

amino or hydrogen, other compounds of the invention of formula (I), wherein X and Y are defined in formula (I), can be prepared according to the Methods described herein, specific for X and Y.

Methods VII to XXVIII Generalization

The following Methods VII to XXVIII detail specific procedures for introducing a Z substituent into a particular compound of formula (Ia) to provide a further useful compound of formula (Ib).

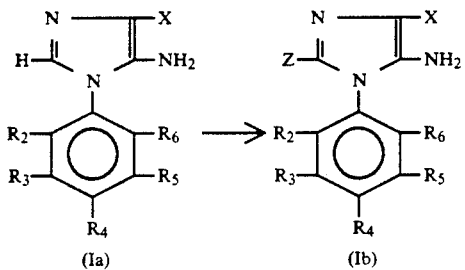

Method VII

A compound of formula (Ib), in which Z is aminosulfonyl, alkylaminosulfonyl or dialkylaminosulfonyl, Y is $NH_2$, and X, $R_2$, $R_3$, $R_4$, $R_5$ and $R_6$ have the meanings given in the definition of formula (I), can be prepared from a compound of formula (I), wherein Z is hydrogen, Y is amino, and X, $R_2$, $R_3$, $R_4$, $R_5$ and $R_6$ have the meanings herein above defined, by the following sequence:

a) An intermediate compound of formula (Ib), in which Z is chlorosulfonyl, Y is amino, and X, $R_2$, $R_3$, $R_4$, $R_5$ and $R_6$ have the meanings given in the definition of formula (I) may be prepared by treating a compound of formula (Ia), wherein Z is hydrogen and X, Y, and $R_2$ to $R_6$ are as defined above, with chlorosulfonic acid or dichlorosulfonic acid.

b) The compound of formula (Ib), wherein Z is aminosulfonyl, alkylamino-sulfonyl or dialkylaminosulfonyl, can be prepared by reacting the chlorosulfonyl intermediate with ammonia or an appropriate alkylamine or dialkylamine in a suitable solvent such as halogenated alkane, ether, tetrahydrofuran or hexane, at a reaction temperature from about $-50°$ C. to about $50°$ C., preferably from about $-20°$ C. to about room temperature.

Method VIII

A compound of formula (Ib), in which Z is nitro or halogen, Y is amino or protected amino, and X, $R_2$, $R_3$, $R_4$, $R_5$ and $R_6$ have the meanings given in the definition of formula (I), can be prepared by direct nitration or halogenation of a compound of formula (Ia), wherein Z is hydrogen, and X, Y, $R_2$, $R_3$, $R_4$, $R_5$ and $R_6$ are as defined above.

The nitration may be conducted with variety of nitrating agents, such as a mixture of concentrated nitric acid and sulfuric acid in acetic acid or acetic anhydride, dinitrogen pentaoxide in halogenated alkane, an ester of nitric acid such as ethyl nitrate, a mixed anhydride such as acetyl nitrate, nitryl halide with or without a Friedel-Crafts catalyst such as ferric chloride or methyl nitrate, or a nitronium salt such as nitronium tetrafluoroborate. The reaction may be conducted in a suitable solvent, such as acetic acid, acetic anhydride, tetramethylene sulfone, tetrahydrofuran or water under neutral, basic or acidic conditions at a reaction temperature from about $-50°$ C. to about $155°$ C. A preferred procedure is to conduct the nitration using nitryl chloride in the presence of titanium tetrachloride in tetramethylene sulfone at a reaction temperature from about $-10°$ C. to about $25°$ C.

The corresponding amino derivative of formula (Ib), Z is amino, may then be conveniently prepared by a standard reduction of the above-mentioned nitro analog. A variety of reducing agents are well known. Examples are zinc, tin, or iron with hydrochloric acid reduction, catalytic hydrogenation and sulfides such as NaHS, $(NH)_4S$ or polysulfide.

The compound of formula (Ib), in which Z is halogen, may be obtained from a compound of (Ia), wherein Z is hydrogen according to halogenation procedures similar to those in Method IB.

Method IX

A compound of formula (Ib), in which Z is alkyl, hydroxyl and salts thereof, alkoxy or haloalkoxy, Y is amino or protected amino, and X, $R_2$, $R_3$, $R_4$, $R_5$ and $R_6$ have meanings given in the definition of formula (I), may be prepared from a compound of formula (Ia), wherein Z is hydrogen and the other groups are as defined above, by treatment with a strong base, preferably an organic base such as lithium diisopropylamide or n-butyllithium in a suitable solvent such as tetrahydrofuran or ethyl ether to give an organometalic carbanion. By quenching the carbanion with an appropriate alkylating agent such as alkyl halide or dialkysulfate the compound in which Z is alkyl is obtained. Alternatively, the carbanion can be reacted, according to procedures similar to those described in Method IB, to first give a compound wherein Z is hydroxyl and then by standard alkylating conditions, the compound in which Z is alkoxy or haloalkoxy is obtained.

Method X

A compound of the formula (Ib), wherein Z is formyl, Y is amino and X, $R_2$, $R_3$, $R_4$, $R_5$ and $R_6$ have the meanings given in the definition of formula (I), that is to say a compound of the formula (42), may be prepared by the Vilsmeier-Haack Reaction or modifications thereof. This formylation can be carried out by treating a compound of formula (Ia), e.g. (6) in which Z is hydrogen, with a disubstituted formamide, such as dimethyl formamide or N-phenyl-N-methyl-formamide, and phosphorous oxychloride which may be replaced with a halogen acid anhydride such as thionyl chloride, oxalyl chloride or phosgene. The reaction temperatures may be from about $-10°$ C. to about 200° C., preferably from about room temperature to about 100° C. Solvents to be used are those inert to the Vilsmeier Reaction and to the reagents involved, such as dichlorobenzene, carbon tetrachloride or dichloromethane.

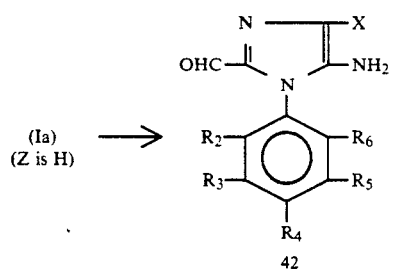

Method XI

Another method of formylating to give a compound of formula (Ib), wherein Z is formyl, Y is amino, and X, $R_2$, $R_3$, $R_4$, $R_5$ and $R_6$ are as defined in formula (I), is described as follows.

A compound of formula (42), wherein Z is formyl, can be prepared by hydrolyzing a compound of formula (43), wherein Z is a bis(alkylthio)- or bis(arylthio)-methyl group. This is done by treating (43) with an alkylnitrite in a suitable solvent such as a halogenated alkane, preferably isoamyl nitrite in dichloromethane, followed by hydrolysis similar to the procedure reported by E. Fujita et. al., Tet. Let., 1978, 3561. Protection of the amino group with an appropriate protecting group may be necessary during the reaction with alkyl nitrites. The process may be generally represented as follows:

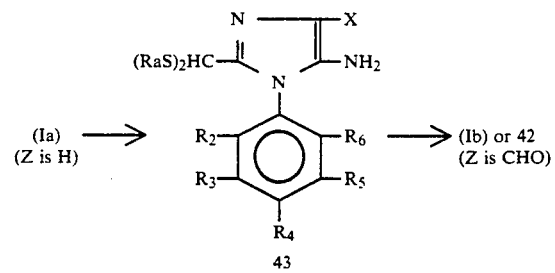

Method XII

An intermediate compound of formula (43), in which Z is a bis(alkylthio)methyl or bis(arylthio)methyl group, Y is amino, and X, $R_2$, $R_3$, $R_4$, $R_5$, and $R_6$ are those herein above defined for the definition of formula (I), can be prepared by reaction of a compound of the formula (Ia), e.g. (6), in which Z is hydrogen and X, Y, and $R_2$ to $R_6$ are as defined above, with tris(alkylthio)methane or tris(arylthio)methane, $(RaS)_3CH$, in the presence of a thiophilic Lewis Acid, preferably a sulfonium salt such as dimethyl(methylthio)sulfonium tetrafluoroborate in an aprotic solvent at a temperature between about $-10°$ C. and about 100° C., optionally in the presence of an acid accepter such as pyridine. A more preferred process employs acetonitrile or dichloromethane as solvent at about 25° C. with tris(methylthio)methane as the tris(alkylthio)methane and dimethyl(methylthio)sulfonium tetrafluoroborate as the Lewis acid, without an acid acceptor. A typical procedure is reported by R. A. Smith et. al., Synthesis, 166, 1984.

Method XIII

A compound of formula (Ib), in which Z is methyl, Y is amino, and X, $R_2$, $R_3$, $R_4$, $R_5$ and $R_6$ have the meanings given in the definition of formula (I), may be conveniently prepared by reduction of a compound of formula (Ia), i.e. (42), wherein Z is formyl and the other groups are as defined above. The reduction may be conducted with sodium borohydride in a suitable solvent such as an alcohol at a reaction temperature from about $-10°$ C. to about 120° C., preferably in methanol at a temperature from about room temperature to about 80° C. Alternatively, the analog wherein Z is methyl may be prepared by a sequential treatment of the formyl compound, (42), with p-toluenesulfonylhydrazine and sodium cyanoborohydride according to a method similar to that described in J. Am. Chem. Soc. 1971, 93, 1793.

Method XIV

A compound of formula (Ib), i.e. (44), in which Z is a carboxylic group of salts thereof, Y is amino or protected amino, and X, $R_2$, $R_3$, $R_4$, $R_5$ and $R_6$ have the meanings given in the definition of formula (I), can be prepared from a compound of formula (42), in which Z is formyl, by treatment with a variety of oxidizing agents such as potassium permangante in acid, basic or neutral solution, chromic acid, bromine, silver oxide or molecular oxygen in a suitable solvent. Selection of solvent will depend on the solubility of oxidizing agent and the substrate. Examples of solvents are acetone, water, alcohol, tetrahydrofuran, dimethoxyethane acetonitrile or a halogenated hydrocarbon such as dichloromethane or chloroform. The reaction temperature may range from about −20° C. to about 150° C., preferably from about room temperature to about 100° C.

Method XV

A compound of formula (Ib), i.e. (45), in which Z is cyano, Y is amino or protected amino, and X, $R_2$, $R_3$, $R_4$, $R_5$ and $R_6$ have the meanings given in the general definition of formula (I), may be prepared by reaction of a compound of formula (44), in which Z is carboxyl, with isophthalonitrile at a reaction temperature from about 100° C. to about 300° C. A representative example of a procedure for the transformation is given in J. Org. Chem, 1958, 23, 1350.

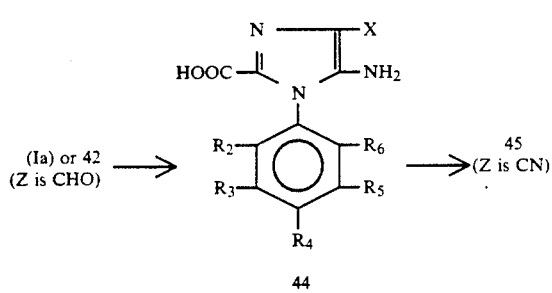

Method XVI

Alternatively, the cyano analog of formula (45), wherein Z is cyano, Y is amino or protected amino, and X, $R_2$, $R_3$, $R_4$, $R_5$ and $R_6$ are as defined by formula (I), can be prepared by the sequential transformation of a formyl compound of formula (42), in which Z is formyl, to its corresponding aldoxime of formula (46), in which all other substituents are as defined in formula (42), followed by a dehydration reaction. The dehydration reaction may be achieved with variety of dehydrating agents, such as acetic anhydride, diphenyl hydrogen phosphonate, 2,4,6-trichlorotriazene or ethylorthoformate and acid. Preferably the dehydrating agent is acetic anhydride at a reaction temperature from about −10° C. to about 180° C. The aldoxime intermediate of formula (46) can be prepared by reacting an aldehyde of formula (42) with hydroxyamine in a suitable solvent such as an alcohol, tetrahydrofuran, water, a halogenated hydrocarbon or a mixture solvent of halogenated hydrocarbon, alcohol and water. The reaction temperature may range from about −10° C. to about 120° C., preferably from about 4° C. to about 50° C.

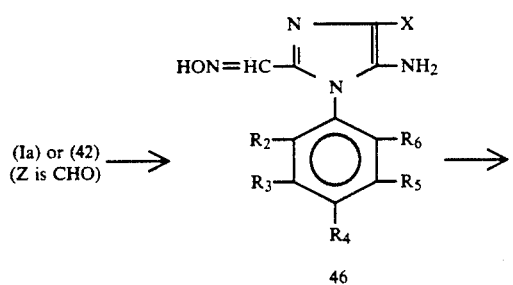

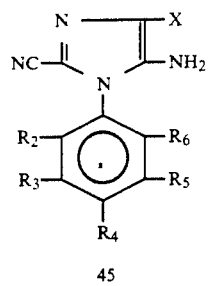

Method XVII

A compound of formula (Ib), i.e. (48), in which Z is aminocarbonyl, alkylaminocarbonyl, dialkylaminocarbonyl or alkoxycarbonyl (Z is COZ' in which $Z^1$ is amino, aklylamino, dialkylamino or alkoxy), Y is amino or protected amino, and X, $R_2$, $R_3$, $R_4$, $R_5$ and $R_6$ have the meanings given in the definition of formula (I), may be prepared by sequential transformation from a compound of formula (44), in which Z is carboxy, to the corresponding intermediate acid halide of formula (47) such as an acid chloride, then followed by reaction of the acid halide with ammonia or an appropriate alkylamine, dialkylamine or alkyl alcohol. The chlorination can be achieved by reacting the acid with a chlorinating agent such as thionyl chloride, hydrogen chloride, oxalyl chloride, phosphorous trichloride, phosphorous pentachloride or triphenylphosphine in carbon tetra-chloride in the presence of a base as catalyst such as pyridine or triethylamine in an inert solvent such as dichloromethane, ethyl ether, acetonitrile, carbon tetrachloride or tetrahydrofuran at a reaction temperature from about −20° C. to about 150° C. The preferred conditions are thionyl chloride in dichloromethane at reflux temperature. The reaction between the acid halide and the appropriate amine or alcohol can be carried out in an inert solvent such as dichloromethane, chloroform, toluene, acetonitrile or tetrahydrofuran at a reaction temperature from about −20° C. to about 120° C., preferably at the temperature from about −20° C. to about room temperature.

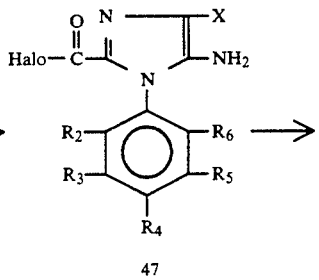

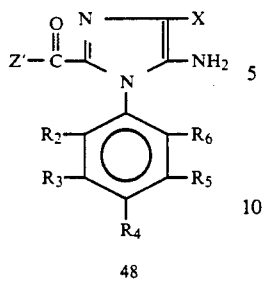

48

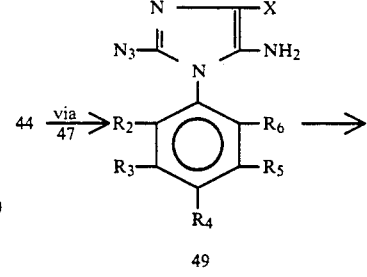

44 $\xrightarrow[47]{via}$ 49 →

Method XVIII

A compound of formula (Ib), in which Z is amino, alkylamino, dialkylamino or trialkylammonium salt, Y is amino or protected amino, and X, $R_2$, $R_3$, $R_4$, $R_5$ and $R_6$ have the meaning given in the definition of formula (I), may be synthesized from a compound of formula (44), in which Z is carboxyl, by the method of the Curtius reaction or a modification thereof such as the Yamada modification. By the conventional Curtius rearrangement, the desired amino derivative may be obtained by a sequential transformation from an acyl halide of formula (47) to an azide of formula (49) by treating the acyl halide with sodium azide or tetramethylguanidinium azide which can then be pyrolyzed into its corresponding isocyanate (50). The isocyanate (50) can then be hydrolyzed into the corresponding amine (51) in which Z is amino. By the Yamada modification, the reaction may be accomplished by treating an acid of formula (44), in which Z is carboxyl, with diphenylphosphoryl azide in the presence of a base such as triethylamine in an inert solvent such as toluene, benzene or tetrahydrofuran at a reaction temperature from about 0° C. to about 150° C. to give the isocyanate intermediate (50) which can then be hydrolyzed with water to afford the compound of the formula (51). A representative procedure is given in Shioro et. al. *J. Am. Chem. Soc.* 1972, 94, 6203. The corresponding compound of formula (Ib), wherein Z is alkylamino, dialkylamino or trialkylammonium salt, namely (52), can be conveniently prepared by monoalkylation, dialkylation and trialkylation using a alkylating agent such as an alkyl iodide or dialkyl sulfate in an inert solvent such as acetonitrile, tetrahydrofuran or dimethoxyethane at a reaction temperature from about 0° C. to about 160° C. optionally in the presence of a base such as potassium carbonate or triethylamine. Alternatively, for methylation of the compound which Z is amino, an Eschweiler-Clark Reaction may be utilized to achieve the desired N-methylation. This reductive methylation can be conveniently conducted by reacting an amine of formula (51) with formaldehyde and formic acid. The procedure is similar to that reported by H. T. Clark et. al. *J. Am. Chem. Soc.*, 55, 4571, 1933.

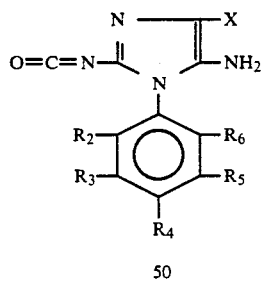

50

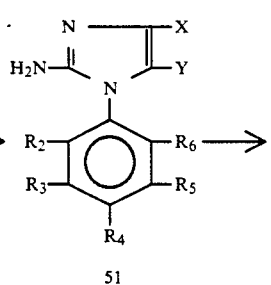

50 → 51 →

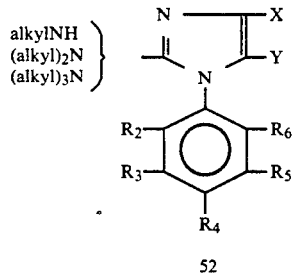

52

Method XIX

A compound of formula (Ib), in which Z is alkoxycarbonylamino, alkylaminocarbonylamino, dialkylaminocarbonyl- amino, Y is amino or protected amino, and X, $R_2$, $R_3$, $R_4$, $R_5$ and $R_6$ have the meanings given in the general definition of formula (I), may be conveniently prepared by a two step sequence involving the first step of converting a compound of formula (51), in which Z is amino, into its corresponding chlorocarbonylamino or isocyanate intermediate by a treatment with phosgene. The reaction can be carried out in an inert organic solvent such as toluene, dichloromethane or tetrahydrofuran at a reaction temperature from about −15° C. to about 100° C., preferably from about −15° C. to about 50° C. The second step is to react the chlorocarbonylamino or isocyanate intermediate compound with an appropriate alkyl alcohol, alkylamine or dialkylamine. The reaction can be carried out in an inert organic solvent such as a halogenated alkane, toluene,

Method XX

A compound of formula (Ib), in which Z is alkoxyalkylideneimino, Y is amino or protected amino, and X, $R_2$, $R_3$, $R_4$, $R_5$ and $R_6$ have the meanings given in the definition of formula (I), can be prepared by reacting a compound of formula (51), in which Z is amino, with an appropriate alkyl orthoformate. The catalyst, solvent and conditions for the transformation are similar to that described for the preparation of compounds of formula (3) from (2) in Method I. For a compound in which Y is an amino group, an appropriate protection group may be introduced before the transformation is carried out.

Method XXI

A compound of formula (Ib), in which Z is alkylcarbonylamino, haloalkylcarbonylamino or arylcarbonylamino group, Y is amino or protected amino, and X, $R_2$, $R_3$, $R_4$, $R_5$ and $R_6$ have the meanings given in the definition of formula (I), can be conveniently prepared from a compound of formula (51), in which Z is amino, by a reaction with an appropriate alkyl, haloalkyl or aryl carbonyl halide, such as acetyl chloride, chloroacetyl chloride, benzoyl chloride or toluoyl chloride in a suitable solvent, such as dichloromethane, ethyl ether or tetrahydrofuran, optionally in the presence of an acid acceptor such as pyridine or triethylamine, at a reaction temperature from about $-10°$ C. to about $100°$ C., preferably from about $-10°$ C. to about $50°$ C.

Method XXII

An intermediate compound of the formula (Ib), namely formula (53), in which Z is hydroxymethyl, Y is amino or protected amino, and X, $R_2$, $R_3$, $R_4$, $R_5$ and $R_6$ have the meanings given in the definition of formula (I), may be prepared by reduction of a compound of the formula (42), in which Z is formyl. The reduction can be conducted with a reducing agent such as lithium aluminum hydride, sodium borohydride, aluminum isoproxide, borane or substituted borane or another metal hydride in a suitable aprotic or protic solvent. For a more reactive hydride, e.g. lithium aluminum hydride, the reaction may be conducted in an inert solvent such as tetrahydrofuran, ethyl ether or dimethoxyethane at a reaction temperature from about $-10°$ C. to about $120°$ C., preferably at a temperature from about $20°$ C. to about $100°$ C. For a milder hydride, such as sodium borohydride, the reaction may be conducted in an alcohol such as methanol at a temperature from about $-10°$ C. to about $100°$ C., preferably from about room temperature to about $75°$ C.

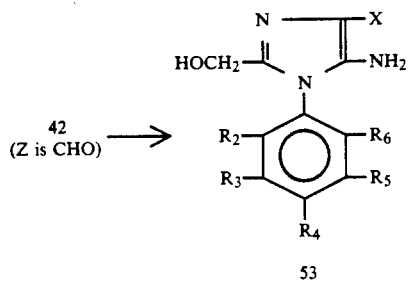

Method XXIII

A compound of formula (Ib), i.e. (54), wherein Z is haloalkyl, particularly chloromethyl, fluoromethyl, bromomethyl or iodomethyl, Y is amino or protected amino, and X, $R_2$, $R_3$, $R_4$, $R_5$ and $R_6$ have the meanings given in the definition of formula (I), can be prepared from the intermediate compound of formula (53), in which Z is hydroxymethyl, by using an appropriate chlorinating, fluorinating or brominating agent. For chlorination, the reaction may be carried out with reagents such as thionyl chloride, phosphorous trichloride, phosphorous pentachloride, phosphorous oxychloride in dichloromethane or ethyl ether at a reaction temperature from about $-20°$ C. to about $100°$ C. The reaction can be carried out optionally in the presence of an acid acceptor such as triethylamine or pyridine. For fluorination, the reaction can be conducted with dialkylaminosulfur trifluoride in a solvent such as acetonitrile, dichloromethane or glyme at a reaction temperature from about $-20°$ C. to about $100°$ C. A more preferable condition is using diethylaminosulfur fluoride in acetronitrile at room temperature. A representative procedure is given in, W. J. Middletown, J. Org. Chem., (1975), 42, 5, 574. Other fluorinating reagents may also be used, such as sulfur trifluoride, bis(dialkylamino)sulfur trifluoride or sodium or potassium fluoride in a polyhydrogen fluoride-pyridine solution, which procedure is that reported by Olah and Welch, Synthesis, 653, (1974). For bromination, the reaction may be conducted with a brominating agent such as bromine, N-bromosuccinimide, phosphorous tribromide or hydrogen bromide in an inert solvent such as dichloromethane or ethyl ether at a temperature from about $-20°$ C. to about $100°$ C. For iodidation, the reaction may be performed with hydrogen iodide in an inert solvent such as dichloromethane at a reaction temperature from about $-20°$ C. to about $100°$ C.

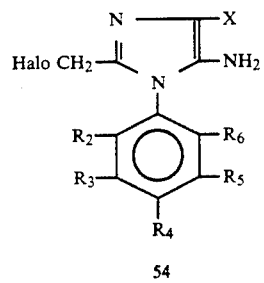

Method XXIV

A compound of formula (Ib), in which Z is cyanoalkyl, particularly cyanomethyl, Y is amino or protected amino, and X, Y, $R_2$, $R_3$, $R_4$, $R_5$ and $R_6$ have the meanings given in the definition of formula (I), may be prepared from the corresponding halomethyl compound of formula (54), the preparation of which is described above in Method XXIII, by cyanation with a metal cyanide such as copper cyanide, an alkali cyanide or alkaline metal cyanide such as sodium cyanide or potassium cyanide in a suitable solvent such as dimethylformamide, tetrahydrofuran, acetonitrile, diglyme or tetramethylenesulfone at a reaction temperature from about room temperature to about $250°$ C., preferably from about $70°$ C. to about $150°$ C.

Method XXV

A compound of formula (Ib), in which Z is alkenyl or alkynyl, Y is amino or protected amino, and X, $R_2$, $R_3$, $R_4$, $R_5$ and $R_6$ have the meanings given in the definition of formula (I), may be prepared from formula (42), in which Z is formyl, by employing the Wittig reaction or modifications thereof such as the Wadsworth-Emmons (Horner) Modification. The Wittig reagents may be those which are commercially available or those that can be prepared according to well-known literature procedures. The reaction may be conducted in inert solvents such as tetrahydrofuran, dimethoxyethane or toluene at a reaction temperature from about $-30°$ C. to about $180°$ C. Examples of the Wittig reagents that may be employed are an alkyl triphenyl phosphonium halide such as methyl triphenylophosphonium iodide, isopropyl triphenylphosphonium iodide, allyl triphenyl phosphonyl halide or trialkyl phosphonoacetate. A representative example of the procedure for the Wittig reaction is given in Org. Synth. Coll. Vol. 5, 751 (1973). In case that the Wittig reagent employed contains an alkynyl group such as propargyl triphenylphosphonium bromide, which is commercially available, the compound obtained is where Z is an alkynyl substituent. Additionally, the alkynyl analog, formula (55), with alkynyl directly attached to 2-carbon of the imidazolyl ring, can be introduced from the corresponding Z is halogen analog, such as an iodo analog, by a reaction with a copper acetylide using a procedure similar to that described by R. E. Atkinson et. al., Chem. Soc. (C), 2173, 1969 or the references cited therein.

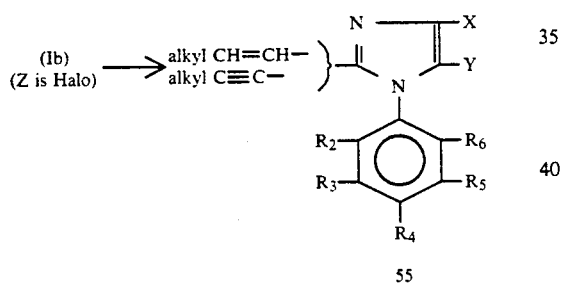

55

Method XXVI

A compound of formula (Ib), in which Z is alkylcarbonyl or haloalkylcarbonyl, Y is amino or protected amino, and X, $R_2$, $R_3$, $R_4$, $R_5$ and $R_6$ have the meanings given in the definition of formula (I), can be prepared by an alkylation of a compound of formula (42), in which Z is formyl, with a carbanion such as a Grinard Reagent or a metal alkane such as a lithium alkane in an inert solvent such as tetrahydrofuran, ethyl ether, hexane, dimethoxyethane or a combination thereof at a reaction temperature from about $-70°$ C. to about $100°$ C. to give the intermediate, (56), with a secondary hydroxy alkyl methyl at the Z position. This intermediate is then subsequently oxidized with an oxidizing agent such as manganese dioxide, dichromate, permanganate or molecular oxygen in a suitable solvent such as dichloromethane, alcohol, acetone or water at a reaction temperature from about $-10°$ C. to about $175°$ C., preferably from about $4°$ C. to about $50°$ C., to the compound of formula (57). Specifically, the methylcarbonyl analog at the Z position may be alternatively prepared in one step by treating a compound of formula (42), in which Z is formyl, with AlMe$_2$(BHT) (OEt)$_2$ in a suitable solvent such as toluene at a reaction temperature from about $-20°$ C. to about $55°$ C., preferably at about room temperature. A representative procedure is reported in M. B. Power and A. R. Barron Tet. Let., 31, 3, 323, 1990 and references cited therein. The corresponding compound in which Z is haloalkylcarbonyl can be conveniently prepared by the typical method of halogenating a ketone, such as using bromine, chlorine, iodine, N-chlorosuccinimide or N-bromosuccinimide to provide a compound wherein Z is haloalkylcarbonyl.

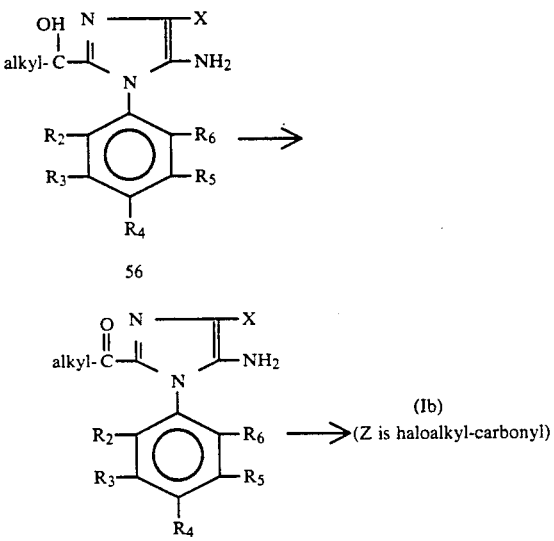

Method XXVII

A compound of formula (Ib), in which Z is alkylsulfenyl, haloalkylsulfenyl, alkylsulfinyl, haloalkylsulfinyl, alkylsulfonyl, or haloalkylsulfonyl, Y is amino, and X, $R_2$, $R_3$, $R_4$, $R_5$ and $R_6$ are those defined for the definition of formula (I), can be prepared by the following sequential steps:

a) A useful intermediate compound of formula (Ib), i.e. (58), in which Z is thiocyano, Y is amino or protected amino, and X, $R_2$, $R_3$, $R_4$, $R_5$ and $R_6$ have the meanings given in the definition of formula (I), can be prepared by reacting a compound of formula (Ia), in which Z is hydrogen, with a mixture of bromine and a metal thiocyanate in a suitable solvent such as methanol or ethanol at a temperature from about $-78°$ C. to about $100°$ C., preferably from about $-78°$ C. to about room temperature.

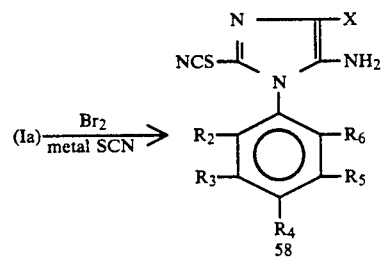

b) A compound of formula (IB), namely (59), in which Z is alkylsulfenyl or haloalkylsulfenyl, Y is amino or protected amino, and X, $R_2$, $R_3$, $R_4$, $R_5$ and $R_6$ have the meanings given in the definition of formula (I), can be prepared from a compound of formula (58), in which Z is thiocyano, by treatment with an alkylating agent, in a suitable solvent such as an alcohol, acetonitrile, tetrahydrofuran, dimethoxyethane or water with or without the presence of a base such as an alkali hydroxide or a alkali carbonate at a reaction temperature from about $-20°$ C. to about $150°$ C., preferably from about $0°$ C. to about $85°$ C.

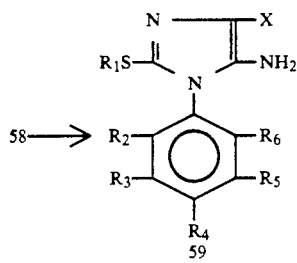

c) A compound of formula (Ib), in which Z is alkylsulfinyl haloalkylsulfinyl, alkylsulfonyl or haloalkylsulfonyl, Y is amino or protected amino, and X, $R_2$, $R_3$, $R_4$ and $R_5$ have the meanings given in the definition of formula (I), can be prepared from a sulfenyl compound of formula (59) by treatment with a stoichiometric amount of an appropriate oxidizing agent. The procedures of these transformations are similar to those described for the oxidation of compounds of formula (8) to (9) in Method I.

d) Additionally, an intermediate compound of formula (Ib), i.e. (60), in which Z is thiocyano, Y is hydrogen, and X, $R_2$, $R_3$, $R_4$, $R_5$ and $R_6$ are as defined in formula (I), can be prepared by deamination of a compound of formula (58), in which Z is thiocyano, Y is hydrogen and X and $R_2$ to $R_6$ are as defined in formula (I), following the procedure similar to that described in Method I. This can then be further alkylated to an alkyl or haloalkyl sulfenyl compound and then oxidized by the above procedure to give a compound of formula (I), wherein Y is hydrogen, Z is as defined in parts b) or c) above, and X, $R_2$, $R_3$, $R_4$, $R_5$ and $R_6$ are as defined for formula (I).

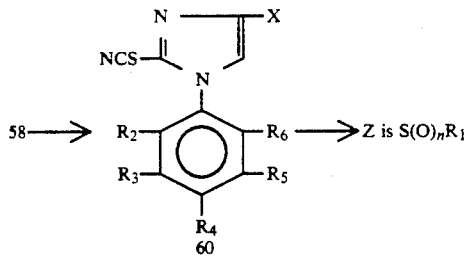

e) Furthermore, a compound of formula (Ib), in which Z is haloalkylsulfenyl, and X, Y, $R_2$, $R_3$, $R_4$, $R_5$ and $R_6$ are as defined above may be prepared from a compound of formula (58) or (60), wherein Z is thiocyano, via the corresponding disulfide. According to the procedures similar to those described in Method XLIV below. These compounds may then be oxidized to the corresponding sulfoxide (n=1) or sulfone (n=2) compounds, in which Z is $S(O)_nR_1$ as previously defined, according to methods as described above, i.e. Method I.

Method XXVIII

A compound of formula (Ib), in which Z is sulfhydryl or salts thereof, Y is amino or protected amino, and X, $R_2$, $R_3$, $R_4$, $R_5$ and $R_6$ have the meanings given in the definition of formula (I), can be prepared by a free radical-promoted sulfur-carbon cleavage of a compound of formula (58), wherein Z is thiocyano. The reaction may be conducted with a free radical promoter such as potassium ferricyanide in a suitable solvent such as an alcohol, tetrahydrofuran, water or a mixture thereof, in an appropriate proportion, under neutral or basic conditions at a reaction temperature from about $-10°$ C. to about $180°$ C. A preferred procedure is to carry out the reaction using potassium ferricyanide in methanol and water in the presence of potassium hydroxide at refluxing conditions.

Alternatively, an analogous compound of formula (60), wherein Z is thiocyano, Y is hydrogen, and X and $R_2$ to $R_6$ are as defined in formula (I), can be converted by procedures similar to those above to a compound wherein Z is sulfhydryl or salts thereof.

Methods XXIX to XLIII Generalization

The following Methods XXIX to XLIII detail specific procedures for introducing a Y substituent into a particular compound of formula (Ib) to provide a compound of the invention of formula (I).

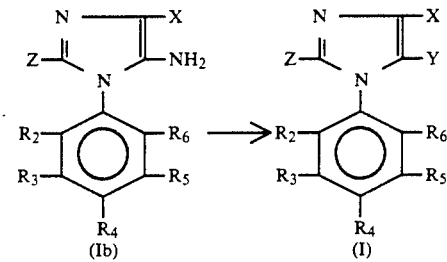

Method XXIX

A compound of formula (I), in which Y is alkoxycarbonylamino, alkylaminocarbonylamino, dialkylaminocarbonylamino, and X, Z, $R_2$, $R_3$, $R_4$, $R_5$ and $R_6$ have the meanings given in the definition of formula (Ib), may be prepared from a compound of formula (Ib), in which Y is amino and the other substituents are defined as above by procedures similar to those described in Method XIX.

Method XXX

A compound of formula (I), in which Y is alkoxyalkylideneimino and X, Z, $R_2$, $R_3$, $R_4$, $R_5$ and $R_6$ have the meanings given in the definition of formula (I), can be prepared from a corresponding compound of formula (Ib), wherein Y is amino, by a procedure similar to that described in Method XX.

Method XXXI

A compound of formula (I), in which Y is alkylcarbonylamino, haloalkylcarbonylamino or arylcarbonylamino group and X, Z, $R_2$, $R_3$, $R_4$, $R_5$ and $R_6$ have the meanings given in the definition of formula (I), may be prepared from the corresponding compound of formula (Ib), in which Y is amino by a sequence of procedures similar to that described in Method XXI.

Method XXXII

A compound of formula (I), in which Y is sulfhydryl or salts thereof, and X, Z, $R_2$, $R_3$, $R_4$, $R_5$ and $R_6$ have the meanings given by the definition of formula (I), can be prepared by the sequence described below:

a) The intermediate compound, in which Y is thiocyano and X, Z, $R_2$, $R_3$, $R_4$, $R_5$ and $R_6$ have the meanings given in the definition of formula (I), can be prepared from a compound of formula (I), i.e. (61) herein below, in which Y is hydrogen, optionally obtained via Method I, and X, Z, $R_2$, $R_3$, $R_4$, $R_5$ and $R_6$ are as defined above. The transformation may be achieved by a procedure similar to that described in Method XXVII.

b) The thiocyano intermediate compound obtained by the method described above can be converted into the corresponding compound of formula (I), wherein Y is sulfhydryl and salts thereof, using a procedure similar to that described in Method XXVIII.

Method XXXIII

A compound of formula (I), i.e. (62), in which Y is alkyl, haloalkyl, alkenyl, alkynyl, cyanoalkyl or formyl and X, Z, $R_2$, $R_3$, $R_4$, $R_5$ and $R_6$ are defined in the definition of formula (I), except those base-sensitive in nature, can be prepared from a compound of formula (61), in which Y is hydrogen, by treatment with a strong base, preferably an organic base such as lithium diisopropylamide, n-butyl lithium or sec-butyl lithium in an appropriate solvent, such as tetrahydrofuran or ethyl ether at a reaction temperature from about −75° C. to about room temperature, followed by quenching the metal carbanion, with an appropriate electrophile, e.g. alkyl halide or N-formyl piperidine, to obtain the corresponding substituent at the Y position. This method of synthesis is generally known as a directed ortho metalation reaction. Examples of the procedure are described by V. Snieckus in Bull. Soc. Chim. Fr., 1988, (1), 67–78 and references cited therein.

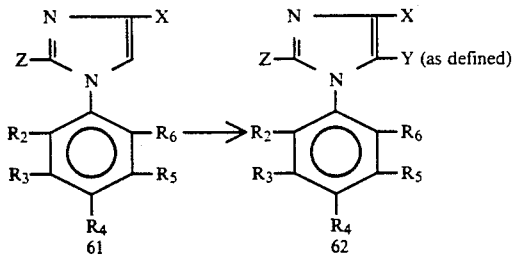

Method XXXIV

A compound of formula (I), in which Y is a carboxylic group or a carboxylate salt and X, Z, $R_2$, $R_3$, $R_4$, $R_5$ and $R_6$ have the meanings given in the definition of the invention, can be prepared from a compound of formula (I), in which Y is formyl and X, Z, $R_2$, $R_3$, $R_4$, $R_5$ and $R_6$ are defined as above, by a procedure similar to that described in Method XIV.

Method XXXV

A compound of formula (I), in which Y is cyano and X, Z, $R_2$, $R_3$, $R_4$, $R_5$ and $R_6$ have the meanings given in the definition of formula (I), can be prepared from a compound of formula (I), in which Y is a carboxylic group and the other substituents are as defined above, by a procedure similar to that described in Method XV or Method XVI.

Method XXXVI

A compound of formula (I), in which Y is aminocarbonyl, alkylaminocarbonyl, dialkylaminocarbonyl or alkoxycarbonyl and X, Z, $R_2$, $R_3$, $R_4$, $R_5$ and $R_6$ have the meanings given in the definition of formula (I), can be prepared from a compound of formula (I), in which Y is carboxyl and X, Z, $R_2$, $R_3$, $R_4$, $R_5$ and $R_6$ are as defined above, by a procedure similar to that described in Method XVII.

Method XXXVII

A compound of formula (I), in which Y is alkylamino, dialkylamino or trialkylammonium salt and X, Z, $R_2$, $R_3$, $R_4$, $R_5$ and $R_6$ have the meanings given in the definition of formula (I), can be prepared from a compound of formula (I), i.e. (Ib), in which Y is amino and the other substituents are as defined above, by monoalkylation, dialkylation and trialkylation with an appropriate alkylating agent. The solvent, reaction temperature and alkylating agent may be chosen based on the general procedures described in Method XVIII. For N-methylation, the Eschweiler-Clark reaction may be employed by a procedure similar to that described in Method XVIII.

Method XXXVIII

A compound of formula (I), in which Y is haloalkyl, particularly halomethyl, including fluoro, chloro, bromo and iodoalkyl and X, Z, $R_2$, $R_3$, $R_4$, $R_5$ and $R_6$ have the meanings given in the definitions of formula (I), can be prepared from a compound of formula (I), in which Y is formyl and the other substituents are as defined above, by a sequence of transformations via the corresponding hydroxymethyl intermediate which is then converted into the halomethyl analogs. The sequence and procedures of the transformations are similar to those described in Method XXII and XXIII.

Method XXXIX

A compound of formula (I), in which Y is alkenyl or alkynyl and X, Z, $R_2$, $R_3$, $R_4$, $R_5$ and $R_6$ have the meanings given in the definition of formula (I), can be prepared from a compound of formula (I), in which Y is formyl (or optionally Y is halogen obtained via Method I) and the other substituents are as defined above, by a procedure similar to that described in Method XXV.

Method XL

A compound of formula (I), in which Y is alkylcarbonyl or haloalkylcarbonyl and X, Z, $R_2$, $R_3$, $R_4$, $R_5$ and $R_6$ have the meanings given in the definition of formula (I), can be prepared from the corresponding compound of formula (I), in which Y is formyl, following a procedure similar to that described in Method XXVI. The transformation is achieved via an intermediate which bears a secondary hydroxyalkylmethyl at the Y position or by a direct transformation using $AlMe_2(BHT)(OEt)_2$ to give the compound in which Y is alkylcarbonyl, followed by halogenation procedures as in Method XXVI to give the compound in which Y is haloalkylcarbonyl.

Method XLI

A compound of formula (I), in which Y is aminosulfonyl, alkylaminosulfonyl or dialkylaminosulfonyl and X, Z, $R_2$, $R_3$, $R_4$, $R_5$ and $R_6$ have the meanings given in the definition of formula (I), can be prepared from a compound of formula (I), i.e. (61), wherein Y is hydrogen, optionally obtained via Method I, and X, Z, $R_2$, $R_3$, $R_4$, $R_5$ and $R_6$ have the meanings herein above defined by the following sequence:

a) An intermediate compound of formula (64), in which Y is chlorosulfonyl and X, Z, $R_2$, $R_3$, $R_4$, $R_5$ and $R_6$ have the meanings given in the definition of formula (I), may be prepared by treating a compound of formula (61), in which Y is hydrogen, optionally obtained via Method I, with an alkyl lithium, such as n-butyllithium or sec-butyllithium in an inert solvent such as ethyl ether, hexane, tetrahydrofuran or a mixed solvent combination thereof at a temperature from about $-78°$ C. to about room temperature, preferably from about $-78°$ C. to about $-30°$ C., followed by quenching the carbanion (63) with sulfuryl chloride in an inert solvent, such as hexane or ethyl ether at a temperature from about $-78°$ C. to about room temperature, preferably from about $-78°$ C. to about $-20°$ C. A similar procedure is reported by S. N. Bhattacharya, et. al., J. Chem. Soc. (C), 1968, 1265.

Alternatively, the carbanion intermediate (63) may be prepared by a similar method from a compound of formula (I), in which Y is a halogen, optionally obtained via Method I, such as chlorine, bromine or iodine, by treatment with magnesium or alkyl lithium in an inert solvent at a temperature similar to that described above.

b) The compound of formula (65), in which Y is aminosulfonyl, alkylaminosulfonyl or dialkylaminosulfonyl, can be prepared by reacting the chlorosulfonyl intermediate (64) with ammonia or an appropriate alkylamine or dialkylamine in a suitable solvent such as a halogenated alkane, ether, tetrahydrofuran or hexane at a reaction temperature from about $-50°$ C. to about $50°$ C., preferably from about $-20°$ C. to about room temperature.

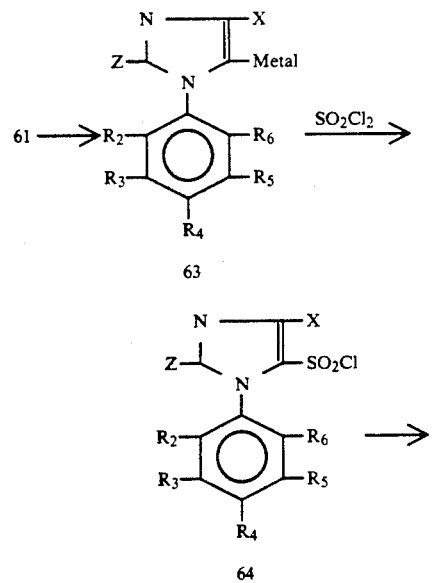

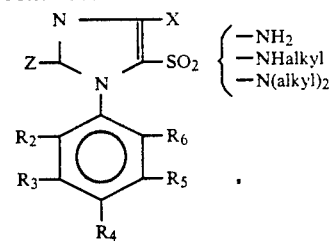

Method XLII

A compound of formula (I), in which Y is nitro or amino, and X, Z, $R_2$, $R_3$, $R_4$, $R_5$ and $R_6$ have the meanings given in the definition of formula (I), can be prepared by a direct nitration from a compound of general formula (I), i.e. (61), wherein Y is hydrogen, optionally obtained via Methods I, and X, Z, $R_2$, $R_3$, $R_4$, $R_5$ and $R_6$ are as defined above. The nitration reaction and subsequent reduction to the compound wherein Y is amino may be conducted by a procedure similar to that described in Method VIII.

Method XLIII

A compound of formula (I), in which Y is hydroxy and salts thereof, alkoxy or haloalkoxy and X, Z, $R_2$, $R_3$, $R_4$, $R_5$ and $R_6$ have the meanings given in the definition of formula (I), may be prepared from a compound of formula (I), wherein Y is halogen, optionally obtained via Methods I, and the other groups are as defined above, by converting the halo compound into the corresponding Grignard reagent or lithium carbanion, followed by treatment with oxodiperoxymolybdenum(-pyridine)-(hexamethylphosphoric triamide) (MoOPH) to a compound wherein Y is hydroxyl, using a procedure similar to that described in Method IB. The corresponding alkoxy or haloalkoxy compound can then be conveniently prepared utilizing a procedure similar to that described in Method IB.

Method XLIV

A compound of formula (I), wherein X is particularly alkylsulfenyl, haloalkylsulfenyl, alkylsulfinyl, haloalkylsulfinyl, alkylsulfonyl or haloalkylsulfonyl and Y, Z, $R_2$, $R_3$, $R_4$, $R_5$ and $R_6$ have the meanings of the definition of formula (I), can be alternatively prepared by the following procedures starting from the compound in which X is hydrogen to give intermediate, wherein X is thiocyano, (71), or X is chlorosulfonyl, (67). Either of these intermediates may be converted to the corresponding disulfide intermediate which is then converted to the sulfenyl compound, in which Y is $SR_1$ and in which $R_1$ is as previously defined, which in turn may be oxidized to the corresponding sulfoxide or sulfone, X is $S(O)_nR_1$, in which n is 1 or 2.

a) An intermediate of the formula (67), in which X is chlorosulfonyl, Y, Z, $R_2$, $R_3$, $R_4$, $R_5$, and $R_6$ have the meanings defined in the definition of formula (I), can be prepared from an intermediate compound of the formula (Ic), namely (66), in which X is hydrogen and Y, Z, $R_2$, $R_3$, $R_4$, $R_5$ and $R_6$ are defined herein above, by treatment with chlorosulfonic or dichlorosulfonic acid. The reaction can be carried out in the presence of organic solvents such as methylene chloride, chloroform, carbon tetrachloride or dimethylformamide or using chlorosulfonic acid as solvent at a reaction temperature from about −10° C. to about 160° C. A representative procedure for chlorosulfonation of an aromatic compound is reported in J. March, "Advanced Organic Chemistry", McGraw-Hill publ. (1968), p. 402.

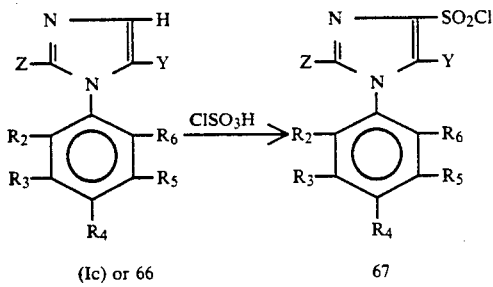

(Ic) or 66              67 b) An intermediate disulfide compound of the formula (68), in which X is disulfide and the definitions of Y, Z, R$_2$, R$_3$, R$_4$, R$_5$ and R$_6$ are those given for the definition of formula (I), can be prepared from the compound of the formula (67) by treatment with a reducing agent, such as triphenylphosphine, in the presence of an organic solvent, such as tetrahydrofuran, dichloromethane or toluene at a reaction temperature from about −10° C. to about 120° C. A representative example of a procedure for the reduction to p-tolyldisulfide is reported in *J. Org. Chem.* 1980, 45, 4792. Alternatively, disulfenylation can be effected using a metal carbonyl such as hexacarbonylmolybedium in anhydrous tetramethyurea. The procedure of this reaction is reported by H. Alper, Angew. Chem. Internat. Edit, 8, 677, 1969.

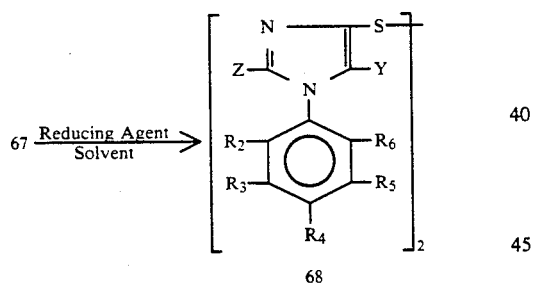

c) A compound of the formula (I), namely (70), wherein the definition of Y, Z, R$_2$, R$_3$, R$_4$, R$_5$ and R$_6$ are those given for the definition of formula (I), and X is haloalkylsulfenyl, preferably perhaloalkylsulfenyl, R$_7$S, in which R$_7$ is CFR$_8$R$_9$ and R$_8$ and R$_9$ are F, Cl, Br or a perfluoroalkyl group, can be prepared by the reaction of a compound of the formula (68) and a perhaloalkane compound of the formula (69), Halo-CFR$_8$R$_9$, wherein Halo is Cl, Br or I, R$_8$ is F, Cl or Br, and R$_9$ is F, Cl, Br or a perfluoroalkyl group, with a reducing agent which can promote the formation of the free radical CFR$_8$R$_9$ (from Halo-CFR$_8$R$_9$). The reducing agent is preferably chosen from a metal consisting of zinc, aluminum, cadmium, manganese or a compound with an oxide of sulfur, e.g., a dithionite or a hydroxymethylsulfinate. The alkaline dithonite, alkaline earth or the metal dithionite corresponds to the formula M$_n$(S$_2$O$_4$), in which n can be 1 or 2 depending upon the valence of the metal M. When a dithionite or a hydroxymethylsulfinate is used, a base is needed. The base can be chosen from among an alkaline hydroxide, alkali earth hydroxide, ammonia, alkylamine, triethylbenzylammonium or the salt of weak acids such as disodium phosphate, sodium metabisulfite, sodium hydrogen sulfite or sodium borate. The solvents used for the reaction are those which can solubilize the dithionite or the hydroxymethylsulfinate, and the compounds (68) and (69). Useful solvents are acetonitrile, dimethylformamide, formamide, dimethylacetamide, hexamethylphosphoramide, N-methylpyrrolidone, dimethylsulfoxide or sulfolane. The reaction temperature is from about 10° C. to about 100° C. Typical procedures are similar to those reported by A. Maggiolo, J. Am. Chem. Soc., 1951, 5815 and by P. W. Feit, Acta. Chem. Scan., 16, 1962, 297. The reaction is represented by the following equation:

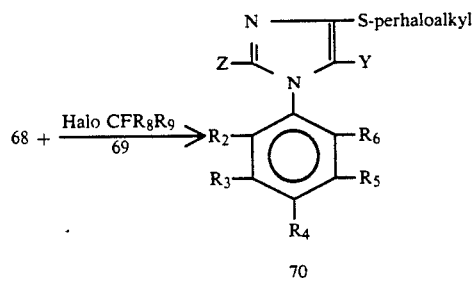

d) The intermediate compound of formula (I), namely (71), in which X is cyanothio and Y, Z, R$_2$, R$_3$, R$_4$, R$_5$ and R$_6$ have the meanings given in the definition of formula (I), may be prepared from a compound of formula (Ic), i.e. (66), by treatment with bromine and an alkali thiocyanate such as potassium thiocyanate in a suitable solvent such as methanol at a temperature from about −78° C. to about room temperature. The solvent should be inert to and capable of solvolyzing the reactants.

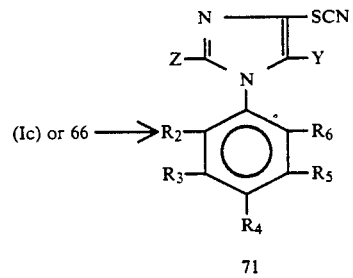

e) Alternatively, the compound of formula (70), wherein X is haloalkylsulfenyl, preferably perhaloalkylsulfenyl, may be prepared by a sequence of oxidation of a compound of formula (71) to form an intermediate disulfide compound of formula (68), which can then be converted into its corresponding haloalkylsulfenyl compound of formula (70). The oxidation can be achieved using an oxidizing agent such as hydrogen peroxide in the presence of an alkali hydroxide, such as sodium hydroxide, or an amine such as ammonia in a suitable solvent, such as an alcohol, water, tetrahydrofuran, a halogenated alkane or mixed solvent thereof, at a reaction temperature from about −70° C. to about 55° C. Typical procedures are reported by A. Maggiolo, J. Am. Chem. Soc., 1951, 5815 and by P. W. Feit, Acta. Chem. Scan., 16, 1962, 297. The haloalkylsulfenyl compound of formula (70) can be prepared by reacting the disulfide intermediate compound with an appropriate perhaloalkane, optionally in the presence of a reducing agent such as a metal consisting of zinc, aluminum, cadmium or manganese.

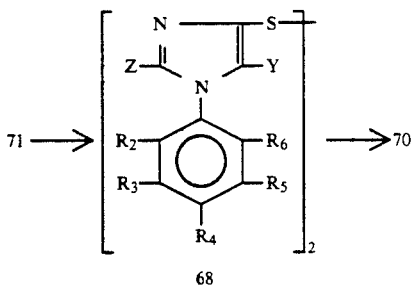

68 f) A further compound of formula (I), i.e. (72), wherein X is alkylsulfenyl or haloalkylsulfenyl and Y, Z, $R_2$, $R_3$, $R_4$, $R_5$ and $R_6$ are as defined by formula (I), can be prepared by treating a compound of formula (71) with an appropriate alkyl halide, $R_1$ Halo, in which $R_1$ is alkyl or haloalkyl, preferably an alkyl iodide or an alkyl bromide in a suitable solvent such as an alcohol, preferably the corresponding alkyl alcohol, in the presence of a base catalyst such as an alkali hydroxide or alkali carbonate at a reaction temperature from about $-20°$ C. to about 75° C.

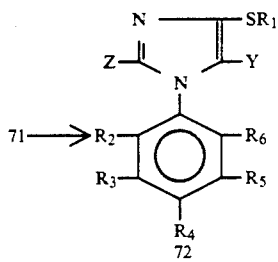

72 g) A compound of formula (I), wherein X is alkylsulfinyl, haloalkylsulfinyl, alkylsulfonyl or haloalkylsulfonyl and Y, Z, $R_2$, $R_3$, $R_4$, $R_5$ and $R_6$ are as defined in formula (I), can be prepared from a compound of formulae (70) or (72) by the oxidation procedures described, for example in Method I.

Method XLV

Still other processes to make compounds of formula (I), which are contemplated within the present invention include, for example, an aromatic nucleophilic displacement reaction of a halogen atom on the phenyl ring by an alkylthiol or anion thereof. In this way, compounds of formula (I) (e.g., compounds of formulae (6), (7), (8), (9) and (18) provide other new compounds of formula (I), wherein one or more of $R_2$ to $R_6$ is an alkylsulfenyl group, which may be further oxidized to the corresponding sulfoxide or sulfone, in a manner similar to that of oxidation of (8) to (9) in Method (I). This reaction, as appropriate, may also be conducted with starting materials or intermediates in the above described processes to introduce into said compounds an alkylsulfenyl, alkylsulfinyl or alkylsulfonyl group on the phenyl ring prior to formation of compounds of formula (I) of the invention.

This process may be exemplified by the following equation in which a compound of formula (73) is reacted to give a compound of formula (74). Compounds of formulae (73) and (74) are preferred examples of compounds of the invention of formula (I) or (II) wherein: $R_3$ and $R_5$ are each a hydrogen atom; $R_2$ is a halogen atom (e.g., F. Cl or Br) in the case of compound (73) or in the case of compound (74), $R_2$ is an alkylsulfenyl group, wherein the alkyl moiety is a linear or branched chain containing one to four carbon atoms; $R_4$ and $R_6$ are as defined in formula (I), preferably electron withdrawing groups such as trifluoromethyl, cyano, nitro or a halogen atom; and X, Y and Z are as defined in formula (I) or (II).

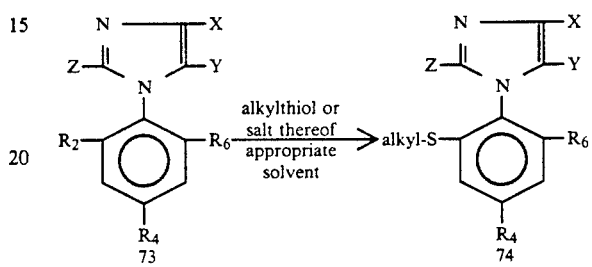

73    74

The process is preferably conducted in a solvent which is capable of solvolyzing the 1-phenylimidazole compound and the alkylthiol or thiolate salt thereof, which is, for example, an alkali metal, alkaline earth metal or tetraalkylammonium salt, but preferably a sodium or potassium salt. Preferred solvents are ethers (e.g., tetrahydrofuran or diglyme), alcohols (e.g., methanol or ethanol), amines (e.g., triethylamine or pyridine), aprotic solvents such as dimethylformamide, or water or combinations of these solvents. The more preferred solvent systems are water-tetrahydrofuran or water-tetrahydrofuran-methanol. The reaction is generally conducted at a temperature between about $-20°$ C. and about 180° C., preferably between about 0° C. and about 120° C.

Method Generalizations

The above methods or processes of synthesis are not to be construed as limiting and therefore, compounds of the present invention, as well as intermediates and starting materials (particularly the anilines), can be prepared by application or adaptation of synthesis methods, which are apparent to one skilled in the art, and are commonly known, used or described in the chemical literature. In this regard, it is understood that, for example, the sequence of the synthetic chemical steps may be performed in a different order as appropriate, suitable protecting groups may be employed, and substitutent groups may be incorporated when convenient. In the description of process methods, when symbols appearing in a formula are not specifically defined, it is also to be understood that they are "as herein before defined" in accordance with the first definition of each symbol in this specification.

In an overall/global manner the foregoing Methods of synthesis may be represented by the following processes of the invention which are described as follows:

$P_1$. A process of preparation of a compound of formula (Ia),

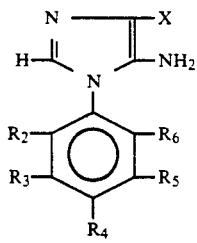

wherein $R_2$, $R_3$, $R_4$, $R_5$ and $R_6$ are as defined for formula (I) and X is alkylsulfenyl, haloalkylsulfenyl, alkylsulfinyl, haloalkylsulfinyl, alkylsulfonyl, haloalkylsulfonyl, haloalkyl or haloalkoxy, wherein a compound of formula (5),

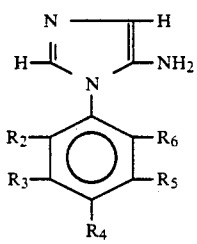

in which amino is optionally protected as required:

a) is first reacted with a sulfenyl halide, $R_1$SHalo in which $R_1$ is alkyl or haloalkyl, in an organic reaction medium, optionally in the presence of an acid acceptor such as a tertiary amine to obtain a compound of formula (Ia), wherein X is alkylsulfenyl or haloalkylsulfenyl, which is then optionally oxidized by known methods such as by a peroxide, to obtain a compound of formula (Ia), wherein X is $S(O)_nR_1$ in which n is 1 or 2 and $R_1$ is as defined above, that is to say X is alkylsulfinyl, haloalkylsulfinyl, alkylsulfonyl or haloalkylsulfonyl;

b) is first reacted with a tris(alkylthio)methane or tris(arylthio)methane in an organic reaction medium in the presence of a Lewis Acid and optionally in the presence of an acid acceptor, then the obtained intermediate compound of formula (10), in which X is bis(alkylthio)methyl or bis(arylthio)methyl is reacted in an organic reaction medium with a suitable alkylnitrite followed by a hydrolysis procedure to obtain an intermediate compound of formula (Ia), in which X is formyl, then is followed by known reduction procedures to give the intermediate compound, in which X is hydroxymethyl, and then is finally halogenated by known procedures to give a compound of formula (Ia), in which X is haloalkyl, more specifically halomethyl;

c) is first formylated by well known procedures such as that of Vilsmeier-Haack and the like to give the compound of formula (Ia), in which X is formyl, then is reacted following the procedures above in part b) to likewise obtain the compound of formula (Ia), in which X is haloalkyl;

d) is reacted by the procedures of part b) or c) above to obtain an intermediate compound of formula (Ia), in which X is formyl, which compound may be optionally oxidized to an intermediate compound of formula (Ia), in which X is carboxyl, then finally the intermediate compound, in which X is formyl, is reacted with a halogenating agent such as diethylaminosulfur trifluoride or the intermediate compound, in which X is carboxyl, is reacted with sulfur tetrafluoride to give a compound of formula (Ia), in which X is haloalkyl, more specifically difluoromethyl or trifluoromethyl; or e) is first halogenated by well known procedures to obtain an intermediate compound, in which X is halogen, from which an organomagnesium or -lithium derivative is prepared, then said organometallic is reacted with oxodiperoxymolybdenum(pyridine)-(hexamethylphosphoric triamide) or a trialkyl borate and an oxidizing agent such as hydrogen peroxide to obtain an intermediate compound of formula (Ia), in which X is hydroxy, then is finally reacted by known haloalkylating procedures to obtain a compound of formula (Ia) in which X is haloalkoxy.

P2. A process of preparation of a compound of formula (Ib),

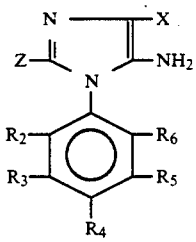

wherein X, $R_2$, $R_3$, $R_4$, $R_5$ and $R_6$ are as defined for formula (I) and Z is aminosulfonyl, alkylaminosulfonyl, dialkylaminosulfonyl, nitro, amino, halogen, alkynyl, alkyl, hydroxy and salts thereof, alkoxy, haloalkoxy, formyl, alkylsulfenyl, haloalkylsulfenyl, alkylsulfinyl, haloalkylsulfinyl, alkylsulfonyl, haloalkylsulfonyl, or sulfhydryl and salts thereof, wherein a compound of formula (Ia),

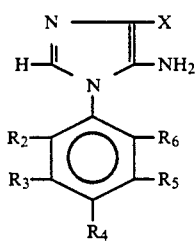

in which X and amino are optionally protected as required:

a) is first reacted with chlorosulfonic or dichlorosulfonic acid to give an intermediate compound, wherein Z is chlorosulfonyl, which compound is reacted with ammonia, an alkylamine or dialkylamine to give a compound of formula (Ib), in which Z is aminosulfonyl, alkylaminosulfonyl or dialkylaminosulfonyl;

b) is halogenated or nitrated by known procedures to give a compound of formula (Ib), in which Z is halogen or nitro, then the compound in which Z is nitro is optionally reduced to Z is amino by known procedures, or optionally the compound, in which Z is halogen, is treated by known procedures with a copper acetylide to give the compound in which Z is alkynyl;

c) is reacted with a strong base such as an organolithium reagent to give an intermediate organometallic carbanion, which is then quenched with an alkylating agent to give a compound of formula (Ib), in which Z is alkyl, or optionally the carbanion is reacted in a manner similar to that described in process $P_{1e}$ to first give a compound of formula (Ib), in which Z is hydroxyl or salts thereof, or then optionally the compound in which Z is hydroxy is converted to a compound wherein Z is alkoxy or haloalkoxy by known alkylation or haloalkylation procedures;

d) is reacted by formylation procedures similar to those described in process P₁b or P₁c, wherein the compound, in which Z is formyl, is prepared directly by conditions such as the Vilsmeier-Haack Reaction or via hydrolsis of an intermediate compound in which Z is bis(alkythio)methyl or bis(arylthio)methyl;

e) is first reacted with a mixture of bromine and a metal thiocyanate to give an intermediate compound of formula (Ib), in which Z is thiocyano, which then is treated with an alkylating agent, optionally in the presence of a base to directly give a compound of formula (Ib), in which Z is alkylsulfenyl or haloalkylsulfenyl, or optionally the intermediate compound in which Z is thiocyano is first oxidized to a corresponding intermediate disulfide compound which is then reacted with a perhaloalkane, optionally in the presence of a reducing agent, to give a compound of formula (Ib) in which Z is haloalkylsulfenyl, particularly perhaloalkylsulfenyl, finally the compound, in which Z is alkylsulfenyl or haloalkylsulfenyl, is optionally oxidized by known methods similar to those of process P₁a to give a compound of formula (Ib), in which Z is alkylsulfinyl, haloalkylsulfinyl, alkylsulfonyl or haloalkylsulfonyl; or f) is first reacted as above in part e) to give the intermediate compound, in which Z is thiocyano, which is then cleaved by a free radical promoter, such as potassium ferricyanide, to give a compound of formula (Ib), in which Z is sulfhydryl or salts thereof.

P₃. A process of preparation of a compound of formula (Ib),

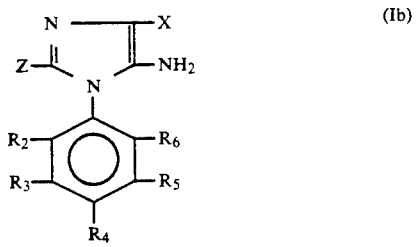

wherein X, R₂, R₃, R₄, R₅ and R₆ are as defined for formula (I) and Z is amino, alkyl, cyano, carboxyl and salts thereof, aminocarbonyl, alkylaminocarbonyl, dialkylaminocarbonyl, alkoxy-carbonyl, haloalkyl, cyanoalkyl, alkenyl, alkynyl, alkylcarbonyl or haloalkylcarbonyl, wherein a compound of formula (Ib), in which Z is formyl, prepared via procedures described in process P₂d, and in which X and amino are optionally protected as required:

a) is reduced to a compound of formula (Ib), in which Z is alkyl, particularly methyl, by known reducing agents such as sodium borohydride or p-toluenesulfonylhydrazine and sodium cyanoborohydride;

b) is reacted with a standard known oxidizing agent to give a compound of formula (Ib), in which Z is carboxyl or salts thereof, then optionally the carboxyl compound can be converted to a compound of formula (Ib), in which Z is amino, by a Curtius rearrangement via an intermediate acid halide, azide, and isocyanate or optionally the compound in which Z is carboxyl is treated with isophthalonitrile to give a compound of formula (Ib), in which Z is cyano, or optionally the compound in which Z is formyl is reacted with hydroxylamine to give an intermediate aldoxime compound which is then dehydrated by standard procedures to give the compound of formula (Ib), in which Z is cyano;

c) is converted to the compound in which Z is carboxyl by the procedure b) above, then the carboxyl is converted by standard procedures to an intermediate acid halide compound, which then is reacted with ammonia, an alkylamine, dialkylamine or alkyl alcohol to give a compound of formula (Ib), in which Z is aminocarbonyl, alkylaminocarbonyl, dialkylaminocarbonyl or alkoxycarbonyl;

d) is first reduced to an intermediate hydroxymethyl compound by procedures similar to those in process P₁b, followed by halogenation procedures also similar to those of process P₁b, to give a compound of formula (Ib), in which Z is haloalkyl, more specifically halomethyl, or optionally the haloalkyl compound, specifically halomethyl, is treated with a metal cyanide to give a compound of formula (Ib), in which Z is cyanoalkyl, more specifically cyanomethyl;

e) is reacted in a Wittig or modified Willig reaction to give a compound of formula (Ib), in which Z is alkenyl or alkynyl; or f) is reacted with a Grignard reagent or alkyllithium reagent to give an intermediate compound of formula (Ib), in which Z is α-hydroxyalkyl, then is oxidized with known reagents to give a compound of formula (Ib), in which Z is alkylcarbonyl, then the alkylcarbonyl compound is optionally halogenated to a compound of formula (Ib), in which Z is haloalkylcarbonyl.

P₄. A process of preparation of a compound of formula (Ib),

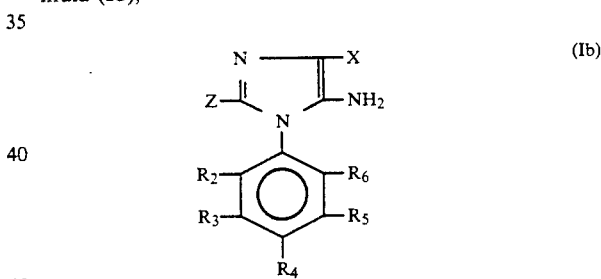

wherein X, R₂, R₃, R₄, R₅ and R₆ are as defined for formula (I) and Z is alkylamino, dialkylamino, trialkylammonium salt, alkoxycarbonylamino, alkylaminocarbonylamino, dialkylaminocarbonylamino, alkoxyalkylideneimino, alkylcarbonylamino, haloalkylcarbonylamino or arylcarbonylamino, wherein a compound of formula (Ib), in which Z is amino, prepared via procedures described in process P₂b or P₃b and in which X and Y is amino are optionally protected as required:

a) is first reacted with phosgene to give an intermediate compound of formula (Ib), in which Z is chlorocarbonylamino or isocyanato, which then is reacted with an alkyl alcohol, alkylamine or dialkylamine to give a compound of formula (Ib), in which Z is alkoxycarbonylamino, alkylaminocarbonylamino or dialkylaminocarbonylamine;

b) is reacted with an alkylating agent, such as an alkyl iodide or dialkyl sulfate or optionally by known reductive methylation using formaldehyde and formic acid to give a compound of formula (Ib), in which Z is alkylamino, dialkylamino or trialkylammonium salt;

c) is reacted with an alkyl orthoformate to give a compound of formula (Ib), in which Z is alkoxyalkylideneimino, particularly alkoxymethylideneimino; or d) is reacted with an alkyl-, haloalkyl- or arylcarbonyl halide, optionally in the presence of an acid acceptor, to give a compound of formula (Ib), in which Z is alkylcarbonylamino, haloalkylcarbonylamino or arylcarbonylamino.

P₅. A process of preparation of a compound of formula (I),

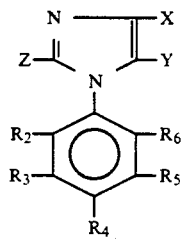

wherein X, Z, R₂, R₃, R₄, R₅ and R₆ are as defined for formula (I) and Y is hydrogen, amino, halogen, alkylsulfenyl, haloalkylsulfenyl, alkylsulfinyl, haloalkylsulfinyl, alkylsulfonyl, haloalkylsulfonyl, cyano or nitro, wherein a compound of formula (Ib),

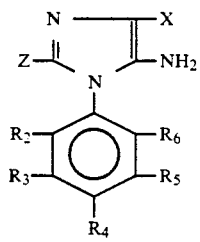

in which X, Z and R₂ to R₆ are as defined above and in which X, Z, and amino are optionally protected as required:

a) is deaminated by known procedures, such as with an alkylnitrite to convert the compound, in which Y is amino, into its corresponding diazonium salt, followed by quenching the diazonium salt with a quenching agent according to known procedures to obtain a compound of formula (I), in which Y is hydrogen, halogen, cyano, nitro, alkylsulfenyl, or haloalkylsulfenyl and then the compound, in which Y is alkylsulfenyl or haloalkylsulfenyl is optionally oxidized to a compound of formula (I), in which Y is alkylsulfinyl, haloalkylsulfinyl, alkylsulfonyl or haloalkylsulfonyl.

P₆. A process of preparation of a compound of formula (I),

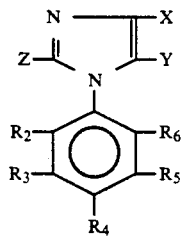

wherein X, Z, R₂, R₃, R₄, R₅ and R₆ are as defined for formula (I) and Y is alkoxycarbonylamino, alkylaminocarbonylamino, dialkylaminocarbonylamino, alkoxyalkylideneimino, alkylcarbonylamino, haloalkylcarbonylamino, arylcarbonylamino, alkylamino, dialkylamino or trialkylammonium salt, wherein a compound of formula (Ib),

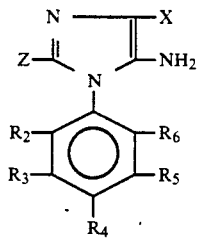

in which X, Z and R₂ to R₆ are as defined above and in which X, Z and amino are optionally protected as required:

a) is reacted in a manner similar to that described in process P₄a via a chlorocarbonylamino or isocyanato intermediate, obtained by reaction with phosgene, which then is by reacted with an alkyl alcohol, alkylamine, or dialkylamine to give a compound of formula (I), in which Y is alkoxycarbonylamino, alkylaminocarbonylamino or dialkylaminocarbonylamino;

b) is reacted in a manner similar to that described in process P₄c with an alkylorthoformate to give a compound of formula (I), in which Y is alkoxyalkylideneimino, particularly alkoxymethylideneimino;

c) is reacted in a similar manner to that described in process P₄b by alkylation or reductive methylation to give a compound of formula (I), in which Y is alkylamino, dialkylamino or trialkylammonium salt; or d) is reacted in a similar manner to that described in process P₄d with an alkyl-, haloalkyl- or arylcarbonyl halide to give a compound of formula (I), in which Y is alkylcarbonylamino, haloalkylcarbonylamino or arylcarbonylamino.

P₇. A process of preparation of a compound of formula (I),

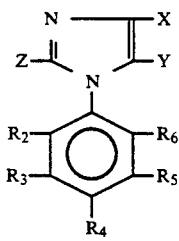

wherein X, Z, R₂, R₃, R₄, R₅ and R₆ are as defined for formula (I) and Y is nitro, sulfhydryl and salts thereof, hydroxyl and salts thereof, alkoxy, haloalkoxy, aminosulfonyl, alkylaminosulfonyl, dialkylaminosulfonyl, alkyl, haloalkyl, alkenyl, alkynyl, cyanoalkyl or formyl, wherein a compound of formula (Ib),

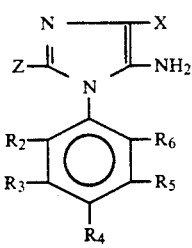

in which X, Z and $R_2$ to $R_6$ are as defined above and in which X and Z are optionally protected as required is deaminated according to the procedures described in process $P_5$ to give a compound of formula (I), in which Y is hydrogen, then said compound, in which X and Z are optionally protected as required:

a) is nitrated by procedures similar to those described in process $P_5b$ to give a compound of formula (I), in which Y is nitro;

b) is reacted in a similar manner by the procedures described in process $P_5f$ to first give an intermediate compound, in which Y is thiocyano, which is then reacted to give a compound of formula (I), in which Y is sulfhydryl and salts thereof;

c) is first reacted with a strong base such as an organolithium reagent to give an intermediate metal carbanion, which is then quenched with an electrophile to give a compound of formula (I), in which Y is alkyl, haloalkyl, alkenyl, alkynyl, cyanoalkyl or formyl;

d) is converted to the carbanion, as above in part c), and then quenched with sulfuryl chloride to give an intermediate compound, in which Y is chlorosulfonyl, which then is reacted with ammonia or an alkyl- or dialkylamine to give a compound of formula (I), in which Y is aminosulfonyl, alkylaminosulfonyl or dialkylaminosulfonyl;

e) is converted to the carbanion as above in part c) or optionally the carbanion is prepared via the compound in which Y is halogen, obtained by the procedure of process $P_5$, and then the carbanion is reacted in a similar manner to the procedure described in process $P_5c$ to give a compound of formula (I), in which Y is hydroxyl and salts thereof, alkoxy or haloalkoxy.

$P_8$. A process of preparation of a compound of formula (I),

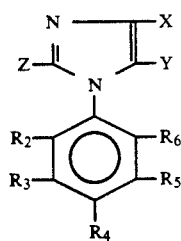

wherein X, Z, $R_2$, $R_3$, $R_4$, $R_5$ and $R_6$ are as defined for formula (I) and Y is carboxyl and salts thereof, cyano, aminocarbonyl, alkylaminocarbonyl, dialkylaminocarbonyl, alkoxycarbonyl, haloalkyl, alkenyl, alkynyl, alkylcarbonyl or haloalkylcarbonyl, wherein a compound of formula (Ib),

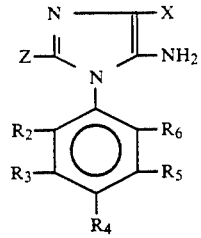

in which X, Z and $R_2$ to $R_6$ are as defined above is first deaminated according to the procedures described in process $P_5$ to give a compound, in which Y is hydrogen, which is then converted by procedures described in process $P_7c$ to give a compound of formula (I), in which Y is formyl, then said formyl compound, in which X and Z are optionally protected as required:

a) is reacted by similar procedures described in process $P_3b$ to give a compound of formula (I), in which Y is carboxyl and salts thereof or cyano;

b) is reacted by similar procedures described in process $P_3c$ to give a compound of formula (I), in which Y is aminocarbonyl, alkylaminocarbonyl, dialkylaminocarbonyl or alkoxycarbonyl;

c) is reacted by similar procedures described in process $P_3d$ to give a compound of formula (I), in which Y is haloalkyl, more specifically halomethyl;

d) is reacted by similar procedures described in process $P_2b$ and $P_3e$ to give a compound of formula (I), in which Y is alkenyl or alkynyl; or e) is reacted by similar procedures described in process $P_3f$ to give a compound of formula (I), in which Y is alkylcarbonyl or haloalkylcarbonyl.

$P_9$. A process of preparation of a compound of formula (I),

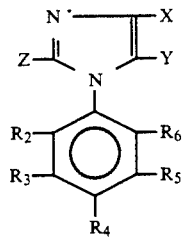

wherein Y, Z, $R_2$, $R_3$, $R_4$, $R_5$ and $R_6$ are as defined for formula (I) and X is alkylsulfenyl, haloalkylsulfenyl, alkylsulfinyl, haloalkylsulfinyl, alkylsulfonyl or haloalkylsulfonyl, wherein a compound of formula (Ic),

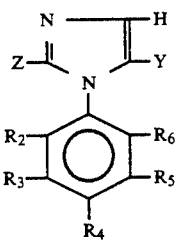

in which Y and Z are optionally protected as required:

a) is first reacted according to procedures similar to those described in process $P_2e$ to convert a compound of formula (Ic), in which X is hydrogen, to an intermediate compound of formula (I), in which X is successively thiocyano and then a disulfide, then also by procedures similar to those described in process $P_2e$, the thiocyano or disulfide intermediates are converted to a compound of formula (I), in which X is alkylsulfenyl or haloalkylsulfenyl, particularly perhaloalkylsulfenyl, which compound then is optionally oxidized by procedures similar to those in process $P_2e$, to obtain the sulfoxide or sulfone analogs, that is a compound of formula (I), in which X is alkylsulfinyl, haloalkylsulfinyl, preferably perhaloalkylsulfinyl, alkylsulfonyl or haloalkylsulfonyl, particularly perhaloalkylsulfonyl; or b) is first reacted according to procedures similar to those described in process $P_2a$ to convert the compound of formula (Ic), in which X is hydrogen to an intermediate compound of formula (I), in which X is chlorosulfonyl, then the chlorosulfonyl compound is reacted with a reducing agent such as triphenylphosphine to give the same disulfide intermediate described above in part a), then finally the disulfide is converted by the procedures described above in part a) to give a compound of formula (I), in which X is alkylsulfenyl or haloalkylsulfenyl, particularly perhaloalkylsulfenyl or optionally the sulfenyl compound is oxidized to give a compound of formula (I), in which X is alkylsulfinyl, haloalkylsulfinyl, particularly perhaloalkylsulfinyl, alkylsulfonyl or haloalkylsulfonyl, particularly perhaloalkylsulfonyl.

$P_{10}$. A process of preparation of a compound of formula (IV),

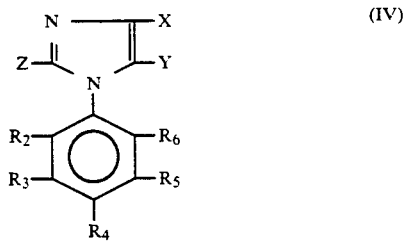

wherein:
$R_2$, $R_3$, $R_4$, $R_5$ and $R_6$ are as defined in formula (I);
X is hydrogen or haloalkyl, particularly trifluoromethyl;
Y is amino; hydroxy optionally existing in its isomeric keto form when X is hydrogen; alkoxy or haloalkoxy;
Z is hydrogen; halogen; alkyl; haloalkyl; hydroxy, optionally existing in its isomeric keto form when X is hydrogen and Y is imino; alkoxy or haloalkoxy;
whereby a compound of formula (III),

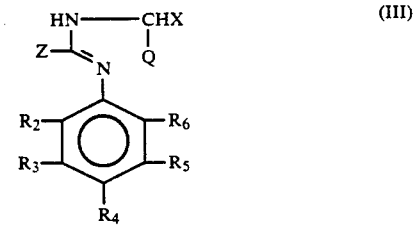

wherein:
$R_2$, $R_3$, $R_4$, $R_5$ and $R_6$ are as defined above; and
X is hydrogen or haloalkyl, particularly trifluoromethyl;

Z is hydrogen, halogen, alkyl, haloalkyl or hydroxy, optionally existing in its isomeric keto form; and
Q is cyano or lower alkoxycarbonyl;
is reacted with a basic agent in a suitable reaction medium to give a compound of formula (IV) which when Y or Z is hydroxy, is then optionally alkylated or haloalkylated to Y or Z is alkoxy or haloalkoxy.

$P_{11}$. The process of preparation of a compound of formula (IV), according to process $P_{10}$, whereby the compound of formula (IV) is:

a) a compound of formula (5), in which X and Z are each hydrogen and Y is amino;
b) a compound of formula (17), in which X is hydrogen, Y is amino, and Z is halogen, particularly chlorine;
c) a compound of formula (22), in which X is hydrogen, Y is amino, and Z is alkyl or haloalkyl;
d) a compound of formula (27), in which X is haloalkyl, particularly trifluoromethyl, Y is amino, and Z is halogen, alkyl, or haloalkyl;
e) a compound of formula (30), optionally existing in its isomeric keto form (29), in which X is hydrogen, Y is hydroxyl, which is optionally alkylated to Y is alkoxy or haloalkoxy, and Z is halogen, alkyl or haloalkyl; or
f) a compound formula (37), optionally existing in its isomeric keto-imino form (34), in which X is hydrogen, Y is amino, and Z is hydroxy, which is optionally alkylated to Z is alkoxy or haloalkoxy or optionally halogenated to Z is halogen.

$P_{12}$. A process of preparation of a compound of formula (I), wherein X, Y, Z, $R_2$, $R_3$, $R_4$, $R_5$ and $R_6$ are as defined in formula (I), whereby a compound of formula (5) is reacted according to the process of preparation of any of processes $P_1$ to $P_9$ for introduction of the X, Y and Z substituents.

$P_{13}$. A process of preparation of a compound of formula (I), wherein X, Y, $R_2$, $R_3$, $R_4$, $R_5$ and $R_6$ are as defined in formula (I) and Z is halogen, whereby a compound of formula (17) is reacted according to the process of preparation of any of processes $P_1$ to $P_9$ for introduction of the X and Y substituents.

$P_{14}$. A process of preparation of a compound of formula (I), wherein X, Y. $R_2$, $R_3$, $R_4$, $R_5$ and $R_6$ are as defined in formula (I) and Z is alkyl or haloalkyl, whereby a compound of formula (22) is reacted according to the process of preparation of any of processes $P_1$ to $P_9$ for introduction of the X and Y substituents.

$P_{15}$. A process of preparation of a compound of formula (I), wherein Y, $R_2$, $R_3$, $R_4$, $R_5$ and $R_6$ are as defined in formula (I), X is haloalkyl, particularly trifluoromethyl, and Z is halogen, alkyl or haloalkyl, whereby a compound of formula (27) is reacted according to the process of any of processes $P_1$ to $P_9$ for introduction of the Y substituent.

$P_{16}$. A process of preparation of a compound of formula (I), wherein X, $R_2$, $R_3$, $R_4$, $R_5$ and $R_6$ are as defined in formula (I), Y is hydroxy, alkoxy or haloalkoxy, and Z is halogen, alkyl or haloalkyl, whereby a compound of formula (30), optionally existing in its isomeric keto form (29), in which Y is hydroxy, optionally alkylated to Y is alkoxy or haloalkoxy, is reacted according to the process of preparation of any of processes $P_1$ to $P_9$ for introduction of the X substituent.

$P_{17}$. A process of preparation of a compound of formula (I), wherein X, Y, $R_2$, $R_3$, $R_4$, $R_5$ and $R_6$ are as defined in formula (I) and Z is hydroxy, alkoxy, haloalkoxy or halogen, whereby a compound of formula (37), optionally existing in its isomeric keto-imino form (34), in which Z is hydroxy, optionally alkylated to Z is alkoxy or haloalkoxy or optionally halogenated to Z is halogen, is reacted according to the process of preparation of any of processes $P_1$ to $P_9$ for introduction of X and Y substituents.

$P_{18}$. The invention is also related to intermediate compounds as follows: a compound of formula (Ia), (Ib), (Ic), (IV), 5, 17, 22, 27, (30)/(29), or (37)/(34), wherein the substituents X, Y, Z, $R_2$, $R_3$, $R_4$, $R_5$ and $R_6$ are as defined in processes $P_1$ to $P_{17}$, which compound is useful for the preparation of a compound of formula (I), according to any of processes $P_1$ to $P_{17}$.

$P_{19}$. The invention is also related to intermediate compounds as follows: a compound of formula (III),

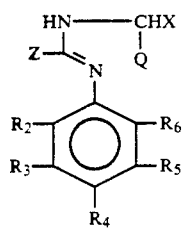

wherein:
$R_2$, $R_3$, $R_4$, $R_5$ and $R_6$ are as defined in formula (I);
X is hydrogen or haloalkyl, particularly trifluoromethyl;
Z is hydrogen, halogen, alkyl, haloalkyl or hydroxy, optionally existing in its isomeric keto form; and
Q is cyano or lower alkoxycarbonyl,
which compound is useful for the preparation of an intermediate N-phenylimidazole used in the preparation of a compound of formula (I), according to any of processes $P_1$ to $P_{17}$. Specific compounds of formula (III) are compounds of formula (4), (16), (21), (26), (28) or (33).

REPRESENTATIVE COMPOUNDS OF THE INVENTION

The compounds in TABLE 1 are illustrative of some of the preferred compounds within the purview of the above generic formula (I) or (IIa) or (IIb) and can be prepared by the herein described methods or processes of synthesis, by the appropriate selection of reactants, conditions and procedures, which are commonly known and apparent to one skilled in the art.

TABLE 1
REPRESENTATIVE 1-ARYLIMIDAZOLE COMPOUNDS OF FORMULA (I)
SUBSTITUENT GROUPS

| No. | X | Y | Z | $R_2$ | $R_3$ | $R_4$ | $R_5$ | $R_6$ |
|---|---|---|---|---|---|---|---|---|
| 1 | $SCF_3$ | H | H | Cl | H | $OCF_3$ | H | Cl |
| 2 | $SCF_3$ | H | $CH_3$ | Cl | H | $OCF_3$ | H | Cl |
| 3 | $SCF_3$ | H | Cl | Cl | H | $OCF_3$ | H | Cl |
| 4 | $SCF_3$ | H | Br | Cl | H | $OCF_3$ | H | Cl |
| 5 | $SOCF_3$ | H | Cl | Cl | H | $OCF_3$ | H | Cl |
| 6 | $SO_2CF_3$ | H | Cl | Cl | H | $OCF_3$ | H | Cl |
| 7 | $SOCF_3$ | H | Br | Cl | H | $OCF_3$ | H | Cl |
| 8 | $SO_2CF_3$ | H | Br | Cl | H | $OCF_3$ | H | Cl |
| 9 | $SCF_3$ | H | $CF_3$ | Cl | H | $OCF_3$ | H | Cl |
| 10 | $SOCF_3$ | H | $CF_3$ | Cl | H | $OCF_3$ | H | Cl |
| 11 | $SO_2CF_3$ | H | $CF_3$ | Cl | H | $OCF_3$ | H | Cl |
| 12 | $SCF_3$ | H | $CF_3$ | Cl | H | $CF_3$ | H | Cl |
| 13 | $SOCF_3$ | H | $CF_3$ | Cl | H | $CF_3$ | H | Cl |
| 14 | $SO_2CF_3$ | H | $CF_3$ | Cl | H | $CF_3$ | H | Cl |
| 15 | $SCF_3$ | H | $OCH_3$ | Cl | H | $CF_3$ | H | Cl |
| 16 | $SOCF_3$ | H | $OCH_3$ | Cl | H | $CF_3$ | H | Cl |
| 17 | $SOCF_3$ | H | SH | Cl | H | $CF_3$ | H | Cl |
| 18 | $SCF_3$ | H | $SCF_3$ | Cl | H | $CF_3$ | H | Cl |
| 19 | $SOCF_3$ | H | $SCF_3$ | Cl | H | $CF_3$ | H | Cl |
| 20 | $SOCF_3$ | H | $SOCF_3$ | Cl | H | $CF_3$ | H | Cl |
| 21 | $SOCF_3$ | H | $SO_2CF_3$ | Cl | H | $CF_3$ | H | Cl |
| 22 | $SCF_3$ | H | $SCF_3$ | Cl | H | $OCF_3$ | H | Cl |
| 23 | $SCF_3$ | H | $SCH_3$ | Cl | H | $CF_3$ | H | Cl |
| 24 | $SOCF_3$ | H | $SCH_3$ | Cl | H | $CF_3$ | H | Cl |
| 25 | $SO_2CF_3$ | H | $SCH_3$ | Cl | H | $CF_3$ | H | Cl |
| 26 | $SCF_3$ | H | $SOCH_3$ | Cl | H | $CF_3$ | H | Cl |
| 27 | $SOCF_3$ | H | $SOCH_3$ | Cl | H | $CF_3$ | H | Cl |
| 28 | $SOCF_3$ | H | $SO_2CH_3$ | Cl | H | $CF_3$ | H | Cl |
| 29 | $SCF_3$ | H | CN | Cl | H | $CF_3$ | H | Cl |
| 30 | $SOCF_3$ | H | CN | Cl | H | $CF_3$ | H | Cl |
| 31 | $SO_2CF_3$ | H | CN | Cl | H | $CF_3$ | H | Cl |
| 32 | $SCF_3$ | H | F | Cl | H | $CF_3$ | H | Cl |
| 33 | $SOCF_3$ | H | F | Cl | H | $CF_3$ | H | Cl |
| 34 | $SO_2CF_3$ | H | F | Cl | H | $CF_3$ | H | Cl |
| 35 | $SCF_3$ | H | Cl | Br | H | $CF_3$ | H | Cl |
| 36 | $SCF_3$ | H | Cl | H | H | $CF_3$ | H | Cl |
| 37 | $SCF_3$ | H | Cl | H | H | $CF_3$ | H | Br |
| 38 | $SOCF_3$ | H | Br | H | H | $CF_3$ | H | Cl |
| 39 | $SO_2CF_3$ | H | Br | H | H | $CF_3$ | H | Cl |
| 40 | $SOCF_3$ | H | Cl | Cl | H | Br | H | Cl |
| 41 | $SCF_3$ | H | Cl | F | F | $CF_3$ | F | F |
| 42 | $SOCF_3$ | H | Cl | F | F | $CF_3$ | F | F |
| 43 | $SO_2CF_3$ | H | Cl | F | F | $CF_3$ | F | F |
| 44 | $SCF_3$ | H | Cl | Cl | H | $t-C_4H_9$ | H | Cl |
| 45 | $SCF_2Cl$ | H | Cl | Cl | H | $OCF_3$ | H | Cl |
| 46 | $SOCF_2Cl$ | H | Cl | Cl | H | $OCF_3$ | H | Cl |
| 47 | $SO_2CF_2Cl$ | H | Cl | Cl | H | $OCF_3$ | H | Cl |
| 48 | $SCF_2Cl$ | H | Br | Cl | H | $OCF_3$ | H | Cl |
| 49 | $SOCF_2Cl$ | H | Br | Cl | H | $OCF_3$ | H | Cl |

TABLE 1-continued
REPRESENTATIVE 1-ARYLIMIDAZOLE COMPOUNDS OF FORMULA (I)
SUBSTITUENT GROUPS

| No. | X | Y | Z | $R_2$ | $R_3$ | $R_4$ | $R_5$ | $R_6$ |
|---|---|---|---|---|---|---|---|---|
| 50 | $SO_2CF_2Cl$ | H | Br | Cl | H | $OCF_3$ | H | Cl |
| 51 | $SCF_2Cl$ | H | $SCF_2Cl$ | Cl | H | $OCF_3$ | H | Cl |
| 52 | $SCF_2Cl$ | H | CN | Cl | H | $CF_3$ | H | Cl |
| 53 | $SOCF_2Cl$ | H | CN | Cl | H | $CF_{F3}$ | H | Cl |
| 54 | $SO_2CF_2Cl$ | H | CN | Cl | H | $CF_3$ | H | Cl |
| 55 | $SCF_2Cl$ | H | F | Cl | H | $CF_3$ | H | Cl |
| 56 | $SOCF_2Cl$ | H | F | Cl | H | $CF_3$ | H | Cl |
| 57 | $SO_2CF_2Cl$ | H | F | Cl | H | $CF_3$ | H | Cl |
| 58 | $SCF_2Cl$ | H | $CH_3$ | Cl | H | $CF_3$ | H | Cl |
| 59 | $SCF_2Cl$ | H | $SCH_3$ | Cl | H | $CF_3$ | H | Cl |
| 60 | $SOCF_2Cl$ | H | $SCH_3$ | Cl | H | $CF_3$ | H | Cl |
| 61 | $SO_2CF_2Cl$ | H | $SCH_3$ | Cl | H | $CF_3$ | H | Cl |
| 62 | $SOCF_2Cl$ | H | $SOCH_3$ | Cl | H | $CF_3$ | H | Cl |
| 63 | $SCF_2Cl$ | H | Cl | H | H | $CF_3$ | H | Cl |
| 64 | $SOCF_2Cl$ | H | Cl | H | H | $CF_3$ | H | Cl |
| 65 | $SOCF_2Cl$ | H | Br | H | H | $CF_3$ | H | Cl |
| 66 | $SOCF_2Cl$ | H | Cl | H | H | $CF_3$ | H | Br |
| 67 | $SCF_2Cl$ | H | $OCH_3$ | H | H | $CF_3$ | H | Cl |
| 68 | $SOCF_2Cl$ | H | $OCH_3$ | H | H | $CF_3$ | H | Cl |
| 69 | $SCCl_2F$ | H | $SCH_3$ | Cl | H | $CF_3$ | H | Cl |
| 70 | $SOCCl_2F$ | H | $SCH_3$ | Cl | H | $CF_3$ | H | Cl |
| 71 | $SO_2CCl_2F$ | H | $SCH_3$ | Cl | H | $CF_3$ | H | Cl |
| 72 | $SCCl_2F$ | H | $SOCH_3$ | Cl | H | $CF_3$ | H | Cl |
| 73 | $SOCCl_2F$ | H | $SOCH_3$ | Cl | H | $CF_3$ | H | Cl |
| 74 | $SO_2CCl_2F$ | H | $SOCH_3$ | Cl | H | $CF_3$ | H | Cl |
| 75 | $SCCl_2F$ | H | Cl | Cl | H | $OCF_3$ | H | Cl |
| 76 | $SOCCl_2F$ | H | Cl | Cl | H | $OCF_3$ | H | Cl |
| 77 | $SO_2CCl_2F$ | H | Cl | Cl | H | $OCF_3$ | H | Cl |
| 78 | $SCCl_2F$ | H | CN | Cl | H | $CF_3$ | H | Cl |
| 79 | $SOCCl_2F$ | H | CN | Cl | H | $CF_3$ | H | Cl |
| 80 | $SO_2CCl_2F$ | H | CN | Cl | H | $CF_3$ | H | Cl |
| 81 | $SCCl_2F$ | H | $NO_2$ | Cl | H | $CF_3$ | H | Cl |
| 82 | $SOCCl_2F$ | H | $C_2H_5$ | Cl | H | $CF_3$ | H | Cl |
| 83 | $SCCl_2F$ | H | $OCH_3$ | Cl | H | $CF_3$ | H | Cl |
| 84 | $SOCCl_2F$ | H | $CF_3$ | Cl | H | $CF_3$ | H | Cl |
| 85 | $SCCl_2F$ | H | $SCCl_2F$ | Cl | H | $CF_3$ | H | Cl |
| 86 | $SCCl_2F$ | H | $NH_2$ | Cl | H | $CF_3$ | H | Cl |
| 87 | $SCCl_2F$ | $NHCOCH_3$ | Cl | Cl | H | $CF_3$ | H | Cl |
| 88 | $SCCl_2F$ | $NHCOCF_3$ | Cl | Cl | H | $CF_3$ | H | Cl |
| 89 | $SOCCl_2F$ | $NHCOCH_3$ | Br | Cl | H | $CF_3$ | H | Cl |
| 90 | $SOCCl_2F$ | $N=CHOC_2H_5$ | Cl | Cl | H | $CF_3$ | H | Cl |
| 91 | $SOCCl_2F$ | $NHCOOCH_3$ | Cl | Cl | H | $CF_3$ | H | Cl |
| 92 | $SOCCl_2F$ | $NHCONHCH_3$ | Cl | Cl | H | $CF_3$ | H | Cl |
| 93 | $SOCCl_2F$ | $NHCON(CH_3)_2$ | Cl | Cl | H | $CF_3$ | H | Cl |
| 94 | $SOCCl_2F$ | H | $CH_2CH=CH_2$ | Cl | H | $CF_3$ | H | Cl |
| 95 | $SOCCl_2F$ | H | $OCF_3$ | Cl | H | $CF_3$ | H | Cl |
| 96 | $SCCl_2F$ | H | $COCF_3$ | Cl | H | $CF_3$ | H | Cl |
| 97 | $SCCl_2F$ | H | CHO | Cl | H | $CF_3$ | H | Cl |
| 98 | $SCCl_2F$ | H | $COCH_3$ | Cl | H | $CF_3$ | H | Cl |
| 99 | $SCCl_2F$ | H | $COOC_2H_5$ | Cl | H | $CF_3$ | H | Cl |
| 100 | $SOCCl_2F$ | COOH | H | Cl | H | $CF_3$ | H | Cl |
| 101 | $SOCCl_2F$ | $CONH_2$ | H | Cl | H | $CF_3$ | H | Cl |
| 102 | $SOCCl_2F$ | $CONHCH_3$ | H | Cl | H | $CF_3$ | H | Cl |
| 103 | $SOCCl_2F$ | $CON(CH_3)_2$ | H | Cl | H | $CF_3$ | H | Cl |
| 104 | $SOCCl_2F$ | H | $CH_2CH=CH_2$ | Cl | H | $CF_3$ | H | Cl |
| 105 | $SOCCl_2F$ | H | $CH_2CN$ | Cl | H | $CF_3$ | H | Cl |
| 106 | $SOCCl_2F$ | Br | H | Cl | H | $OCF_3$ | H | Cl |
| 107 | $SOCCl_2F$ | H | Cl | Cl | H | $CF_3$ | H | Cl |
| 108 | $SOCCl_2F$ | H | Cl | $NO_2$ | H | $CF_3$ | H | Cl |
| 109 | $SOCCl_2F$ | H | Cl | $NH_2$ | H | $CF_3$ | H | Cl |
| 110 | $SOCCl_2F$ | H | Cl | $NHCH_3$ | H | $CF_3$ | H | Cl |
| 111 | $SOCCl_2F$ | H | Cl | CN | H | $CF_3$ | H | Cl |
| 112 | $SOCCl_2F$ | H | Cl | $CH_3$ | H | $CF_3$ | H | Cl |
| 113 | $SOCCl_2F$ | H | Cl | $OCH_3$ | H | $CF_3$ | H | Cl |
| 114 | $SOCCl_2F$ | H | Br | Cl | H | $CF_3$ | H | Cl |
| 115 | $SOCCl_2F$ | H | Br | Br | H | $CF_3$ | H | Cl |
| 116 | $SCCl_2F$ | H | F | Cl | H | $CF_3$ | H | Cl |
| 117 | $SOCCl_2F$ | H | F | Cl | H | $CF_3$ | H | Cl |
| 118 | $SO_2CCl_2F$ | H | F | Cl | H | $CF_3$ | H | Cl |
| 119 | $SOCCl_2F$ | H | Cl | Cl | H | $t-C_4H_9$ | H | Cl |
| 120 | $SOCCl_2F$ | H | Cl | Cl | H | Br | H | Cl |
| 121 | $SCCl_2F$ | H | Cl | Cl | H | $SCF_3$ | H | Cl |
| 122 | $SCCl_2F$ | H | Cl | Cl | H | $SOCF_3$ | H | Cl |
| 123 | $SCCl_2F$ | H | Cl | Cl | H | $SO_2CF_3$ | H | Cl |
| 124 | $SCCl_2F$ | H | Cl | Cl | Cl | $CF_3$ | H | Cl |
| 125 | $SCCl_3$ | H | Cl | Cl | H | $CF_3$ | H | Cl |
| 126 | $SOCCl_3$ | H | Cl | Cl | H | $CF_3$ | H | Cl |
| 127 | $SO_2CCl_3$ | H | Cl | Cl | H | $CF_3$ | H | Cl |
| 128 | $SCCl_3$ | Cl | Br | Cl | H | $CF_3$ | H | Cl |

TABLE 1-continued

REPRESENTATIVE 1-ARYLIMIDAZOLE COMPOUNDS OF FORMULA (I)
SUBSTITUENT GROUPS

| No. | X | Y | Z | $R_2$ | $R_3$ | $R_4$ | $R_5$ | $R_6$ |
|---|---|---|---|---|---|---|---|---|
| 129 | $SOCCl_3$ | Cl | Br | Cl | H | $CF_3$ | H | Cl |
| 130 | $SO_2CCl_3$ | Cl | Br | Cl | H | $CF_3$ | H | Cl |
| 131 | $SOCCl_3$ | $SCH_3$ | H | Cl | H | $CF_3$ | H | Cl |
| 132 | $SOCCl_3$ | H | $SCH_3$ | Cl | H | $CF_3$ | H | Cl |
| 133 | $SCCl_3$ | H | $SOCH_3$ | Cl | H | $CF_3$ | H | Cl |
| 134 | $SCF_2CFCl_2$ | H | Cl | Cl | H | $CF_3$ | H | Cl |
| 135 | $SOCF_2CFCl_2$ | H | Cl | Cl | H | $CF_3$ | H | Cl |
| 136 | $SO_2CF_2CFCl_2$ | H | Cl | Cl | H | $CF_3$ | H | Cl |
| 137 | $SOCF_2CFCl_2$ | H | Br | Cl | H | $CF_3$ | H | Cl |
| 138 | $SCH_3$ | H | Cl | Cl | H | $CF_3$ | H | Cl |
| 139 | $SOCH_3$ | H | Cl | Cl | H | $CF_3$ | H | Cl |
| 140 | $SO_2CH_3$ | H | Cl | Cl | H | $CF_3$ | H | Cl |
| 141 | $CF_3$ | H | Cl | Cl | H | $CF_3$ | H | Cl |
| 142 | $OCF_3$ | H | Cl | Cl | H | $CF_3$ | H | Cl |
| 143 | $SCF_3$ | OH | Cl | Cl | H | $CF_3$ | H | Cl |
| 144 | $SOCCl_2F$ | $NHCH_3$ | Cl | Cl | H | $CF_3$ | H | Cl |
| 145 | $SOCCl_2F$ | $N(CH_3)_2$ | Cl | Cl | H | $CF_3$ | H | Cl |
| 146 | $SOCCl_2F$ | $CH_2C\equiv CH$ | Cl | Cl | H | $CF_3$ | H | Cl |
| 147 | $SOCCl_2F$ | H | OH | Cl | H | $CF_3$ | H | Cl |
| 148 | $SOCCl_2F$ | Cl | $NHCH_3$ | Cl | H | $CF_3$ | H | Cl |
| 149 | $SOCCl_2F$ | H | $N(CH_3)_2$ | Cl | H | $CF_3$ | H | Cl |
| 150 | $SOCCl_2F$ | H | $CH_2C\equiv CH$ | Cl | H | $CF_3$ | H | Cl |
| 151 | $SOCCl_2F$ | H | Cl | Cl | H | $SOCH_3$ | H | Cl |
| 152 | $SOCCl_2F$ | H | Cl | Cl | H | $SOt-C_4H_9$ | H | Cl |
| 153 | $SCCl_2F$ | H | Cl | Cl | H | $SO_2t-C_4H_9$ | H | Cl |
| 154 | $SOCF_3$ | H | Cl | Cl | H | Br | H | Cl |
| 155 | $SOCF_2Br$ | H | Cl | Cl | H | Cl | H | Cl |
| 156 | $SOCCl_2F$ | $SO_2NH_2$ | Cl | Cl | H | Cl | H | Cl |
| 157 | $SOCCl_2F$ | $SO_2NHCH_3$ | Cl | Cl | H | $CF_3$ | H | Cl |
| 158 | $SOCCl_2F$ | $SO_2N(CH_3)_2$ | Cl | Cl | H | $CF_3$ | H | Cl |
| 159 | $SCF_3$ | $N(CH_3)_3^+$ | Cl | Cl | H | $CF_3$ | H | Cl |
| 160 | $SOCCl_2F$ | SNa | Cl | Cl | H | $CF_3$ | H | Cl |
| 161 | $SOCCl_2F$ | ONa | Cl | Cl | H | $CF_3$ | H | Cl |
| 162 | $SOCCl_2F$ | COONa | Cl | Cl | H | $CF_3$ | H | Cl |
| 163 | $SOCCl_2CF_3$ | H | Cl | Cl | H | $CF_3$ | H | Cl |
| 164 | $SOCF_3$ | H | Cl | Cl | H | $CH_2CF_3$ | H | Cl |
| 165 | $SCF_3$ | H | $CH_3$ | Cl | H | $OCF_3$ | H | Cl |
| 166 | $SOCF_3$ | H | $CH_3$ | H | H | $OCF_3$ | H | Cl |
| 167 | $SOCCl_2F$ | H | $CH_3$ | Cl | H | $OCF_3$ | H | Cl |
| 168 | $SOCF_3$ | H | $CH_3$ | Br | H | $OCF_3$ | H | Cl |
| 169 | $SOCCl_2F$ | H | $CH_3$ | Br | H | $OCF_3$ | H | Cl |
| 170 | $SOCClF_2$ | H | Cl | Br | H | $OCF_3$ | H | Cl |
| 171 | $SOCF_3$ | H | H | $t-C_4H_9$ | H | Cl | H | H |
| 172 | $SOCCl_2F$ | H | Cl | $t-C_4H_9$ | H | Br | H | H |
| 173 | $SOClF_2$ | H | $CH_3$ | $t-C_4H_9$ | H | Cl | H | H |
| 174 | $SOCF_3$ | H | Cl | $t-C_4H_9$ | H | Cl | H | Cl |
| 175 | $SOCCl_2F$ | H | H | $t-C_4H_9$ | H | Cl | H | Cl |
| 176 | $SCCl_2F$ | H | H | $t-C_4H_9$ | H | Cl | H | H |
| 177 | $SOCH_3$ | H | $CH_3$ | Cl | H | $OCF_3$ | H | Cl |
| 178 | $SOCH_3$ | H | Cl | $t-C_4H_9$ | H | Cl | H | H |
| 179 | $SO_2CCl_2F$ | H | $CH_3$ | Cl | H | $OCF_3$ | H | Cl |
| 180 | $SOCCl_2F$ | H | $CHF_2$ | Cl | H | $CF_3$ | H | Cl |
| 181 | $SOCCl_2F$ | H | $CH_2Cl$ | Cl | H | $CF_3$ | H | Cl |
| 182 | $SOCCl_2F$ | H | $CH_2CH_2CH_2CH_3$ | Cl | H | $CF_3$ | H | Cl |
| 183 | $SCCl_2F$ | H | $CH=CH_2$ | Cl | H | $CF_3$ | H | Cl |
| 184 | $SOCCl_2F$ | H | $CH=CH_2-CH_3$ | Cl | H | $CF_3$ | H | Cl |
| 185 | $SOClF_2$ | H | $CH-(CH_3)_2$ | Cl | H | $CF_3$ | H | Cl |
| 186 | $SOCCl_2F$ | H | COOH | Cl | H | $CF_3$ | H | Cl |
| 187 | $SOCCl_2F$ | $CF_3$ | H | Cl | H | $CF_3$ | H | Cl |
| 188 | $SOCCl_2F$ | $CH=CH_2$ | H | Cl | H | $CF_3$ | H | Cl |
| 189 | $SOCCl_2F$ | $CH=CH_2-CH_3$ | H | Cl | H | $CF_3$ | H | Cl |
| 190 | $SCCl_2F$ | CN | H | Cl | H | $CF_3$ | H | Cl |
| 191 | $SCCl_2F$ | H | $CH_3$ | Cl | H | Cl | H | Cl |
| 192 | $S(O)C\ CL_2F$ | H | $CH_3$ | Cl | H | Br | H | Cl |
| 193 | $SCCl_2F$ | H | $CH_3$ | H | H | Cl | H | Cl |
| 194 | $SCCl_2F$ | H | $CH_3$ | Cl | H | F | H | Cl |
| 195 | $SCCl_2F$ | H | $CH_3$ | Br | H | F | H | Cl |
| 196 | $SOCCl_2F$ | H | $CH_3$ | Cl | H | F | H | Cl |
| 197 | $SCCl_2F$ | H | $CH_3$ | Cl | H | H | H | Cl |
| 198 | $SCCl_2F$ | $SCH_3$ | $CH_3$ | Cl | H | F | H | Cl |
| 199 | $SCCl_2F$ | $CH_3$ | $CH_3$ | Cl | H | $CF_3$ | H | Cl |
| 200 | $SCCl_2F$ | $CH_3$ | $CH_3$ | Cl | H | F | H | Cl |
| 201 | $SCCl_2F$ | $SCH_3$ | $CH_3$ | Cl | H | H | H | Cl |
| 202 | $SCClF_2$ | H | $CH_3$ | Cl | H | F | H | Cl |
| 203 | $SCCl_2F$ | $CH_3$ | H | Cl | H | Cl | H | Cl |
| 204 | $SCCl_2F$ | $OCH_3$ | H | Cl | H | Cl | H | Cl |
| 205 | $SCCl_2F$ | $CH_3$ | H | Cl | H | F | H | Cl |
| 206 | $SCCl_2F$ | $N=CHOC_2H_5$ | H | Cl | H | F | H | Cl |
| 207 | $SCCl_2F$ | $N=CHOCH_3$ | $CH_3$ | Cl | H | F | H | Cl |

TABLE 1-continued

REPRESENTATIVE 1-ARYLIMIDAZOLE COMPOUNDS OF FORMULA (I)
SUBSTITUENT GROUPS

| No. | X | Y | Z | $R_2$ | $R_3$ | $R_4$ | $R_5$ | $R_6$ |
|---|---|---|---|---|---|---|---|---|
| 208 | $SCCl_2F$ | $C_2H_5$ | H | Cl | H | $CF_3$ | H | Cl |
| 209 | $SCCl_2F$ | $C_2H_5$ | H | Cl | H | F | H | Cl |
| 210 | $SOCCl_2F$ | $SCH_3$ | H | Cl | H | Cl | H | Cl |
| 211 | $SOCCl_2F$ | $SCH_3$ | H | Cl | H | F | H | Cl |
| 212 | $SCCl_2F$ | $SCH_3$ | H | Cl | H | $SCH_3$ | H | Cl |
| 213 | $SCCl_2F$ | $SOCH_3$ | H | Cl | H | Cl | H | Cl |
| 214 | $SCCl_2F$ | $SO_2CH_3$ | H | Cl | H | F | H | Cl |
| 215 | $SOCCl_2F$ | $SOCH_3$ | H | Cl | H | F | H | Cl |
| 216 | $SOCCl_2F$ | Br | H | Br | H | H | H | Cl |
| 217 | $SCCl_2F$ | Br | H | Br | H | $C_2H_5$ | H | Cl |
| 218 | $SCCl_2F$ | F | H | Cl | H | F | H | Cl |
| 219 | $SCCl_2F$ | $SCH_3$ | H | Cl | H | I | H | Cl |
| 220 | $SCCl_2F$ | Br | H | $SCH_3$ | H | F | H | Cl |
| 221 | $SCCl_2F$ | $SCH_3$ | H | $SCH_3$ | H | Cl | H | Cl |
| 222 | $CF_3$ | $SCH_3$ | H | Cl | H | F | H | Cl |
| 223 | $SOCCl_2F$ | $SCH_3$ | Cl | Cl | H | $CF_3$ | H | Cl |
| 224 | $SOCCl_2F$ | $SCH_3$ | $CH_3$ | Cl | H | $CF_3$ | H | Cl |
| 225 | $SO_2CCl_2F$ | $SCH_3$ | $CH_3$ | Cl | H | $CF_3$ | H | Cl |
| 226 | $SOCCl_2F$ | $SOCH_3$ | $CH_3$ | Cl | H | $CF_3$ | H | Cl |
| 227 | $SO_2CClF_2$ | $SCH_3$ | Br | $SCH_3$ | H | $CF_3$ | H | Cl |
| 228 | $SCCl_2F$ | $SCH_3$ | Cl | Cl | H | $CF_3$ | H | Cl |
| 229 | $SOCClF_3$ | $SCH_3$ | Br | Cl | H | $CF_3$ | H | Cl |
| 230 | $SOCCl_2F$ | H | Cl | Cl | H | F | H | Cl |
| 231 | $SO_2ClF_2$ | H | Br | $SCH_3$ | H | F | H | Cl |
| 232 | $SOCCl_2F$ | $CH_3$ | Cl | Cl | H | $CF_3$ | H | Cl |
| 233 | $SOCCl_2F$ | $C_2H_5$ | Cl | Cl | H | $CF_3$ | H | Cl |
| 234 | $SOCCl_2F$ | $SCH_3$ | Cl | Cl | H | $OCF_3$ | H | Cl |
| 235 | $SOCF_3$ | $SCH_3$ | Cl | Cl | H | $CF_3$ | H | Cl |
| 236 | $SOCCl_2F$ | $SCH_3$ | H | Cl | H | $CF_3$ | H | Cl |
| 237 | $SCBrClF$ | $SCH_3$ | H | Cl | H | Cl | H | Cl |
| 238 | $SOCBrClF$ | $SCH_3$ | H | Cl | H | Cl | H | Cl |
| 239 | $SO_2CBrClF$ | $SCH_3$ | H | Cl | H | Cl | H | Cl |
| 240 | $SOCBrF_2$ | $SCH_3$ | H | Cl | H | Cl | H | Cl |
| 241 | $SCBrF_2$ | $SCH_3$ | H | Cl | H | Cl | H | Cl |
| 242 | $SCBrClF$ | $SCH_3$ | H | Cl | H | F | H | Cl |
| 243 | $SCBrF_2$ | $SCH_3$ | H | Cl | H | F | H | Cl |
| 244 | $SCBrClF$ | Br | H | Cl | H | F | H | Cl |
| 245 | $SCBrClF$ | Cl | H | Cl | H | F | H | Cl |
| 246 | $SCBrClF$ | Br | H | Cl | H | H | H | Cl |
| 247 | $SCF_2CCl_2F$ | Br | H | Cl | H | F | H | Cl |
| 248 | $SCF_2CHF_2$ | Br | H | Cl | H | F | H | Cl |
| 249 | $SCCl_2F$ | $SCH_3$ | H | F | H | Cl | H | Cl |
| 250 | $SCHBrF$ | $SCH_3$ | H | Cl | H | F | H | Cl |
| 251 | $SCBrF_2$ | Br | H | Cl | H | Cl | H | Cl |
| 252 | $SOCBrF_2$ | Br | H | Cl | H | Cl | H | Cl |
| 253 | $SO_2CBrF_2$ | Br | H | Cl | H | Cl | H | Cl |
| 254 | $SCCl_2F$ | Br | H | F | H | Cl | H | Cl |
| 255 | $SO_2CCl_2F$ | Br | H | F | H | Cl | H | Cl |
| 256 | $SOCCl_2F$ | Br | H | F | H | Cl | H | Cl |

The following EXAMPLES 1 to 268 further illustrate some of the more preferred compounds of formula (I) and (II) of the invention that were prepared. Details of typical methods of synthesis utilized in the preparation of intermediates and compounds of the invention are specifically provided below for compounds of EXAMPLES 1 to 10. The other compounds were prepared using similar methods of synthesis or modifications thereof of the detailed procedures as applicable to a given compound. These compound examples are listed in TABLE 2A (EXAMPLES 11 to 164), TABLE 2B (EXAMPLES 165-256) or TABLE 2C (EXAMPLES 257-268), wherein the compounds are grouped by the phenyl ring substitution shown below; $R_1$, n, Y, and Z are as defined. Reported melting points for compounds represent the average value of an observed melting point range determined for a compound or furthermore represent the average value of a number of separate melting point determinations. Additionally, one or more spectroscopic analyses (IR, NMR, GC/MS, etc.) have been performed on each compound for characterization and confirmation of the chemical structure.

| | PHENYL RING SUBSTITUTION IN TABLE 2A, 2B OR 2C | | |
|---|---|---|---|
| GROUP | $R_2$ | $R_4$ | $R_6$ |
| 1 | Cl | $CF_3$ | Cl |
| 2a | $SCH_3$ | $CF_3$ | Cl |
| 2b | $SC_2H_5$ | $CF_3$ | Cl |
| 2c | $SOCH_3$ | $CF_3$ | Cl |
| 2d | $SO_2CH_3$ | $CF_3$ | Cl |
| 3 | H | $CF_3$ | Cl |
| 4a | Cl | Cl | Cl |
| 4b | Cl | Br | Cl |
| 4c | Br | Cl | Cl |
| 4d | Br | F | Br |
| 4e | Cl | F | Cl |
| 5a | Cl | $OCF_3$ | Cl |
| 5b | Br | $OCF_3$ | Br |
| 5c | Br | $OCF_3$ | Cl |
| 6 | $C(CH_3)_3$ | Cl | H |

EXAMPLE 1

Preparation of
1-(2,6-dichloro-4-trifluoromethylphenyl)-5-amino-4-trifluoromethylsulfenylimidazole Process SCHEME I a) Preparation of intermediate: ethyl N-(2,6-dichloro-4-trifluoromethylphenyl)formimidate To 1.09 g (4.6 mmole) of 2,6-dichloro-4-trifluoromethylaniline was added conc. HCl (0.46 mmole) and 1.04 g (7.0 mmole) of triethylorthoformate. The resulting mixture was stirred and then it was heated to 85° C. and evaporated under vacuum. The residue was analyzed by $^1$H NMR which indicated the desired structure-$^1$H NMR (CDCl$_3$): δ1.42 (t, J=7.0 Hz, 3H), 4.47 (q, J=7.0 Hz, 2H), 7.57 (s, 3H). This compound was used in the next step without further purification.

b) Preparation of intermediate: cyanomethyl N-(2,6-dichloro-4-trifluoromethylphenyl)formimidine To a solution of 20.20 g (0.218 mole) of aminoacetonitrile hydrochloride in 500 ml of methanol was added at 0° C. 11.79 g (0.218 mole) of sodium methoxide. The mixture was stirred at RT for 30 min. and then evaporated to dryness under vacuum. The residue was extracted twice with 400 ml of diethyl ether and the ethereal solution was added to 62.45 g (0.218 mole) of ethyl N-(2,6-dichloro-4-trifluoromethylphenyl)formimidate at RT. The solvent was evaporated, 400 ml of tetrahydrofuran was added, and the mixture was heated to reflux for 18 h. The solvent was then evaporated and the residue partitioned between water and methylene chloride. The organic layer was dried over anhydrous sodium sulfate and the solvent was evaporated. The residue was finally purified by flash column chromatography using 20% ethyl acetate in hexane, followed by elution with 30% ethyl acetate in hexane to give 24 g (37.25% yield) of the desired product. $^1$H NMR (CDCl$_3$): δ4.40 (s, 2H), 7.55 (s, 2H), 7.59 (s, 1H).

c) Preparation of intermediate: 1-(2,6-dichloro-4-trifluoromethylphenyl)-5-aminoimidazole To a solution of 4.4 g (14.91 mmole) of cyanomethyl N-(2,6-dichloro-4-trifluoromethylphenyl)formimidine in 400 ml of methanol was added 81 mg (14.91 mmole) of sodium methoxide at 4° C. The mixture was stirred at RT for 3 h. The mixture was then evaporated to dryness to give the desired product (100% yield)-$^1$HNMR (CDCl$_3$/acetone-d$_6$): δ3.43 (s, 2H), 6.68 (s, 1H), 7.28 (s, 1H), 7.88 (2H).

d) Preparation of 1-(2,6-dichloro-4-trifluoromethylphenyl)-5-amino-4-trifluoromethylsulfenylimidazole To a solution of 4.8 g (14.91 mmole) of 1-(2,6-dichloro-4-trifluoromethylphenyl)-5-aminoimidazole in 400 ml of methylene chloride was added 1.3 ml (14.91 mmole) of trifluoromethanesulfenyl chloride at 0° C. The mixture was stirred at 0° C. for 4 h and then at RT for 15 h. Water was added and the mixture was partitioned between water and methylene chloride. The organic layer was dried over anhydrous sodium sulfate and the solvent removed. The residue was recrystallized from methylene chloride to give 3.36 g (52.51% yield) of the desired product., mp 134° C.

Anal.: C$_{11}$H$_5$Cl$_2$F$_6$N$_3$S.
Calc.: C, 33.35; H, 1.27; N, 10.61; S 8.09.
Found: C, 33.54; H, 1.20; N, 10.67; S 8.37.

EXAMPLE 2

Preparation of
1-(2,6-dichloro-4-trifluoromethylphenyl)-5-amino-2-chloro-4-trifluoromethylsulfenylimidazole To a solution of 6.0 g (15.15 mmole) of 1-(2,6-dichloro-4-trifluoromethylphenyl)-5-amino-4-trifluoromethylsulfenylimidazole in 100 ml of methylene chloride was added 1.70 ml (18.18 mmole) of sulfuryl chloride at 0° C. The resulting mixture was stirred at RT for 5 days under a nitrogen atmosphere. The mixture was quenched with water, then partitioned between methylene chloride and aqueous sodium bicarbonate. The organic layer was dried over anhydrous sodium sulfate and the solvent was removed. The residue was purified by column chromatography using 20% ethyl acetate in hexane to give 1.9 g (31.62% yield) of the desired product, mp 172.5° C.

EXAMPLE 3

Preparation of
1-(2,6-dichloro-4-trifluoromethylphenyl)-2-chloro-4-trifluoromethylsulfenylimidazole To a solution of 2.0 g (4.64 mmole) of 1-(2,6-dichloro-4-trifluoromethylphenyl)-5-amino-2-chloro-4-trifluoromethylsulfenylimidazole in 40 ml of tetrahydrofuran was added 2.76 ml (23.2 mmole) of t-butylnitrite. The resulting mixture was heated to reflux under a nitrogen atmosphere for 2 h. The mixture was evaporated to dryness and the residue was purified by column chromatography using 10% ethyl acetate in hexane to give 1.6 g (83.0% yield) of the desired product, mp 112° C.

Anal.: C$_{11}$H$_3$Cl$_3$F$_6$N$_2$S.
Calc.: C, 31.79; H, 0.73; N, 6.74; F, 27.43.
Found: C, 31.71; H, 0.68; N, 6.75; F, 27.65.

EXAMPLE 4

Preparation of
1-(2,6-dichloro-4-trifluoromethylphenyl)-2-chloro-4-trifluoromethylsulphinylimidazole To a solution of 800 mg (1.93 mmole) of 1-(2,6-dichloro-4-trifluoromethylphenyl)-2-chloro-4-trifluoromethylsulfenylimidazole in trifluoroacetic acid was added 0.20 ml of 30% hydrogen peroxide at 0° C. The resulting mixture was stirred at 0° C. for 4 h and then at RT for 50 h. The mixture was evaporated at RT and the residue was partitioned between methylene chloride and a saturated aqueous sodium bisulfite solution. The organic layer was washed with an aqueous sodium bicarbonate solution and the organic layer was evaporated. The residue was purified by flash column chromatography on silica gel using 5% ethyl acetate in hexane. After the solvent was removed there was obtained 300 mg (36.02% yield) of the desired product as a white solid, mp 147.5° C.

Anal.: C$_{11}$H$_3$Cl$_3$F$_6$N$_2$OS.
Calc.: C, 30.61; H, 0.70; N, 6.49; Cl, 24.64; F, 26.41; S, 7.43
Found: C, 30.63; H, 0.83; N, 6.48; Cl, 24.83; F, 26.53; S, 7.78.

EXAMPLE 5

Preparation of
1-(2,6-dichloro-4-trifluoromethylphenyl)-2-chloro-4-trifluoromethylsulfonylimidazole To a solution of 300 mg (0.72 mmole) of 1-(2,6-dichloro-4-trifluoromethylphenyl)-2-chloro-4-trifluoromethylsulfenylimidazole in 5 ml of trifluoroacetic acid was added 0.15 ml (1.44 mmole) of 30% hydrogen peroxide at 0° C. The resulting mixture was stirred at RT for 4 days. The mixture was evaporated to remove trifluoroacetic acid and the residue was partitioned between methylene chloride and a saturated aqueous sodium bisulfite solution. The organic layer was washed with an aqueous sodium bicarbonate solution. The organic layer was dried over anhydrous sodium sulfate and the solvent was removed. The residue was purified by preparative TLC using 100% methylene chloride to give 190 mg (59.03% yield) of the desired product as white solid, mp 182.5° C.

EXAMPLE 6

Preparation of
1-(2,6-dichloro-4-trifluoromethylphenyl)-2-chloro-5-methylsulfenyl-4-trifluoromethylsulfenylimidazole To a solution of 700 mg (1.77 mmole) of 1-(2,6-dichloro-4-trifluoromethylphenyl)-5-amino-2-chloro-4-trifluoromethylsulfenylimidazole in 8 ml of chloroform was added 0.26 ml (2.54 mmole) of dimethyl disulfide and 0.32 ml (0.89 mmole) of t-butylnitrite at 0° C. The resulting mixture was stirred at 0° C. for 15 min. and then at RT for 45 min. The mixture was diluted with 75 ml of methylene chloride and partitioned between water and methylene chloride. The organic layer was dried over anhydrous sodium sulfate and the solvent was evaporated. The residue was purified by preparative TLC using 5% ethyl acetate in hexane to give 480 mg (58.74% yield) of the desired product. $^1$H NMR (CDCl$_3$): δ2.26 (s, 3H), 7.82 (s, 2H).

EXAMPLE 7

Preparation of
1-(2,6-dichloro-4-trifluoromethylphenyl)-5-amino-2-bromo-4-trifluoromethylsulfenylimidazole To a solution of 1.35 g (3.40 mmole) of 1-(2,6-dichloro-4-trifluoromethylphenyl)-5-amino-4-trifluoromethylsulfenylimidazole in 20 ml of chloroform was added 0.5 ml (9.76 mmole) of bromine. The resulting mixture was stirred at RT under a nitrogen atmosphere for 2 hr. The mixture was then evaporated to remove the excess of bromine and the residue was partitioned between water and methylene chloride. The organic layer was dried over anhydrous sodium sulfate and solvent was removed. The residue was purified by flash column chromatography on silica gel using 7% ethyl acetate in hexane to give 200 mg (13.62% yield) of the desired product, mp 154° C.

EXAMPLE 8

Preparation of
1-(2,6-dichloro-4-trifluoromethylphenyl)-5-bromo-4-trifluoromethylsulfenylimidazole To a solution of 2.0 g (5.05 mmole) of 1-(2,6-dichloro-4-trifluoromethylphenyl)-5-amino-4-trifluoromethylsulfenylimidazole in 10 ml of acetonitrile was added 1 ml of bromoform and 1.20 ml (10.10 mmole) of t-butylnitrite at 0° C. The resulting mixture was stirred at RT under a nitrogen atmosphere for 1.5 h. Ten ml of toluene was added and the mixture was evaporated to dryness under vacuum. The residue was purified by column chromatography on silica gel using 5% ethyl acetate in hexane to give 800 mg (34.44% yield) of the desired product, mp 87.5° C.

Anal.: C$_{11}$H$_3$BrCl$_2$F$_6$N$_2$S.
Calc.: C, 28.72; H, 0.66; N, 6.09; F, 24.78; S, 6.97.
Found: C, 29.06; H, 0.69; N, 6.20; F, 24.2; S, 7.48.

EXAMPLE 9

Preparation of
1-(6-chloro-2-methylsulfenyl-4-trifluoromethylphenyl)-2-bromo-4-chlorodifluoromethylsulfonylimidazole To a solution of 500 mg (0.984 mmole) of 1-(2,6-dichloro-4-trifluoromethylphenyl)-2-bromo-4-chlorodifluoromethylsulfonyl-imidazole in 2 ml of tetrahydrofuran was added a solution of 69 mg (0.984 mmole) of sodium methanethiolate in 0.3 ml of water. The resulting mixture was stirred at RT for 14 hours, after which it was partitioned between water and diethyl ether. The organic layer was separated, dried over anhydrous sodium sulfate and stripped of solvent. The residue was purified by preparative TLC using 20% ethyl acetate in hexane to give 180 mg (35% yield) of the product, mp 116° C.

EXAMPLE 10

Preparation of
1-(2,6-dichloro-4-trifluoromethylphenyl)-2-methyl-4-chlorodifluoromethylsulfenylimidazole a) Preparation of intermediate: N-acetyl-2,6-dichloro-4-trifluoromethylaniline To 10.6 g (0.26 mole) of dry potassium hydride in THF (150 ml) was added 20 g (87.3 mmole) of 2,6-dichloro-4-trifluoromethylaniline at 0° C. under a nitrogen atmosphere. The resulting mixture was stirred and warmed to room temperature for 3.5 h. The mixture was cooled to 0° C. and 6.6 ml (92.8 mmole) of acetyl chloride was added dropwise. The mixture was stirred at 0° C. for 30 min. The mixture was warmed to room temperature under a nitrogen atmosphere overnight. The mixture was quenched with satd. NH$_4$Cl (150 ml). The mixture was evaporated to remove THF and the suspension was filtered and the solid washed with hexane, followed by a wash with dichloromethane to give 14.5 g (61%) of the desired product. $^1$H NMR, (CDCl$_3$/CD$_3$OD): δ2.12(s, 3H), 7.60(s,2H).

b) Preparation of intermediate: 1-chloro-1-methyl-N-(2,6-dichloro-4-trifluoromethylphenyl)formimine To a suspension of 4.3 g (15.8 mmole) of N-acetyl-2,6-dichloro-4-trifluoromethylaniline in 50 ml of chloroform was added 3.3 g (15.8 mmole) of phosphorous pentachloride at RT. The mixture was heated to reflux under a nitrogen atmosphere for 1 h. The mixture was evaporated to dryness. To the residue was added 50 ml of benzene. The resulting mixture was heated to reflux for 1 h. under a nitrogen atmosphere. The mixture was evaporated to dryness and the residue purified by a column chromatography on silica gel using 10% ethyl acetate in hexane to yield 4.3 g (93.7% yield) of the desired product as an oil. $^1$H NMR, (CDCl$_3$): δ2.70(s, 3H), 7.58(s, 2H).

c) Preparation of intermediate: 1-(2,6-dichloro-4-trifluoromethylphenyl)-5-amino-2-methylimidazole To a solution of 9.6 g (33.0 mmole) of 1-chloro-1-methyl-N-(2,6-dichloro-4-trifluoromethylphenyl)formimine in 300 ml of chloroform was added 3.7 g (66.0 mmole) of aminoacetonitrile at RT. The resulting mixture was heated to reflux under a nitrogen atmosphere for 60 h. The reaction mixture was used in the following step without purification. The $^1$H NMR spectrum indicated approximately 60% conversion based on the starting iminochloride. $^1$H NMR, (CDCl$_3$): δ2.13(s, 3H), 6.58(s, 1H), 7.76(s, 2H).

d) Preparation of 1-(2,6-dichloro-4-trifluoromethylphenyl)-5-amino-2-methyl-4-chlorodifluoromethylsulfenylimidazole To the reaction mixture, described above in (c), was added 5.8 ml (57.7 mmole) of chlorodifluoromethanesulfenyl chloride at RT. The mixture was stirred at RT for 3.5 h. The mixture was quenched with water. The mixture was partitioned between water and dichloro methane. The organic layer was dried over anhydrous sodium sulfate and the solvent evaporated to give the desired product. The crude product was used in the following step without further purification.

e) Preparation of the 1-(2,6-dichloro-4-trifluoromethylphenyl)-2-methyl-4-chlorodifluoromethylsulfenylimidazole To the crude product, described above in (d), was added 100 ml of THF, followed by addition of 19.6 ml (165 mmole) of t-butylnitrite. The mixture was stirred at RT under a nitrogen atmosphere with protection from light overnight. The mixture was evaporated to dryness. The residue was purified by a flash column chromatography using 10% ethyl acetate in hexane to give 1.3 g (9.46% yield from the imino chloride, described in (b)) of the desired product, mp 118.5° C.

TABLE 2A
ADDITIONAL SYNTHESIZED IMIDAZOLE COMPOUNDS OF FORMULA (I) AND (II)

| CMPD. OF EXAMPLE | $R_1$ | n | Y | Z | M.P., °C |
|---|---|---|---|---|---|
| Group 1: $R_2$ and $R_6$ are Cl, and $R_4$ is $CF_3$ | | | | | |
| 11 | $CF_3$ | 0 | H | H | 63.5 |
| 12 | $CF_3$ | 0 | Cl | H | 82.5 |
| 13 | $CF_3$ | 0 | $SCH_3$ | H | 85.5 |
| 14 | $CF_3$ | 0 | Cl | Cl | OIL |
| 15 | $CClF_2$ | 0 | $NH_2$ | H | 166.5 |
| 16 | $CClF_2$ | 0 | N=CHOC$_2$H$_5$ | H | OIL |
| 17 | $CCl_2F$ | 0 | $NH_2$ | H | 177 |
| 18 | $CCl_2F$ | 0 | Br | H | 105.5 |
| 19 | $CCl_2F$ | 0 | $SCH_3$ | H | 99 |
| 20 | $CCl_2F$ | 0 | H | Cl | 120 |
| 21 | $CCl_2F$ | 0 | Cl | Cl | OIL |
| 22 | $CCl_2F$ | 0 | $NH_2$ | Cl | 176 |
| 23 | $CCl_2F$ | 0 | H | Br | 123 |
| 24 | $CCl_2F$ | 0 | $NH_2$ | Br | 133 |
| 25 | $CF_3$ | 1 | H | H | 98 |
| 26 | $CF_3$ | 2 | H | H | 170.5 |
| 27 | $CF_3$ | 2 | Br | H | 152.5 |
| 28 | $CCl_2F$ | 1 | H | Cl | 171 |
| 29 | $CCl_2F$ | 1 | H | Br | 181.5 |
| 30 | $CCl_2F$ | 2 | Br | H | 175.5 |
| 31 | $CCl_2F$ | 2 | H | Cl | 171 |
| 32 | $CCl_2F$ | 2 | H | Br | 180.5 |
| 33 | $CClF_2$ | 1 | H | Br | 155.5 |
| 34 | $CClF_2$ | 2 | H | Br | 160.5 |
| 35 | $CClF_2$ | 0 | H | Br | 104.5 |
| 36 | $CClF_2$ | 0 | H | Cl | 92.5 |
| 37 | $CClF_2$ | 1 | H | Cl | 145.5 |
| 38 | $CClF_2$ | 2 | H | Cl | 159.5 |
| 39 | $CCl_2F$ | 1 | $SO_2CH_3$ | H | 162.5 |
| 40 | $CCl_2F$ | 1 | $SOCH_3$ | H | OIL |
| 41 | $CClF_2$ | 0 | H | H | 69.5 |
| 42 | $CCl_2F$ | 0 | H | H | 67.5 |
| 43 | $CF_3$ | 0 | H | $SCH_3$ | OIL |
| 44 | $CCl_2F$ | 1 | H | H | 141.5 |
| 45 | $CCl_2F$ | 2 | H | H | 188 |
| 46 | $CCl_2F$ | 0 | H | $SCH_3$ | OIL |
| 47 | $CClF_2$ | 2 | H | H | 164 |
| 48 | $CClF_2$ | 1 | H | H | 109.5 |
| 49 | $CCl_2F$ | 0 | H | $SCH(CH_3)_2$ | OIL |
| 50 | $CCl_2F$ | 0 | H | $SOCH(CH_3)_2$ | OIL |
| 51 | $CCl_2F$ | 1 | H | $SOCH(CH_3)_2$ | 148 |
| 52 | $CCl_2F$ | 1 | H | $SOCH(CH_3)_2$ | 149 |
| 53 | $CH_3$ | 0 | H | $SCH_3$ | 85 |
| 54 | $CH_3$ | 0 | H | H | OIL |
| 55 | $CH_3$ | 1 | H | H | 129.5 |
| 56 | $CH_3$ | 2 | H | H | 220.5 |
| 57 | $CH(CH_3)_2$ | 1 | H | H | 170.5 |
| 58 | $CH(CH_3)_2$ | 2 | H | H | 206.5 |
| 59 | $CCl_2F$ | 0 | H | $CH_3$ | 129 |
| 60 | $CCl_2F$ | 1 | H | $CH_3$ | 154 |
| 61 | $CCl_2F$ | 2 | H | $CH_3$ | 198 |
| 62 | COMPOUND DELETED | | | | |
| 63 | $CCl_2F$ | 0 | H | $CF_3$ | 88.5 |
| 64 | $CCl_2F$ | 1 | H | $CF_3$ | 139.5 |
| 65 | $CF_3$ | 0 | H | $CH_3$ | 127.5 |

TABLE 2A-continued
ADDITIONAL SYNTHESIZED IMIDAZOLE COMPOUNDS OF FORMULA (I) AND (II)

| CMPD. OF EXAMPLE | $R_1$ | n | Y | Z | M.P., °C. |
|---|---|---|---|---|---|
| 66 | $CF_3$ | 1 | H | $CH_3$ | 140.5 |
| 67 | $CF_3$ | 2 | H | $CH_3$ | 180.5 |
| 68 | $CClF_2$ | 1 | H | $CH_3$ | 143.5 |
| 69 | $CClF_2$ | 2 | H | $CH_3$ | 172.5 |
| Group 2a: $R_2$ is $SCH_3$, $R_6$ is Cl, and $R_4$ is $CF_3$ | | | | | |
| 70 | $CCl_2F$ | 2 | H | Cl | OIL |
| 71 | $CCl_2F$ | 0 | H | Cl | OIL |
| 72 | $CCl_2F$ | 1 | H | Cl | 136 |
| 73 | $CClF_2$ | 0 | H | Cl | OIL |
| 74 | $CF_3$ | 0 | H | Cl | OIL |
| Group 2b: $R_2$ is $SC_2H_5$, $R_6$ is Cl, and $R_4$ is $CF_3$ | | | | | |
| 75 | $CCl_2F$ | 0 | H | Cl | OIL |
| Group 2c: $R_2$ is $SOCH_3$, $R_6$ is Cl, and $R_4$ is $CF_3$ | | | | | |
| 76 | $CClF_2$ | 2 | H | Cl | OIL |
| *77 | $CF_3$ | 0 | H | Cl | 192.5 |
| *78 | $CF_3$ | 0 | H | Cl | 112.5 |
| Group 2d: $R_2$ is $SO_2CH_3$, $R_6$ is Cl, and $R_4$ is $CF_3$ | | | | | |
| 79 | $CClF_2$ | 2 | H | Cl | OIL |
| Group 3: $R_2$ is H, $R_6$ is Cl and $R_4$ is $CF_3$ | | | | | |
| 80 | $CCl_2F$ | 0 | H | H | OIL |
| 81 | $CCl_2F$ | 1 | H | H | 109.5 |
| 82 | $CCl_2F$ | 0 | Cl | H | OIL |
| 83 | $CCl_2F$ | 1 | H | Cl | 111 |
| 84 | $CF_3$ | 0 | H | H | OIL |
| 85 | $CF_3$ | 0 | H | Br | 117 |
| 86 | $CF_3$ | 1 | H | H | 87.5 |
| 87 | $CF_3$ | 2 | H | H | 137 |
| 88 | $CCl_2F$ | 0 | Br | Br | 108.5 |
| Group 4a: $R_2$, $R_4$, and $R_6$ are Cl | | | | | |
| 89 | $CCl_2F$ | 1 | $NH_2$ | H | 209 |
| 90 | $CCl_2F$ | 0 | H | Cl | 117.5 |
| 91 | $CClF_2$ | 0 | H | H | 47 |
| 92 | $CCl_2F$ | 0 | H | H | 67 |
| 93 | $CClF_2$ | 2 | H | H | 141 |
| 94 | $CCl_2F$ | 2 | H | H | 159.5 |
| 95 | $CCl_2F$ | 1 | H | H | 93.5 |
| 96 | $CClF_2$ | 1 | H | H | 87.5 |
| 97 | $CF_3$ | 0 | H | H | 65.5 |
| 98 | $CF_3$ | 1 | H | H | 101 |
| 99 | $CF_3$ | 2 | H | H | 129.5 |
| 100 | $CF_3$ | 0 | $NH_2$ | H | 144 |
| 101 | $CF_3$ | 0 | H | H | 65.5 |
| 102 | $CF_3$ | 1 | H | H | 101 |
| 103 | $CF_3$ | 2 | H | H | 129.5 |
| Group 4b: $R_2$ and $R_6$ are Cl and $R_4$ is Br | | | | | |
| 104 | $CCl_2F$ | 0 | H | H | 72 |
| 105 | $CCl_2F$ | 0 | $NH_2$ | H | 202.5 |
| 106 | $CCl_2F$ | 1 | H | H | 129.5 |
| 107 | $CCl_2F$ | 2 | H | H | 175 |
| 108 | $CClF_2$ | 0 | $NH_2$ | H | 154 |
| 109 | $CClF_2$ | 0 | H | H | 47 |
| 110 | $CClF_2$ | 2 | H | H | 156.5 |
| 111 | $CClF_2$ | 1 | H | H | 101 |
| 112 | $CF_3$ | 0 | H | H | 68 |
| 113 | $CF_3$ | 1 | H | H | 115.5 |
| 114 | $CF_3$ | 2 | H | H | 144 |
| 115 | $CF_3$ | 0 | $NH_2$ | H | 161.5 |
| 116 | COMPOUND DELETED | | | | |
| 117 | COMPOUND DELETED | | | | |
| 118 | COMPOUND DELETED | | | | |
| Group 5a: $R_2$ and $R_6$ are Cl and $R_4$ is $OCF_3$ | | | | | |
| 119 | $CCl_2F$ | 0 | $NH_2$ | H | OIL |
| 120 | $CCl_2F$ | 0 | H | H | OIL |
| 121 | $CCl_2F$ | 1 | H | H | 108.5 |
| 122 | $CF_3$ | 0 | $NH_2$ | H | 111 |
| 123 | $CF_3$ | 0 | $NH_2$ | Br | 115 |
| 124 | $CF_3$ | 0 | H | H | OIL |
| 125 | $CF_3$ | 0 | H | Br | 85.5 |
| 126 | $CClF_2$ | 0 | $NH_2$ | H | 112 dec. |
| 127 | $CF_3$ | 2 | H | H | 127.5 |
| 128 | $CF_3$ | 1 | H | H | 65 |
| 129 | $CF_3$ | 1 | H | Br | 137 |
| 130 | $CClF_2$ | 0 | H | H | OIL |
| 131 | $CClF_2$ | 1 | H | H | 59.5 |
| 132 | $CF_3$ | 2 | H | Br | 138.5 |

TABLE 2A-continued

ADDITIONAL SYNTHESIZED IMIDAZOLE COMPOUNDS OF FORMULA (I) AND (II)

| CMPD. OF EXAMPLE | $R_1$ | n | Y | Z | M.P., °C. |
|---|---|---|---|---|---|
| 133 | $CClF_2$ | 0 | $NH_2$ | Br | 157 |
| 134 | $CClF_2$ | 2 | H | H | 130.5 |
| 135 | $CClF_2$ | 0 | H | Br | 112 |
| 136 | $CClF_2$ | 2 | H | Br | 156 |
| 137 | $CClF_2$ | 0 | $N=CHOC_2H_5$ | Br | OIL |
| 138 | $CClF_2$ | 1 | H | Br | 158 |
| 139 | $CCl_2F$ | 0 | $NH_2$ | Cl | 179 |
| 140 | $CCl_2F$ | 0 | H | Cl | 141 |
| 141 | $CClF_2$ | 0 | $NHCH_3$ | Br | 108 |
| 142 | $CCl_2F$ | 1 | H | Cl | 185 |
| 143 | $CCl_2F$ | 2 | H | H | 122 |
| 144 | $CCl_2F$ | 0 | $NH_2$ | Br | 177.5 |
| 145 | $CCl_2F$ | 0 | H | Br | 141.5 |
| 146 | $CCl_2F$ | 1 | H | Br | 181 |
| 147 | $CCl_2F$ | 2 | H | Br | 188 |
| 148 | $CCl_2F$ | 2 | H | Cl | 185.5 |
| 149 | $CH_3$ | 0 | H | H | 60.5 |
| 150 | $CH_3$ | 2 | H | H | 171 |
| 151 | $CH_3$ | 1 | H | H | 131 |
| Group 5b: $R_2$ and $R_6$ are Br and $R_4$ is $OCF_3$ | | | | | |
| 152 | $CCl_2F$ | 0 | $NH_2$ | H | 141 |
| 153 | $CCl_2F$ | 0 | H | H | OIL |
| 154 | $CCl_2F$ | 1 | H | H | 115 |
| 155 | $CCl_2F$ | 2 | H | H | 124.5 |
| 156 | $CClF_2$ | 0 | $NH_2$ | H | 135 |
| 157 | $CClF_2$ | 0 | H | H | 51 |
| 158 | $CClF_2$ | 2 | H | H | 146.5 |
| 159 | $CClF_2$ | 1 | H | H | 103.5 |
| 160 | $CClF_2$ | 1 | $NH_2$ | H | 135 dec. |
| Group 5c: $R_2$ is Br, $R_6$ is Cl, and $R_4$ is $OCF_3$ | | | | | |
| 161 | $CCl_2F$ | 0 | $NH_2$ | H | 150 |
| 162 | $CCl_2F$ | 0 | H | H | 68.5 |
| 163 | $CCl_2F$ | 1 | H | H | 87 |
| 164 | $CCl_2F$ | 2 | H | H | 142.5 |

*isomeric compounds

TABLE 2B

ADDITIONAL SYNTHESIZED IMIDAZOLE COMPOUNDS OF FORMULA (I) AND (II)

| COMPD. OF EXAMPLE | $R_1$ | n | Y | Z | M.P., °C. |
|---|---|---|---|---|---|
| Group 1: $R_2$ and $R_6$ are Cl, and $R_4$ is $CF_3$ | | | | | |
| 165 | $CF_3$ | 0 | H | $COCH_3$ | 82.5 |
| 166 | $CF_3$ | 0 | $NH_2$ | $CONH_2$ | 156 |
| 167 | $CF_3$ | 0 | $NH_2$ | $COCH_3$ | 151.5 |
| 168 | $CF_3$ | 0 | $NH_2$ | $CH_3$ | 147.5 |
| 169 | $CF_3$ | 0 | $NH_2$ | CN | 86.5 |
| 170 | $CClF_2$ | 0 | H | CN | 83.5 |
| 171 | $CClF_2$ | 1 | H | CN | 119.5 |
| 172 | $CClF_2$ | 0 | H | $CONH_2$ | 155.5 |
| 173 | $CCl_2F$ | 0 | H | CN | 85 |
| 174 | $CCl_2F$ | 0 | Br | $CH_3$ | OIL |
| 175 | $CCl_2F$ | 1 | Br | $CH_3$ | 149 |
| 176 | $CCl_2F$ | 0 | $SCH_3$ | $CH_3$ | 98.5 |
| 177 | $CCl_2F$ | 2 | Br | $CH_3$ | 177 |
| 178 | $CClF_2$ | 0 | $SCH_3$ | Cl | OIL |
| 179 | $CClF_2$ | 0 | $SC(CH_3)_3$ | $CH_3$ | 124 |
| Group 3: $R_2$ is H, $R_6$ is Cl, and $R_4$ is $CF_3$ | | | | | |
| 180 | CHClF | 1 | H | H | 111 |
| 181 | $CF_3$ | 0 | H | Cl | 106.5 |
| 182 | $CF_3$ | 0 | H | Cl | 140 |
| 183 | $CF_3$ | 2 | H | Cl | 119 |
| 184 | $CF_3$ | 0 | H | Br | 119 |
| 185 | $CF_3$ | 1 | H | Br | 153 |
| 186 | $CF_3$ | 2 | H | Br | 120 |
| 187 | $CCl_2F$ | 0 | Cl | H | 110.5 |
| 188 | $CCl_2F$ | 1 | Cl | H | 109.5 |
| 189 | $CCl_2F$ | 0 | Br | H | 116 |
| 190 | $CCl_2F$ | 1 | Br | H | 145 |
| 191 | $CCl_2F$ | 2 | Br | H | 146 |
| 192 | $CCl_2F$ | 0 | $SCH_3$ | H | 92 |
| 193 | $CCl_2F$ | 0 | Br | $CH_3$ | 119 |
| 194 | $CCl_2F$ | 1 | Br | $CH_3$ | 158 |

TABLE 2B-continued

ADDITIONAL SYNTHESIZED IMIDAZOLE COMPOUNDS OF FORMULA (I) AND (II)

| COMPD. OF EXAMPLE | $R_1$ | n | Y | Z | M.P., °C. |
|---|---|---|---|---|---|
| 195 | $CCl_2F$ | 2 | Br | $CH_3$ | 178 |
| 196 | $CCl_2F$ | 0 | H | $CH_3$ | 116 |
| 197 | $CCl_2F$ | 1 | H | $CH_3$ | 141 |
| 198 | $CCl_2F$ | 2 | H | $CH_3$ | 129 |
| 199 | $CClF_2$ | 0 | Br | H | 77.5 |
| 200 | $CClF_2$ | 1 | Br | H | 159.5 |
| 201 | $CClF_2$ | 0 | Cl | H | OIL |
| 202 | $CClF_2$ | 1 | Cl | H | OIL |
| 203 | $CCl_2F$ | 0 | $N=CHOC_2H_5$ | H | OIL |
| 204 | $CCl_2F$ | 1 | $N=CHOC_2H_5$ | H | OIL |
| 205 | $CCl_2F$ | 1 | $N=C(CH_3)OC_2H_5$ | H | OIL |
| 206 | $CH_3$ | 0 | Br | H | 107 |
| 207 | $CH_3$ | 1 | Br | H | 201.5 |
| 208 | $CH_3$ | 2 | Br | H | 216 |
| 209 | $CH_3$ | 0 | Cl | H | 105 |
| 210 | $CH_3$ | 1 | Cl | H | 198.5 |
| 211 | $CClF_2$ | 0 | $SCH_3$ | H | 80 |
| 212 | $CHClF$ | 0 | Cl | H | OIL |
| Group 4b: $R_2$ and $R_6$ are Cl and $R_4$ is Br | | | | | |
| 213 | $CCl_2F$ | 0 | $SCH_3$ | H | OIL |
| Group 4c: $R_2$ is Br and $R_6$ and $R_4$ are Cl | | | | | |
| 214 | $CCl_2F$ | 0 | H | H | 64 |
| 215 | $CF_3$ | 0 | H | H | 54 |
| 216 | $CCl_2F$ | 0 | Br | H | 123 |
| 217 | $CF_3$ | 0 | Br | H | 99.5 |
| 218 | $CCl_2F$ | 1 | H | H | 89 |
| 219 | $CF_3$ | 1 | H | H | 115 |
| 220 | $CCl_2F$ | 1 | Br | H | 143 |
| 221 | $CF_3$ | 1 | Br | H | 170 |
| 222 | $CCl_2F$ | 0 | $SCH_3$ | H | OIL |
| 223 | $CF_3$ | 0 | $SCH_3$ | H | 74 |
| 224 | $CCl_2F$ | 2 | Br | H | 138 |
| 225 | $CF_3$ | 2 | Br | H | 153.5 |
| Group 4d: $R_2$ and $R_6$ are Br and $R_4$ is F | | | | | |
| 226 | $CClF_2$ | 0 | Br | H | 82 |
| 227 | $CClF_2$ | 0 | $SCH_3$ | H | OIL |
| Group 4e: $R_2$ and $R_6$ are Cl and $R_4$ is F | | | | | |
| 228 | $CCl_2F$ | 0 | $SCH_3$ | H | OIL |
| 229 | $CCl_2F$ | 0 | H | H | OIL |
| 230 | $CCl_2F$ | 0 | Br | H | OIL |
| 231 | $CClF_2$ | 0 | $SCH_3$ | H | OIL |
| 232 | $CClF_2$ | 0 | H | H | 85.5 |
| 233 | $CClF_2$ | 0 | Br | H | OIL |
| 234 | $CCl_2F$ | 1 | H | H | 100 |
| 235 | $CCl_2F$ | 0 | Cl | H | OIL |
| 236 | $CCl_2F$ | 2 | H | H | 165.5 |
| 237 | $CF_3$ | 0 | H | H | 57 |
| 238 | $CF_3$ | 1 | H | H | 65 |
| 239 | $CF_3$ | 2 | H | H | 128.5 |
| 240 | $CF_3$ | 0 | Br | H | 64 |
| 241 | $CF_3$ | 0 | $SCH_3$ | H | 95.5 |
| 242 | $CF_3$ | 0 | H | H | 73.5 |
| 243 | $CF_3$ | 1 | Br | H | 158 |
| 244 | $CF_3$ | 2 | Br | H | 118.5 |
| 245 | $CF_3$ | 1 | Cl | H | 116 |
| 246 | $CCl_2F$ | 1 | H | H | 94.5 |
| 247 | $CClF_2$ | 1 | Br | H | 129.5 |
| 248 | $CClF_2$ | 2 | Br | H | 104.5 |
| 249 | $CClF_2$ | 2 | H | H | 148.5 |
| 250 | $CCl_2F$ | 1 | Br | H | 118.5 |
| 251 | $CCl_2F$ | 2 | Br | H | 129.5 |
| 252 | $CH_3$ | 0 | Br | H | 133.5 |
| Group 5a: $R_2$ and $R_6$ Cl and $R_4$ is $OCF_3$ | | | | | |
| 253 | $CCl_2F$ | 0 | H | $CH_3$ | 131 |
| 254 | $CCl_2F$ | 2 | H | $CH_3$ | 153 |
| 255 | $CCl_2F$ | 1 | H | $CH_3$ | 142 |
| Group 5b: $R_2$ and $R_6$ are Br and $R_4$ is $OCF_3$ | | | | | |
| 256 | $CClF_2$ | 1 | $N=CHOC_2H_5$ | H | OIL |

TABLE 2C

ADDITIONAL SYNTHESIZED IMIDAZOLE COMPOUNDS OF FORMULA (I) AND (II)

| CMPD. OF EXAMPLE | $R_1$ | n | Y | Z | M.P., °C |
|---|---|---|---|---|---|
| Group 1: $R_2$ and $R_6$ are Cl and $R_4$ is $CF_3$ | | | | | |
| 257 | $CClF_2$ | 0 | Br | Cl | 82.5 |
| Group 4a: $R_2$, $R_4$ and $R_6$ are Cl | | | | | |
| 258 | $CCl_2F$ | 0 | $N=C(CH_3)OCH_2H_5$ | H | 108 |
| 259 | $CCl_2F$ | 1 | $NH_2$ | H | 133 |
| 260 | $CCl_2F$ | 0 | $NHCOCH_3$ | H | 86 |
| 261 | $CCl_3$ | 0 | Br | H | OIL |
| 262 | | | COMPOUND DELETED | | |
| 263 | | | COMPOUND DELETED | | |
| 264 | $CCl_2F$ | 0 | $NHCOCF_3$ | H | 208 |
| Group 4c: $R_2$ is Br and $R_6$ and $R_4$ are Cl | | | | | |
| 265 | $CCl_2F$ | 0 | $NH_2$ | H | OIL |
| 266 | $CF_3$ | 0 | $NH_2$ | H | 155.5 |
| Group 4d: $R_2$ and $R_6$ are Br and $R_4$ is F | | | | | |
| 267 | $CClF_2$ | 0 | H | H | 54 |
| Group 6: $R_2$ is $C(CH_3)_3$, $R_6$ is H, and $R_4$ is Cl | | | | | |
| 268 | $CCl_2F$ | 0 | H | Cl | OIL |

EXAMPLE 269

Miticide, Insecticide, and Nematicide Use

The following test procedures, using the compounds of EXAMPLES 1-268, were conducted to determine the pesticidal use and activity of compounds of the invention against: mites; certain insects, including an aphids, a caterpillar, a fly, and three species of beetle larvae (two foliar feeding and the other root feeding); and nematodes. The specific species tested were as follows:

| GENUS, SPECIES | COMMON NAME | (ABBREVIATION) |
|---|---|---|
| *Tetranychus urticae* | twospotted spider mite | TSM |
| *Aphis nasturtii* | buckthorn aphid | BA |
| *Spodoptera eridania* | southern armyworm | SAW |
| *Epilachna varivestis* | Mexican bean beetle | MBB |
| *Musca domestica* | housefly | HF |
| *Diabrotica u. howardi* | southern corn rootworm | SCRW |
| *Meloidogyne incognita* | southern root-knot nematode | SRKN |
| *Leptinotarsa decemlineata* | Colorado potato beetle | CPB |
| *Aphis gossypii* | cotton aphid | CA |

Formulations

The test compounds (EXAMPLES 1-268) were formulated for use according to the following methods used for each of the test procedures.

For mite, aphid, southern armyworm, and Mexican bean beetle tests, a solution or suspension was prepared by adding 10 mg of the test compound to a solution of 160 mg of dimethylformamide, 838 mg of acetone, 2 mg of a 3:1 ratio of Triton X-172:Triton X-152 (respectively, mainly anionic and nonionic low foam emulsifiers which are each anhydrous blends of alkylaryl polyether alcohols with organic sulfonates), and 98.99 g of water. The result was a concentration of 100 ppm of the test compound.

For housefly tests, the formulation was initially prepared in a similar manner to the above, but in 16.3 g of water with corresponding adjustment of other components, providing a 200 ppm concentration. Final dilution with an equal volume of a 20% by weight aqueous solution of sucrose provided a 100 ppm concentration of the test compound. When necessary, sonication was provided to insure complete dispersion.

For southern corn rootworm tests, a solution or suspension was prepared in the same manner as that used for the initial 200 ppm concentration for housefly. Aliquots of this 200 ppm formulation were then used by dilution with water according to the required test concentration.

For southern root-knot nematode and systemic tests for southern armyworm, Colorado potato beetle and cotton aphid, a stock solution or suspension was prepared by adding 15 mg of the test compound to 250 mg of dimethylformamide, 1250 mg of acetone and 3 mg of the emulsifier blend referenced above. Water was then added to bring the total volume to 45 ml and a test compound concentration of 333 ppm. When necessary, sonication was provided to insure complete dispersion.

Test Procedures

The above formulated test compounds were then evaluated for their pesticidal activity at the specified concentrations, in ppm (parts per million) by weight, according to the following test procedures:

Twospotted spider mite: Leaves infested with adult and nymphal stages of the two-spotted spider mite, obtained from a stock culture were placed on the primary leaves of two bean plants growing in a 6 cm. peat pot. A sufficient number of mites (150-200) for testing were transferred to the fresh plants within a period of twenty-four hours. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, either dicofol or hexythiazox, formulated in the same manner, was tested as a standard. The sprayed plants were held for six days, after which a mortality count of motile forms was made.

Twospotted spider mite (ovicide test): Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

Buckthorn aphid: Adult and nymphal stages of buckthorn aphid were reared on potted dwarf nasturtium plants. The potted plants (one pot per compound tested) infested with 100–150 aphids, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on infested plants. A treated control with a commercial technical compound, malathion, formulated in the same manner, was tested as a standard. After spraying, the pots were stored for one day after which the dead aphids were counted.

Southern armyworm: Potted bean plants, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar southern armyworm larvae were introduced into each cup which was closed and held for five days. Larvae which were unable to move the length of the body, even upon stimulation by prodding, were considered dead.

Southern armyworm and Colorado potato beetle on tomato-systemic evaluation: This test was conducted in conjunction with the southern root-knot nematode evaluation (discussed below). The tomato plants, grown in the soil (at an initial compound test screening rate of 13.2 ppm soil concentration or about 150 ppm solution concentration) for nematode evaluation, were then utilized for evaluation of a compound's uptake via roots and subsequent systemic transport to the tomato foliage. At the termination of the nematode test, the tomato foliage was excised, placed into a plastic container, and infested with second instar larvae of southern armyworm. After about 5 days, the larvae were examined for percent mortality. Foliage which was sufficiently lethal for SAW was then feed to second instar larvae of Colorado potato beetle. After about 2 days, the larvae were examined for percent mortality.

Southern armyworm on snapbean-systemic evaluation: The stock solution of the compound was as prepared as in the above systemic test and diluted, as appropriate to deliver 25 ml of a 25 ppm soil concentration dose as a drench to 10 cm pots containing snapbean plants. After holding the plants about 3, 7 and 14 days, the foliage was excised, placed in a plastic container, and infested with second instar larvae of southern armyworm. After about 5 days, the larvae were examined for percent mortality.

Southern armyworm and cotton aphid on cotton and sorghum-systemic evaluation: The stock solution of the compound was prepared as in the above systemic tests and diluted, as appropriate, to deliver 5 ml of a 10 ppm soil concentration dose as a drench to 6 cm pots containing cotton and sorghum plants. The cotton plants were previously infested with cotton aphids about 2 day before treatment. After holding the plants about 4 days, the cotton aphids were counted and mortality was assessed. The cotton and sorghum foliage was excised, and placed in separate plastic containers, and infested with second instar larvae of southern armyworm. After about 5 days, the larvae were examined for percent mortality.

Mexican bean beetle: Potted beam plants were placed on a revolving turntable and sprayed with 100 ml of the 100 ppm test compound formulation, sufficient to wet the plants to runoff, by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each cup which was closed and held for five days. Larvae which were unable to move the length of the body, even upon stimulation by prodding, were considered dead.

House fly: Four to six day old adult house flies were reared according to the specifications of the Chemical Specialties Manufacturing Association (Blue Book, McNair-Dorland Co., N.Y. 1954; pages 243–244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 100 ppm test compound formulation were added to a soufflé cup containing an absorbent cotton pad. As an untreated control, 10 ml of a water-acetone-DMF-emulsifier-sucrose solution, containing no test compound, were applied in a similar manner. A treated control with a commercial technical compound, malathion, formulated in the same manner, was tested as a standard. The bait cup was introduced inside the food strainer prior to admitting the anesthetized flies. After 24 hours, flies which showed no sign of movement on stimulation were considered dead.

Southern corn rootworm: Into a jar containing 60 g of sandy loam soil was added 1.5 ml of an aqueous formulation consisting of an aliquot of the 200 ppm test compound formulation, diluted with water as appropriate for the final soil concentration of the test compound, 3.2 ml of water and five pregerminated corn seedlings. The jar was shaken thoroughly to obtain an even distribution of the test formulation. Following this, twenty southern corn rootworm eggs were placed into a cavity, which was made in the soil. Vermiculite (1 ml) and water (1.7 ml) were then added to this cavity. In a similar manner, an untreated control was prepared by application of the same size aliquot of a water-acetone-DMF-emulsifier solution, containing no test compound. Additionally, a treated control with a commercial technical compound (selected typically from terbufos, fonofos, phorate, chlorpyrifos, carbofuran, isazophos, or ethoprop), formulated in the same manner was used as a test standard. After 7 days, the living rootworm larvae were counted using a well known "Beriese" funnel extraction method.

Southern root-knot nematode: Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasteurized soil. Then into a hole made in the center of the soil in the cone was pipetted an aliquot of the 333 ppm test compound formulation. A treated control with a commercial technical compound, fenamifos, formulated in a similar manner, was tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1—severe galling, equal to untreated control
3—light galling
4—very light galling
5—no galling, i.e., complete control These results were then converted to an $ED_3$ or $ED_5$ value (effective dose to provide a 3 or 5 gall rating).

Seed Treatment Evaluations: For laboratory evaluations, an approximate 80% concentrate of the test compound in ethanol was applied to corn seeds (Zea max) contained in a glass vial by thoroughly mixing on a ball mill for about 45 minutes. This process was repeated a second time and provided an approximate 6-7 g ai/kg of seeds. The seeds were planted into soil pots which were infested with eggs of southern corn rootworm which was used as an indicator organism. The pots were watered and the germinated plants were kept in the greenhouse for a period of several weeks during which the eggs hatched into larvae which were counted at various intervals of time.

For the field tests, an approximate 50% (500 g ai/l) suspension concentrate of the test compound was prepared utilizing the following components and preferred ranges:

| Test Compound | Active Ingredient | | Wt. % 25–75 |
|---|---|---|---|
| Rouge basoflex 3855 | red dye | colorant | 0.5–5.0 |
| Soprophor BC 10 | ethoxylated nonylphenol | wetting agent | 2.0–8.0 |
| Soprophor PS 19 | ethoxylated alkyl-aryl and alcohol phosphate esters, K salt. | dispersing agent | 1.0–5.0 |
| Rhodorsil 426R | silicone | antifoam | 0.1–3.0 |
| Rhodopol MD | Xantham gum | viscosity agent | 0.1–0.3 |
| Proxel GXL (19%) | 1,2-benzisothiazolin-3-1-one | preservative | 0.1–0.3 |
| Rhodoviol BM | polyvinyl alcohol | sticker | 1.0–4.0 |
| Alsi AD | inert clay | filler | 10–50 |
| Water | solvent | carrier | 50–75 |

The seed treatment application was made by first grinding the formulation to 3–5 microns particle size and then this was applied to the seeds as a coating using an Aeromatic Fluid Bed Dryer to provide an approximate concentration of 7 g ai/kg of seed. This suspension concentrate was then used to treat various types of seeds, including corn (Zea mix) and lima bean (*Phaseolus lunatus*), which were then planted under field conditions. Subsequent evaluations were then made for the control of various pest species which infest these seeds or germinated plants thereof.

Use Results: Results of miticidal, insecticidal, and nematicidal activity for some of the representative compound EXAMPLES 1–268 of the invention are discussed below or some compound EXAMPLES are set forth in TABLE 3 against the indicated test species (BA, SAW, MBB, HF, TSM, SCRW: designated by common name abbreviations) and at the indicated dosage rates. The results in TABLE 3 are presented (by an X) as compounds which provide a 70–100% mortality against the indicated test species.

The compounds of the invention also provide some other control of mites (TSM) where, for example, compounds of EXAMPLES 9, 18, 19, 30, 70, 71, 92, 187, 188, 189, 190, 192, 199, 201, 202, 216, 222, 223, and 228, all at 100 ppm except compound of EXAMPLE 30 at 25 ppm, gave 50–100% residual toxicity (mortality) to hatched larvae in the mite ovicide test. Compounds of the invention furthermore provide control of various mite species. For example, compound of EXAMPLE 92 was evaluated as a standard 20% (200 g ai/liter) emulsifiable concentrate formulation in field trials and provided the following results:

| Species/Crop | g ai/Ha | % Control |
|---|---|---|
| *Tetranychus uticae* (twospotted spider mite)/ Cotton | 50–100 | 60–90 |
| *Polyphagotarsonemus latus* (broad mite)/ Cotton | ≧100 | 50–75 |
| *Phyllocoptruta oleivora* (citrus rust mite)/ Orange | 50 | 75–100 |

Additionally, the compound of EXAMPLE 189 in another field evaluation, formulated in a manner similar to that described above for standard test procedures at a concentration of 10–20 g ai/liter, provided 60–95% control of *Panonychus ulmi* (European Red Mite) applied as a spray to an individual apple tree.

Some of the compounds additionally exhibit systemic control of insect larvae and aphids via root uptake at the soil concentrations specified in the above protocols. The results are as follows: 30–100% control of southern armyworm and/or Colorado potato beetle on tomato (compounds of EXAMPLES 4, 25, 40, 44, 48, 66, 68, 81, 86, 87, 95, 96, 103, 106, 121, 128, 131, 143, 149, 150, 151, 159, 163, 180, 182, 207, and 219); 30–69% control of southern armyworm on sorghum (compounds of EXAMPLES 44 and 48); and 30–69% control of cotton aphid on cotton (compound of EXAMPLE 60).

Nematicidal activity is additionally provided by compounds of the invention where, for example, compounds of EXAMPLES 25, 86, 130, and 131, gave $ED_3$ values on SRKN of between about 7 to 21 kg/ha.

Furthermore, compounds of the invention exhibit reduced or antifeeding properties for some pest species, for example for foliar pests such as southern armyworm and Mexican bean beetle.

Control of various soil pests infesting the seeds or germinated plants thereof is provided by a seed treatment application (6-7 g ai/kg of seed) compounds of the invention as follows:

Southern corn rootworm larvae (*Diabrotica u. howardi*), as indicator soil pest species in lab tests on corn seeds (Zea max), were 100% controlled 3 weeks after corn seeds were planted by compounds of EXAMPLES 3, 4 and 28, which maintained good residual control for periods of time 2-3 times longer.

Seed corn maggots (*Delia platura*), representative of the Diptera order, were >90% controlled by the compound of EXAMPLE 4 about 10 days after treated lima bean seeds (*Phaseolus lunatus*) were planted under field conditions.

Black cutworms (*Agrotis ipsilon*), representative of the Lepidoptera order, were 100% controlled by the compound of EXAMPLE 4 about 20 days after planting treated corn seeds (Zea max) under field conditions. This decreased to about 50% control after 27 days.

The compounds of the invention have utility against various pest species at even lower rates, for example: for foliar application, rates in the range of about 50-0.5 ppm, or less, may be useful; for bait application, rates in the range of about 50-0.05 ppm, or less, may be useful; and for soil application, rates in the range of about 1.0-0.01 ppm, or less, may be useful.

In the above discussion and the results reported in TABLE 3, compounds according to the invention are applied at various concentrations. The use of a 1 ppm (concentration of the compound in parts per million of the test solution applied) foliar solution or suspension or emulsion corresponds approximately to an application of 1 g/ha of active ingredient, based upon an approximate spray volume of 1000 liters/ha (sufficient to run off). Thus applications of foliar sprays of from about 6.25 to 500 ppm would correspond to about 6-500 g/ha. For soil applications, a 1 ppm soil concentration, on the basis of about a 7.5 cm soil depth, corresponds to an approximate 1000 g/ha broadcast field application.

TABLE 3

USE EXAMPLE OF PESTICIDAL ACTIVITY OF REPRESENTATIVE IMIDAZOLE COMPOUNDS PROVIDING 70-100% PEST MORTALITY

| CMPD. OF EXAMPLE | Foliar or Bait Application at 100 ppm | | | | | Soil conc.- 1.45 ppm |
|---|---|---|---|---|---|---|
| | BA | SAW | MBB | HF | TSM | SCRW |
| 1 | X | | | X | | |
| 2 | | | X | | | X |
| 3 | | X | | X | | X |
| 4 | X | X | | X | | X |
| 5 | | X | | X | | X |
| 6 | | | | X | | X |
| 7 | | | | | | X |
| 8 | | | | X | | X |
| 9 | X | X | X | X | X | X |
| 10 | X | X | | X | | |
| 11 | X | | | X | | |
| 12 | | | | X | | X |
| 13 | | X | | X | | X |
| 14 | | | | X | | X |
| 15 | | | | | | |
| 16 | X | | | | | |
| 17 | | | | | | |
| 18 | | X | | X | X | X |
| 19 | X | X | | X | | X |
| 20 | X | X | | X | | |
| 21 | X | | X | | X | |
| 22 | | X | X | | | |
| 23 | X | X | X | X | | X |
| 24 | | | X | | X | |
| 25 | X | X | | X | | X |
| 26 | | | | X | | X |
| 27 | | X | | X | | X |
| 28 | X | X | X | X | | X |
| 29 | X | X | X | X | | X |
| 30 | X | | | X | X | X |
| 31 | | X | X | X | | X |
| 32 | X | X | X | X | | X |
| 33 | X | X | X | X | | X |
| 34 | | X | X | X | | X |
| 35 | X | X | | X | | X |
| 36 | | X | | X | | X |
| 37 | | X | X | X | | X |
| 38 | | X | X | X | | X |
| 39 | | X | X | X | | X |
| 40 | | X | | X | X | X |
| 41 | X | X | | X | | X |
| 42 | X | X | | X | | X |
| 44 | X | X | | X | | |
| 45 | X | X | X | X | | X |
| 47 | | X | X | X | | |
| 48 | X | X | | X | | |
| 59 | X | X | | X | X | |
| 60 | X | X | X | X | X | |
| 61 | X | X | X | X | | |
| 65 | X | X | | X | | |
| 66 | X | X | X | X | | |
| 67 | X | X | | X | | |
| 68 | X | X | X | X | | |
| 69 | X | X | X | X | | |
| 70 | | X | X | X | X | X |
| 71 | | X | | X | | X |
| 72 | X | | X | X | | X |
| 73 | | X | | X | | X |
| 78 | X | X | X | X | | |
| 81 | X | X | X | X | | |
| 82 | | | X | X | | |
| 86 | | | X | | | |
| 87 | X | X | | | | |
| 88 | | | | X | | X |
| 90 | X | X | | X | | X |
| 91 | | | | X | | X |
| 92 | | | X | X | | X |
| 95 | | | X | X | | X |
| 96 | | | | X | | X |
| 101 | X | | | X | | X |
| 102 | | | | X | | X |
| 104 | | X | | X | - | X |
| 106 | | | | X | | X |
| 109 | | X | | X | | X |
| 111 | | | | X | | X |
| 121 | X | X | X | X | | |
| 130 | X | | | X | | |
| 131 | X | X | | X | | |
| 135 | X | X | | X | | |
| 143 | X | X | X | X | | |
| 145 | X | X | | X | | |
| 146 | X | X | X | X | | |
| 147 | | X | | X | | |
| 171 | | | | X | | |
| 172 | | X | | | | |
| 173 | X | | | X | | |
| 174 | X | | | X | | |
| 175 | X | X | | X | | |
| 176 | X | | X | X | | |
| 177 | X | | X | X | | |
| 178 | X | X | | X | | X |
| 179 | X | | | X | | |
| 180 | X | | | X | | |
| 182 | | | | X | | |
| 183 | | X | | X | | |

TABLE 3-continued
USE EXAMPLE OF PESTICIDAL ACTIVITY OF REPRESENTATIVE IMIDAZOLE COMPOUNDS PROVIDING 70-100% PEST MORTALITY

| CMPD. OF EXAMPLE | Foliar or Bait Application at 100 ppm | | | | | Soil conc.- 1.45 ppm |
|---|---|---|---|---|---|---|
| | BA | SAW | MBB | HF | TSM | SCRW |
| 184 | | | | X | X | |
| 185 | | | | X | | |
| 186 | | | | X | | |
| 187 | | | X | | X | |
| 188 | | | X | | X | |
| 189 | | | | | X | |
| 190 | | | X | | X | |
| 191 | | | X | | X | |
| 192 | | | | | X | |
| 194 | | | | | X | |
| 196 | X | | | X | X | |
| 198 | | | | X | | |
| 199 | | | | | X | |
| 200 | | | | | X | |
| 201 | | | | | X | |
| 202 | | | | | X | |
| 203 | | | | | X | |
| 204 | | | | | X | |
| 205 | | | | | X | |
| 206 | | | | | X | |
| 211 | | | | | X | |
| 212 | | | | | X | |
| 213 | | X | | | X | |
| 214 | | X | | | X | |
| 215 | | | | X | | |
| 216 | | | X | | X | |
| 217 | | | | X | | |
| 218 | | | X | X | X | |
| 219 | | | | X | | |
| 220 | | | X | | X | |
| 221 | | | X | | X | |
| 222 | | X | X | | X | |
| 223 | | | X | | X | |
| 224 | | | X | | X | |
| 225 | | | | | X | |
| 226 | | | | | X | |
| 230 | | | X | | X | |
| 231 | | | X | | X | |
| 233 | | | X | | X | |
| 235 | | | | | X | |
| 236 | | | | | X | |
| 240 | | | | | X | |
| 243 | | | | | X | |
| 244 | | | | | X | |
| 245 | | | X | | | |
| 247 | | | | | X | |
| 248 | | | | | X | |
| 250 | | | | | X | |
| 251 | | | X | | X | |
| 253 | X | X | X | X | | |
| 254 | X | X | X | X | | |
| 255 | X | X | X | X | | |
| 256 | X | | | X | | |
| 257 | X | | | X | | |
| 265 | | | X | | | |

METHODS AND COMPOSITIONS

As is evident from the foregoing pesticidal uses, the present invention provides pesticidally active compounds and methods of use of said compounds for the control of a number of pest species which includes: arthropods, especially insects or mites; plant nematodes; or helminth or protozan pests. The compounds thus are advantageously employed in practical uses, for example, in agricultural or horticultural crops, forestry, veterinary medicine or livestock husbandry, or in public health.

A feature of the present invention therefore provides a method of control of pests at a locus which comprises the treatment of the locus (e.g., by application or administration) with an effective amount of a compound of general formula (I) and more preferably a compound of formula (II), wherein the substituent groups are as hereinbefore defined. The locus includes, for example, the pest itself or the place (plant, animal, person, field, structure, premises, forest, orchard, waterway, soil, plant or animal product, or the like) where the pest resides or feeds.

The compounds of this invention are preferably used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

Furthermore, these compounds may be useful in the control via foliar application or systemic action of some arthropods, especially some insects or mites, which feed on the above ground portions of plants. Control of foliar pests may additionally be provided by application to the plant roots or plant seeds with subsequent systemic translocation to the above ground portions of the plants.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household good, e.g. carpets and textiles, compounds of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as *Heliothis virescens* (tobacco budworm), *Heliothis armigera* and *Heliothis zea, Spodoptera* spp. such as *S. exempta, S. frugiperda, S. exiqua, S. littoralis* (Egyptian cotton worm), *S. eridania* (southern army worm), and *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Artogeia spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moth), *Plutella xylostella* (diamond back moth), *Bupalus piniarius, Cheimatobia brumata, Lithocolletis blancardella, Hyponomeuta padella, Plutella maculipennis, Malacosoma neustria, Euproctis chrysorrhoea, Lymantria* spp. *Bucculatrix thurberiella, Phyllocnistis citrella, Euxoa* spp., *Feltia brassicae, Panolis flammea, Prodenia litura, Carpocapsa pomonella, Pyrausta nubilalis, Ephestia kuehniella, Galleria mellonella, Tineola bisselliella, Tinea pellionella, Hofmannophila pseudospretella, Cacoecia podana, Capus reticulana, Choristoneura fumiferana, Clysia ambiguellis, Homona magnanime* and *Tortix viridana.*

Against adults and larvae of Coleoptera (beetles) e.g. *Hypothenemus hampei* (coffee berry borer), Hylesinus spp. (bark beetles), Anthonomus spp. e.g. grandis (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp., Limonius spp. (wireworms), Dermolepida spp., Popillia spp., Heteronychus spp. (white grubs), *Phaedon cochleariae* (mustard beetle), Epitrix spp. (flea beetles), *Lissorhoptrus oryzophilus* (rice water weevil), Meligethes spp. (pollen beetles), Ceutorhynchus spp., Rhynchophorus and Cosmopolites spp. (root weevils), *Anobium punctatum, Rhizopertha dominica, Bruchidius obtectus, Acanthoscelides obtectus, Hylotrupes bajulus, Agelastica alni, Psylliodes chrysocephala, Epilachna varivestis,* Atomaria spp., *Oryzaephilus surinamensis,* Sitophilus spp., *Otiorrhynchus sulcatus, Cosmoplites sordidus, Ceuthorrhynchus assimilis, Hypera postica, Dermestes* spp., Trogoderma spp., Anthrenus spp., Attagenus spp., *Lyctus* spp., *Maligethes aeneus,* Ptinus spp., *Niptus hololeucrus, Gibbium psylloides,* Tribolium spp., *Tenebrio molitor,* Conoderus spp., *Melolontha melolontha, Amphimallon solstitialis* and *Costelytra zealandica.*

Against Heteroptera (Hemiptera and Homoptera) e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp., Eurygaster spp., *Piesma quadrata, Cimex lectularius, Rhodnius prolixus* and Triatoma spp. *Aspidiotus hederae, Aeurodes brassicae, Brevicoryne brassicae, Cryptomyzus ribis, Doralis fabae, Doralis pomi., Eriosoma lanigerum, Hyalopterus arundinis, Macrosiphum avenae, Phorodon humuli, Rhopalosiphum padi, Euscelis bilobatus, Nephotettix cincticeps, Lecanium corni, Saissetia oleae, Laodelphax striatellus.*

Against Hymenoptera e.g. Athalia spp. and Cephus spp. (saw flies), Atta spp. (leaf cutting ants), Diprion spp., Hopolocampa spp., Lasius spp., Monomorium spp., Polistes spp., Vespa spp., Vespula spp., and Solenopsis spp.

Against Diptera e.g. Delia spp. (root maggots), Atherigona spp. and Chlorops spp., Sarcophaga spp., Musca spp, Phormia spp., Aedes spp., Anopheles spp., Simulium spp., (shoot flies), Phytomyza spp. (leaf miners), Ceratitis spp. (fruit flies), Culex spp., *Drosophila melanogaster, Ceratitis capitata, Dacus oleae, Tipula paludosa, Calliphora erythrocephala,* Lucilia spp., Chrysomyia spp., *Cuterebra* spp., *Gastrophilus* spp., Hyppobosca spp., Stomoxys spp., Oestrus spp., Hypoderma spp., Tabanus spp., Fannia spp., *Bibio hortulanus, Oscinella frit,* Phorbia spp., *Pegomyia hyoscyani.*

Against Thysanoptera such as *Thrips tabaci, Hercinothrips femoralis,* and Frankliniella spp.

Against Orthoptera such as Locusta and Schistocerca spp., (locusts and crickets) e.g. Gryllus spp., and Acheta spp. for example, *Blatta orientalis, Periplaneta americana, Leucophaea maderae, Blatella germanica, Acheta domesticus, Gryllotalpa* spp., *Locusta migratoria migratorioides, Melanoplus differentialis* and *Schistocerca gregaria.*

Against Collembola e.g. Sminthurus spp. and Onychiurus spp. (springtails); Periplaneta spp. and Blattela spp. (roaches).

Against Isoptera e.g. Odontotermes spp., Reticulotermes spp., Coptotermes spp. (termites).

Against Dermaptera e.g. Forticula sp. (earwigs).

Against arthropods of agricultural significance such as Acari (mites) e.g. Tetranychus spp., Panonychus spp., Bryobia spp. (spider mites), Ornithonyssus spp. (fowl mites), Eriophyes spp. (gall mites), and Polyphadotarsonemus supp.

Against Thysanura, for example *Lepisma saccharia.*

Against Anoplura for example, *Phylloxera vastatrix,* Pemphigus spp., *Pediculus humanus corporis,* Haematopinus spp. and Linognathus spp.

Against Mallophaga, for example, Trichodectes spp. and Damalinea spp.

Against Siphonoptera, for example, *Xenopsylla cheopis* and Ceratophyllus spp.

Against other arthropods, such as Blaniulus spp. (millipedes), Scutigerella spp. (symphilids), Oniscus spp. (woodlice) and Triops spp. (crustacea).

Against Isopoda, for example, *Oniseus asellus, Armadillidium vulgare* and *Porcellio scaber.*

Against Chilopoda, for example, *Geophilus carpophagus* and *Scutigera spex.*

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*; lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (*R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworm such as Ditylenchus spp. (e.g. *D. dipsaci*).

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boophilus spp. e.g. *Boophilus microplus, Amblyomma* spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata*) and mites (e.g. Damalinia spp., *Dermahyssus gallinae*, Sarcoptes spp. e.g. *Sarcoptes scabiei*, Psoroptes spp., Chlorioptes spp;, Demodex spp., Eutrombicula spp.,); Diptera (e.g. Aedes spp., Anopheles spp., Musca spp., Hypoderma spp., Gasterophilus spp., Simulium spp); Hemiptera (e.g. Triatoma spp); Phthirapter (e.g. Damalinia spp., Linognathus spp.); Siphonaptera (e.g. Ctenocephalides spp.); Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei*, Cooperia spp. and *Hymenolepis nana*; in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoms cruzi*, Leishaminia spp., Plasmodium spp., Babesis spp., Trichomonadidae spp., Histomanas spp., Giardia spp., Toxoplasma spp., Entamoeba histolytica and Theileria spp..

The invention, as previously described, provides methods of control of pests via application or administration of an effective amount of compounds of formula (I) or (II) at a locus which comprises treatment of the locus.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 0.01 kg/ha to to about 2 kg/ha.

When a pest is soil-borne, the active compound generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects or mites, or nematodes attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, or lucerne), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocysts by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

The compositions hereinafter described for application to growing crops or crop growing loci or as a seed dressing may, in general, alternatively be employed for topical application to man or animals or in the protection of stored products, household goods, property or areas of the general environment. Suitable means of applying the compounds of the invention include:

- to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;
- to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;
- to the environment in general or to specific locations where pests may lurk, including stored products, timber, household goods, or domestic or industrial premises, as sprays, fogs, dusts, smokes, waxsmears, lacquers, granules or baits, or in tricklefeeds to waterways, wells, reservoirs or other running or standing water;
- to domestic animals in feed to control fly larvae feeding in their feces;

In practice, the compounds of the invention most frequently form parts of compositions. These compositions can be employed to control: arthopods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of the invention, such as described earlier, as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

Compositions suitable for administration to vertebrates or man, include preparations suitable for oral, parenteral, percutaneous, e.g. pouron, or topical administration.

Compositions for oral administration comprise one or more of the compounds of general formula(I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate the active ingredient contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle or solid or semisolid subcutaneous implants or pellets designed to release the active ingredient over a protracted period of time and may be prepared and made sterile in any appropriate manner known to the art.

Compositions for percutaneous and topical administration include sprays, dusts, baths, dips, showers, jets, greases, shampoos, creams, waxsmears, or pour-on preparations or devices (e.g. ear tags attached externally to animals in such a way as to provide local or systemic arthropod control).

Solid or liquid baits, suitable for controlling arthropods, comprise one or more compounds of general formula(I) and a carrier or diluent which may include a food substance or some other substance to induce consumption by the arthropod.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; watersoluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain different other additives such adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of general formula(I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavouring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, malathion, monocrotophos, parathion, phosalone, pirimiphos-methyl, triazophos, cyfluthrin, cyermethrin, deltamethrin, fenpropathrin, fenvalerate, permethrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula(I) are therefore generally in the form of compositions, which are in various solid or liquid forms.

Solid forms of compositions which can be used are dusting powders (with a content of the compound of formula(I) ranging up to 80%), wettable powders or granules (including water dispersible granules), particularly those obtained by extrusion, compacting, impregnation of a granular carrier, or granulation starting from a powder (the content of the compound of formula(I) in these wettable powders or granules being between about 0.5 and about 80%). Solid homogenous or heterogenous compositions containing one or more compounds of general formula(I) for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is (are) thoroughly mixed in a suitable blender with additional substances which may be impregnated on the porous filler and is (are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The application dose (effective dose) of active ingredient, also as a formulated composition, is generally between about 0.005 and about 15 kg/ha, preferably between about 0.01 and about 2 kg/ha. Therefore, the rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of general formula(I) or of total active ingredients (that is to say the compound(s) of general formula(I) together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of general formula(I). For administration to animals orally or parenterally, including percutaneously solid or liquid compositions, these normally contain from about 0.1% to about 90% by weight of one or more compounds of general formula(I). Medicated feedstuffs normally contain from about 0.001% to about 3% by weight of one or more compounds of general formula(I). Concentrates or supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula(I).

Dusts or liquid compositions for application to livestock, persons, goods, premises or outdoor areas may contain from about 0.0001% to about 15%, more especially from about 0.005% to about 2.0%, by weight, of one or more compounds of general formula(I). Suitable concentrations in treated waters are between about 0.0001 ppm and about 20 ppm, more particularly about 0.001 ppm to about 5.0 ppm. of one or more compounds of general formula(I) and may be used therapeutically in fish farming with appropriate exposure times. Edible baits may contain from about 0.01% to about 5%, preferably from about 0.01% to about 1.0%, by weight, of one or more compounds of general formula(I).

When administered to vertebrates parenterally, orally or by percutaneous or other means, the dosage of compounds of general formula(I) will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 270A-270L illustrate compositions for use against arthropods, especially mites or insects, plant nematodes, or helminth or protozoan pests which comprise, as active ingredient, compounds of general formula (I), especially compounds according to formula (II), such as those described in preparative EXAMPLES 1 to 268. The compositions described in EXAMPLES 270A-270F can each be diluted in water to give a sprayable composition at concentrations suitable for use in the field. Generic chemical descriptions of the ingredients (for which all of the following percentages are in weight percent), used in the composition EXAMPLES 270A-270L exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No 2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 270A

A water soluble concentrate is prepared with the composition as follows:

| Active ingredient | 7% |
|---|---|
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 270B

An emulsifiable concentrate (EC) is prepared with the composition as follows:

| Active ingredient | 7% |
|---|---|
| Soprophor BSU | 4% |
| Arylan CA | 4% |
| N-methylpyrrolidone | 50% |
| Solvesso 150 | 35% |

The first three components are dissolved in N-methylpyrrolidone and to this is then added the Solvesso 150 to give the final volume.

EXAMPLE 270C

A wettable powder (WP) is prepared with the composition as follows:

| Active ingredient | 40% |
|---|---|
| Arylan S | 2% |
| Darvan No 2 | 5% |
| Celite PF | 53% |

The ingredients are mixed and ground in a hammermill to a powder with a particle size of less than 50 microns.

EXAMPLE 270D

An aqueous-flowable formulation is prepared with the composition as follows:

| Active ingredient | 40.00% |
|---|---|
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

EXAMPLE 270E

An emulsifiable suspension concentrate is prepared with the composition as follows:

| Active ingredient | 30.0% |
|---|---|
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 270F

A water dispersible granule is prepared with the composition as follows:

| Active ingredient | 30% |
|---|---|
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 270G

A dusting powder is prepared with the composition as follows:

| Active ingredient | 1 to 10% |
|---|---|

-continued

| | |
|---|---|
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 270H

An edible bait is prepared with the composition as follows:

| | |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 270I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 270J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infestion by arthropods, helminths or protozoa, by spraying or dipping, or by oral administration in drinking water, to control the arthropods, helminths or protozoa.

EXAMPLE 270K

A slow release bolus composition is formed from granules containing the following components in varying percentages(similar to those described for the previous compositions) depending upon need:
Active ingredient
Density agent
Slow-release agent
Binder The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 270L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | catalytic amount |

The components are blended and then formed into suitable shapes by melt-extrusion or molding. These composition are useful, for example, for addition to standing water or for fabrication into collars or eartags for attachment to domestic animals to control pests by slow release.

While the present invention has been set forth in specific and illustrative details and described with preferred particularity, it is susceptible to changes, modifications or alternations, obvious to one of ordinary skill in the art, without departing from the scope and spirit of the invention, which is defined by the claims appended hereto.

What we claim is:

1. A compound of formula (I)

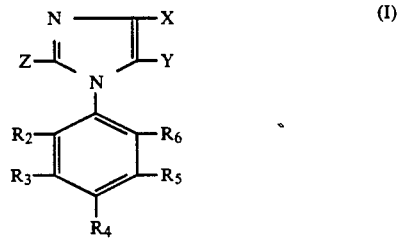

wherein:
X is haloalkyl, haloalkoxy or unsubstituted or halo-substituted alkylsulfenyl, alkylsulfinyl or alkylsulfonyl, wherein the alkyl or alkoxy moiety is a linear or branched chain, containing one to four carbon atoms, and the halo-substitution consists of one or more halogen atoms, which are the same or different, up to full substitution of the alkyl or alkoxy moiety;

Y and Z are each individually: hydrogen, halogen, nitro, cyano, hydroxyl or an acceptable salt thereof, sulfhydryl or an acceptable salt thereof, formyl, hydroxycarbonyl or an acceptable salt thereof, alkoxycarbonyl, aminocarbonyl, alkylaminocarbonyl, dialkylaminocarbonyl, amino, alkylamino, dialkylamino, a trialkylammonium salt, cyanoalkyl, alkoxycarbonylamino, alkylaminocarbonylamino, dialkylaminocarbonylamino, aminosulfonyl, alkylaminosulfonyl, dialkylaminosulfonyl or alkoxyalkylideneimino, in which the alkyl or alkoxy moiety is a linear or branched chain containing one to four carbon atoms; a linear or branched chain alkenyl or alkynyl group containing two to four carbon atoms; an unsubstituted or halo-substituted alkyl, alkoxy, alkylcarbonyl, alkylcarbonylamino, alkylsulfenyl, alkylsulfinyl or alkylsulfonyl, in which the alkyl or alkoxy moiety is a linear or branched chain containing one to four carbon atoms and the halo-substitution consists of one or more halogen atoms, which are the same or different, up to full substitution of the alkyl or alkoxy moiety; and only one of Y and Z is a sulfur containing group; and $R_2$, $R_3$, $R_4$, $R_5$ and $R_6$ are individually: hydrogen, halogen, nitro, cyano, amino, alkylamino or dialkylamino, in which the alkyl moiety is a linear or branched chain containing one to four carbon atoms; a linear or branched chain alkenyl or alkynyl group containing two to four carbon atoms, which is substituted by one or more halogen atoms, which are the same or different, up to full substitution; or unsubstituted or halo-substituted alkyl, alkoxy, alkylsulfenyl, alkylsulfinyl or alkylsulfonyl, in which the alkyl or alkoxy moiety is a linear or branched chain containing one to four carbon atoms and the halo-substitution consists of one or more halogen atoms, which are the same or different, up to full substitution of the alkyl or alkoxy moiety; and provided:
that when X is haloalkyl and
Y, Z, $R_2$, $R_3$, $R_5$ and $R_6$ are hydrogen or Y, Z, $R_2$, $R_5$ and $R_6$ are hydrogen and $R_3$ is alkyl,
then $R_4$ is other than nitro, amino, alkyl or alkoxy.

2. The compound of claim 1 of formula (I), wherein X is $S(O)_nR_1$, having a formula (IIa)

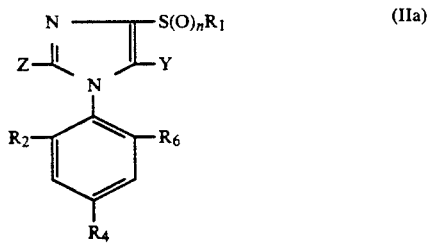

wherein:
Y and Z are each individually: hydrogen, halogen, nitro, cyano, hydroxyl, sulfhydryl, amino, alkylamino or dialkylamino; or unsubstituted or fully halo-substituted alkyl, alkoxy, alkylcarbonyl, alkylcarbonylamino, alkylsulfenyl, alkylsulfinyl or alkylsulfonyl; and only one of Y and Z is a sulfur containing group;

$R_1$ is a linear or branched alkyl group of one to four carbon atoms which are unsubstituted or halo-substituted by one or more halogen atoms, which are the same or different;

$R_2$ is hydrogen, halogen, alkyl, alkoxy, methylsulfenyl, methylsulfinyl or methylsulfonyl;

$R_4$ is halogen, trifluoromethyl, trifluoromethoxy, difluoromethoxy, trifluoromethylsulfenyl, trifluoromethylsulfinyl, trifluoromethylsulfonyl or alkyl;

$R_6$ is halogen; and n is 0, 1 or 2.

3. The compound of claim 2 of formula (IIa), having a formula (IIa-1), wherein:
Y is hydrogen, halogen, amino, hydroxy, alkoxy, methylsulfenyl, methylsulfinyl or methylsulfonyl;
Z is hydrogen, halogen, or unsubstituted or fully halo-substituted alkyl;
$R_1$ is methyl fully substituted by halogen atoms which are the same or different;
$R_2$ is hydrogen, halogen or methylsulfenyl;
$R_4$ is halogen, trifluoromethyl or trifluoromethoxy; and
$R_6$ is fluorine, chlorine or bromine.

4. The compound of claim 3 of formula (IIa-1), having a formula (IIa-2) wherein:
Y is hydrogen, chlorine, bromine, methylsulfenyl, methylsulfinyl or methoxy;
Z is hydrogen, chlorine, bromine or methyl;
$R_1$ is trifluoromethyl, dichlorofluoromethyl or chlorodifluoromethyl;
$R_2$ is hydrogen, chlorine, bromine or methylsulfenyl;
$R_4$ is chlorine, bromine, fluorine, trifluoromethyl or trifluoromethoxy; and
$R_6$ is chlorine or bromine.

5. The compound of claim 4, having the formula (IIa-2), which is:
1-(2,6-dichloro-4-trifluoromethylphenyl)-2-chloro-5-methylsulfenyl-4-chlorodifluoromethylsulfenylimidazole;
1-(2,6-dichloro-4-trifluoromethylphenyl)-2-chloro-4-trifluoromethylsulfinylimidazole;
1-(2,6-dichloro-4-trifluoromethylphenyl)-5-bromo-4-dichlorofluoromethylsulfenylimidazole;
1-(2,6-dichloro-4-trifluoromethylphenyl)-2-chloro-4-dichlorofluoromethylsulfenylimidazole;
1-(2,6-dichloro-4-trifluoromethylphenyl)-2-bromo-4-dichlorofluoromethylsulfenylimidazole;
1-(2,6-dichloro-4-trifluoromethylphenyl)-4-trifluoromethylsulfinylimidazole;
1-(2,6-dichloro-4-trifluoromethylphenyl)-2-chloro-4-dichlorofluoromethylsulfinylimidazole;
1-(2,6-dichloro-4-trifluoromethylphenyl)-2-chloro-4-dichlorofluoromethylsulfonylimidazole;
1-(2,6-dichloro-4-trifluoromethylphenyl)-2-bromo-4-chlorodifluoromethylsulfinylimidazole;
1-(2,6-dichloro-4-trifluoromethylphenyl)-2-bromo-4-chlorodifluoromethylsulfenylimidazole;
1-(2,6-dichloro-4-trifluoromethylphenyl)-2-chloro-4-chlorodifluoromethylsulfenylimidazole;
1-(6-chloro-2-methylsulfenyl-4-trifluoromethylphenyl)-2-bromo-4-chlorodifluoromethylsulfonylimidazole;
1-(6-chloro-2-methylsulfenyl-4-trifluoromethylphenyl)-2-chloro-4-dichlorofluoromethylsulfonylimidazole;
1-(2,6-dichloro-4-trifluoromethylphenyl)-4-dichlorofluoromethylsulfenylimidazole;
1-(2,6-dichloro-4-trifluoromethylphenyl)-4-dichlorofluoromethylsulfinylimidazole;

1-(2,6-dichloro-4-trifluoromethylphenyl)-4-dichlorofluoromethylsulfonylimidazole;
1-(2,6-dichloro-4-trifluoromethylphenyl)-2-methyl-4-dichlorofluoromethylsulfenylimidazole;
1-(2,6-dichloro-4-trifluoromethylphenyl)-2-methyl-4-dichlorofluoromethylsulfinylimidazole;
1-(2,6-dichloro-4-trifluoromethylphenyl)-2-methyl-4-dichlorofluoromethylsulfonylimidazole;
1-(2,4,6-trichlorophenyl)-4-dichlorofluoromethylsulfenylimidazole;
1-(2,4,6-trichlorophenyl)-4-dichlorofluoromethylsulfinylimidazole;
1-(2,6-dichloro-4-trifluoromethoxyphenyl)-4-dichlorofluoromethylsulfinylimidazole;
1-(2,6-dichloro-4-trifluoromethylphenyl)-4-chlorodifluoromethylsulfinylimidazole;
1-(2,6-dichloro-4-trifluoromethylphenyl)-2-methyl-4-chlorodifluoromethylsulfinylimidazole;
1-(2,6-dichloro-4-trifluoromethylphenyl)-2-methyl-4-chlorodifluoromethylsulfonylimidazole;
1-(2,4,6-trichlorophenyl)-4-chlorodifluoromethylsulfenylimidazole; or
1-(2,4,6-trichlorophenyl)-4-chlorodifluoromethylsulfinylimidzole.

6. The compound of claim 4, having the formula (IIa-2), which is:
1-(2,6-dichloro-4-trifluoromethylphenyl)-2-chloro-4-trifluoromethylsulfonylimidazole;
1-(2,6-dichloro-4-trifluoromethylphenyl)-5-methylsulfenyl-4-dichlorofluoromethylsulfenylimidazole;
1-(2,6-dichloro-4-trifluoromethylphenyl)-4-trifluoromethylsulfonylimidazole;
1-(2,6-dichloro-4-trifluoromethylphenyl)-5-bromo-4-trifluoromethylsulfonylimidazole;
1-(2,6-dichloro-4-trifluoromethylphenyl)-2-bromo-4-dichlorofluoromethylsulfinylimidazole;
1-(2,6-dichloro-4-trifluoromethylphenyl)-5-bromo-4-dichlorofluoromethylsulfonylimidazole;
1-(2,6-dichloro-4-trifluoromethylphenyl)-2-bromo-4-dichlorofluoromethylsulfonylimidazole;
1-(2,6-dichloro-4-trifluoromethylphenyl)-2-bromo-4-chlorodifluoromethylsulfonylimidazole;
1-(2,6-dichloro-4-trifluoromethylphenyl)-2-chloro-4-chlorodifluoromethylsulfinylimidazole;
1-(2,6-dichloro-4-trifluoromethylphenyl)-2-chloro-4-chlorodifluoromethylsulfonylimidazole;
1-(2,6-dichloro-4-trifluoromethylphenyl)-5-methylsulfonyl-4-dichlorofluoromethylsulfinylimidazole;
1-(2,6-dichloro-4-trifluoromethylphenyl)-5-methylsulfinyl-4-dichlorofluoromethylsulfinylimidazole;
1-(6-chloro-2-methylsulfenyl-4-trifluoromethylphenyl)-2-chloro-4-dichlorofluoromethylsulfenylimidazole;
1-(6-chloro-2-methylsulfenyl-4-trifluoromethylphenyl)-2-chloro-4-dichlorofluoromethylsulfinylimidazole;
1-(2,6-dichloro-4-trifluoromethylphenyl)-2-chloro-5-methylsulfenyl-4-trifluoromethylsulfenylimidazole;
1-(2,6-dichloro-4-trifluoromethylphenyl)-5-bromo-4-trifluoromethylsulfenylimidazole;
1-(2,6-dichloro-4-trifluoromethylphenyl)-2-methyl-4-chlorodifluoromethylsulfenylimidazole;
1-(2,6-dichloro-4-trifluoromethylphenyl)-5-chloro-4-trifluoromethylsulfenylimidazole;
1-(2,6-dichloro-4-trifluoromethylphenyl)-2,5-dichloro-4-dichlorofluoromethylsulfenylimidazole;
1-(2,6-dichloro-4-trifluoromethylphenyl)-4-chlorodifluoromethylsulfenylimidazole;
1-(2-chloro-4-trifluoromethylphenyl)-4-dichlorofluoromethylsulfenylimidazole;
1-(2-chloro-4-trifluoromethylphenyl)-4-trifluoromethylsulfinylimidazole;
1-(2-chloro-4-trifluoromethylphenyl)-4-trifluoromethylsulfonylimidazole;
1-(2,6-dichloro-4-bromophenyl)-4-dichlorofluoromethylsulfenylimidazole;
1-(2,6-dichloro-4-bromophenyl)-4-dichlorofluoromethylsulfinylimidazole;
1-(2,6-dichloro-4-bromophenyl)-4-chlorodifluoromethylsulfenylimidazole;
1-(2,6-dichloro-4-trifluoromethoxyphenyl)-4-trifluoromethylsulfinylimidazole;
1-(2,6-dichloro-4-trifluoromethoxyphenyl)-4-chlorodifluoromethylsulfenylimidazole;
1-(2,6-dichloro-4-trifluoromethoxyphenyl)-4-chlorodifluoromethylsulfinylimidazole;
1-(2,6-dichloro-4-trifluoromethoxyphenyl)-4-dichlorofluoromethylsulfonylimidazole; or
1-(2,6-dichloro-4-trifluoromethoxyphenyl)-2-bromo-4-dichlorofluoromethylsulfenylimidazole.

7. The compound of claim 2, having the formula (IIa), which is:
1-(2-bromo-6-chloro-4-trifluoromethoxyphenyl)-4-dichlorofluoromethylsulfinylimidazole;
1-(2,6-dichloro-4-trifluoromethoxyphenyl)-2-methyl-4-dichlorofluoromethylsulfenylimidazole;
1-(2,6-dichloro-4-trifluoromethoxyphenyl)-2-methyl-4-dichlorofluoromethylsulfonylimidazole;
1-(2,6-dichloro-4-trifluoromethoxyphenyl)-2-methyl-4-dichlorofluoromethylsulfinylimidazole;
1-(2,6-dichloro-4-trifluoromethylphenyl)-2-cyano-4-dichlorofluoromethylsulfenylimidazole;
1-(2,6-dichloro-4-trifluoromethylphenyl)-5-bromo-2-methyl-4-dichlorofluoromethylsulfenylimidazole;
1-(2,6-dichloro-4-trifluoromethylphenyl)-5-bromo-2-methyl-4-dichlorofluoromethylsulfinylimidazole;
1-(2,4,6-trichlorophenyl)-2-methyl-4-dichlorofluoromethylsulfenylimidazole;
1-(2,4,6-trichlorophenyl)-2-methyl-4-dichlorofluoromethylsulfinylimidazole;
1-(2,4,6-trichlorophenyl)-5-chloro-4-dichlorofluoromethylsulfenylimidazole;
1-(2,4,6-trichlorophenyl)-5-bromo-4-dichlorofluoromethylsulfenylimidazole;
1-(2,4,6-trichlorophenyl)-5-bromo-4-dichlorofluoromethylsulfinylimidazole;
1-(2,4,6-trichlorophenyl)-5-bromo-4-chlorodifluoromethylsulfenylimidazole;
1-(2,4,6-trichlorophenyl)-5-bromo-4-chlorodifluoromethylsulfinylimidazole;
1-(2,4,6-trichlorophenyl)-5-chloro-4-chlorodifluoromethylsulfenylimidazole;
1-(2,4,6-trichlorophenyl)-5-chloro-4-chlorodifluoromethylsulfinylimidazole;
1-(2,4,6-trichlorophenyl)-5-chloro-4-dichlorofluoromethylsulfinylimidazole;
1-(2-bromo-4,6-dichlorophenyl)-4-dichlorofluoromethylsulfenylimidazole;
1-(2-bromo-4,6-dichlorophenyl)-5-bromo-4-dichlorofluoromethylsulfenylimidazole;
1-(2-bromo-4,6-dichlorophenyl)-5-bromo-4-trifluoromethylsulfenylimidazole;
1-(2-bromo-4,6-dichlorophenyl)-4-dichlorofluoromethylsulfinylimidazole;
1-(2,4,6-trichlorophenyl)-5-bromo-4-dichlorofluoromethylsulfonylimidazole;
1-(2-bromo-4,6-dichlorophenyl)-5-bromo-4-dichlorofluoromethylsulfinylimidazole;

1-(2-bromo-4,6-dichlorophenyl)-5-bromo-4-trifluoromethylsulfinylimidazole;
1-(2-bromo-4,6-dichlorophenyl)-5-bromo-4-dichlorofluoromethylsulfonylimidazole;
1-(2-bromo-4,6-dichlorophenyl)-5-bromo-4-trifluoromethylsulfonylimidazole;
1-(2,4,6-trichlorophenyl)-5-chloro-4-chlorofluoromethylsulfenylimidazole; or
1-(2,4,6-trichlorophenyl)-5-bromo-2-methyl-4-dichlorofluoromethylsulfinylimidazole.

8. The compound of claim 1 of formula (I), wherein X is S(O)$_n$R$_1$, having a formula (IIb)

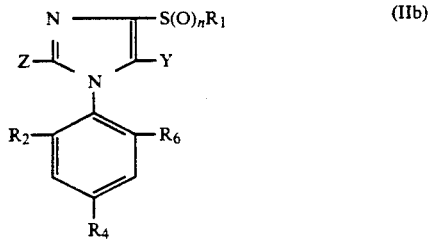

wherein:
- Y is hydrogen, halogen, alkyl, alkoxy, alkoxyalkylideneimino, alkylsulfenyl, alkylsulfinyl or alkylsulfonyl, in which the alkyl and alkoxy moieties of each group are a linear or branched chain containing one to four carbon atoms;
- Z is hydrogen or alkyl which is a linear or branched chain of one to four carbon atoms;
- R$_1$ is a linear or branched chain alkyl group of one to four carbon atoms which are unsubstituted or halosubstituted by one or more halogen atoms, which are the same or different, up to full substitution of the alkyl group;
- R$_2$ is halogen or alkylsulfenyl;
- R$_6$ is halogen;
- R$_4$ is hydrogen, halogen, haloalkyl or haloalkoxy in which the alkyl and alkoxy moieties of each group are a linear or branched chain containing one to four carbon atoms and the halo-substitution is by one or more halogen atoms, which are the same or different up to full substitution of the alkyl or alkoxy moiety; and
- n is 0, 1 or 2.

9. The compound of claim 8 of formula (IIb), having a formula (IIb-1) wherein:
- Y is H, F, Cl, Br, I, CH$_3$, C$_2$H$_5$, OCH$_3$, OC$_2$H$_5$, N=CHOCH$_3$, N=CHOC$_2$H$_5$, SCH$_3$, SOCH$_3$ or SO$_2$CH$_3$;
- Z is H, CH$_3$ or C$_2$H$_5$;
- R$_1$ is CF$_3$, CCl$_2$F, CClF$_2$, CHCl$_2$, CHClF or CHF$_2$;
- R$_2$ is F, Cl, Br, or SCH$_3$;
- R$_6$ is F, Cl or Br;
- R$_4$ is H or F; or R$_4$ is Cl, Br, I, CF$_3$ or OCF$_3$ when Y is CH$_3$, C$_2$H$_5$, OCH$_3$, OC$_2$H$_5$, N=CHOCH$_3$, N=CHOC$_2$H$_5$, SCH$_3$, SOCH$_3$ or SO$_2$CH$_3$; and
- n is 0, 1 or 2.

10. The compound of claim 9, having the formula (IIb-1), which is:

1-(2,6-dichloro-4-fluorophenyl)-5-methylsulfenyl-4-dichlorofluoromethylsulfenylimidazole;
1-(2,4,6-trichlorophenyl)-5-methylsulfenyl-4-dichlorofluoromethylsulfenylimidazole;
1-(2,6-dichloro-4-fluorophenyl)-5-bromo-4-dichlorofluoromethylsulfenylimidazole;
1-(2,6-dichloro-4-fluorophenyl)-5-methylsulfenyl-4-dichlorofluoromethylsulfenylimidazole;
1-(2,6-dichloro-4-fluorophenyl)-5-bromo-4-trifluoromethylsulfenylimidazole;
1-(2,6-dichloro-4-fluorophenyl)-5-chloro-4-dichlorofluoromethylsulfenylimidazole;
1-(2,6-dichloro-4-fluorophenyl)-5-bromo-4-chlorodifluoromethylsulfenylimidazole;
1-(2,4,6-trichlorophenyl)-5-ethoxymethylideneimino-4-dichlorofluoromethylsulfenylimidazole;
1-(2-bromo-4,6-dichlorophenyl)-5-methylsulfenyl-4-dichlorofluoromethylsulfenylimidazole;
1-(2-bromo-4,6-dichlorophenyl)-5-methylsulfenyl-4-trifluoromethylsulfenylimidazole;
1-(2,6-dibromo-4-fluorophenyl)-5-bromo-4-chlorodifluoromethylsulfenylimidazole;
1-(2,6-dichloro-4-fluorophenyl)-5-bromo-4-trifluoromethylsulfonylimidazole;
1-(2,6-dichloro-4-trifluoromethylphenyl)-2-methyl-5-methylsulfenyl-4-dichlorofluoromethylsulfenylimidazole;
1-(2,6-dichloro-4-fluorophenyl)-5-bromo-4-dichlorofluoromethylsulfinylimidazole;
1-(2,6-dichloro-4-fluorophenyl)-5-bromo-4-dichlorofluoromethylsulfonylimidazole;
1-(4-bromo-2,6-dichlorophenyl)-5-methylsulfenyl-4-dichlorofluoromethylsulfenylimidazole; or
1-(2,4,6-trichlorophenyl)-5-methylsulfenyl-4-chlorodifluoromethylsulfenylimidazole.

11. A method for the control of: arthropods; nematodes; or helminth or protozoan pests at a locus which comprises treatment of the locus with an effective amount of a compound of formula (I), wherein the various substituents X, Y, Z, R$_2$, R$_3$, R$_4$, R$_5$ and R$_6$ are as defined in claim 1.

12. A method for the control of: arthropods; nematodes; or helminth or protozoan pests at a locus which comprises treatment of the locus with an effective amount of a compound of formula (IIa), wherein the various substituents X, Y, Z, R$_2$, R$_3$, R$_4$, R$_5$ and R$_6$ are as defined in claim 2.

13. The method of claim 12, wherein the compound of formula (IIa) is:

1-(2,6-dichloro-4-trifluoromethylphenyl)-2-chloro-5-methylsulfenyl-4-chlorodifluoromethylsulfenylimidazole;
1-(2,6-dichloro-4-trifluoromethylphenyl)-2-chloro-4-trifluoromethylsulfinylimidazole;
1-(2,6-dichloro-4-trifluoromethylphenyl)-5-bromo-4-dichlorofluoromethylsulfenylimidazole;
1-(2,6-dichloro-4-trifluoromethylphenyl)-2-chloro-4-dichlorofluoromethylsulfenylimidazole;
1-(2,6-dichloro-4-trifluoromethylphenyl)-2-bromo-4-dichlorofluoromethylsulfenylimidazole;
1-(2,6-dichloro-4-trifluoromethylphenyl)-4-trifluoromethylsulfinylimidazole;
1-(2,6-dichloro-4-trifluoromethylphenyl)-2-chloro-4-dichlorofluoromethylsulfinylimidazole;
1-(2,6-dichloro-4-trifluoromethylphenyl)-2-chloro-4-dichlorofluormethylsulfonylimidazole;
1-(2,6-dichloro-4-trifluoromethylphenyl)-2-bromo-4-chlorodifluoromethylsulfinylimidazole;
1-(2,6-dichloro-4-trifluoromethylphenyl)-2-bromo-4-chlorodifluoromethylsulfenylimidazole;
1-(2,6-dichloro-4-trifluoromethylphenyl)-2-chloro-4-chlorodifluoromethylsulfenylimidazole;
1-(6-chloro-2-methylsulfenyl-4-trifluoromethylphenyl)-2-bromo-4-chlorodifluoromethylsulfonylimidazole;

1-(6-chloro-2-methylsulfenyl-4-trifluoromethylphenyl)-2-chloro-4-dichlorofluoromethylsulfonylimidazole;
1-(2,6-dichloro-4-trifluoromethylphenyl)-4-dichlorofluoromethylsulfenylimidazole;
1-(2,6-dichloro-4-trifluoromethylphenyl)-4-dichlorofluoromethylsulfinylimidazole;
1-(2,6-dichloro-4-trifluoromethylphenyl)-4-dichlorofluoromethylsulfonylimidazole;
1-(2,6-dichloro-4-trifluoromethylphenyl)-2-methyl-4-dichlorofluoromethylsulfenylimidazole;
1-(2,6-dichloro-4-trifluoromethylphenyl)-2-methyl-4-dichlorofluoromethylsulfinylimidazole;
1-(2,6-dichloro-4-trifluoromethylphenyl)-2-methyl-4-dichlorofluoromethylsulfonylimidazole;
1-(2,4,6-trichlorophenyl)-4-dichlorofluoromethylsulfenylimidazole;
1-(2,4,6-trichlorophenyl)-4-dichlorofluoromethylsulfinylimidazole;
1-(2,6-dichloro-4-trifluoromethoxyphenyl)-4-dichlorofluoromethylsulfinylimidazole;
1-(2,6-dichloro-4-trifluoromethylphenyl)-4-chlorodifluoromethylsulfinylimidazole;
1-(2,6-dichloro-4-trifluoromethylphenyl)-2-methyl-4-chlorodifluoromethylsulfinylimidazole;
1-(2,6-dichloro-4-trifluoromethylphenyl)-2-methyl-4-chlorodifluoromethylsulfonylimidazole;
1-(2,4,6-trichlorophenyl)-4-chlorodifluoromethylsulfenylimidazole; or
1-(2,4,6-trichlorophenyl)-4-chlorodifluoromethylsulfinylimidazole.

14. The method of claim 12, wherein the compound of formula (IIa) is:
1-(2,6-dichloro-4-trifluoromethylphenyl)-2-chloro-4-trifluoromethylsulfonylimidazole;
1-(2,6-dichloro-4-trifluoromethylphenyl)-5-methylsulfenyl-4-dichlorofluoromethylsulfenylimidazole;
1-(2,6-dichloro-4-trifluoromethylphenyl)-4-trifluoromethylsulfonylimidazole;
1-(2,6-dichloro-4-trifluoromethylphenyl)-5-bromo-4-trifluoromethylsulfonylimidazole;
1-(2,6-dichloro-4-trifluoromethylphenyl)-2-bromo-4-dichlorofluoromethylsulfinylimidazole;
1-(2,6-dichloro-4-trifluoromethylphenyl)-5-bromo-4-dichlorofluoromethylsulfonylimidazole;
1-(2,6-dichloro-4-trifluoromethylphenyl)-2-bromo-4-dichlorofluoromethylsulfonylimidazole;
1-(2,6-dichloro-4-trifluoromethylphenyl)-2-bromo-4-chlorodifluoromethylsulfonylimidazole;
1-(2,6-dichloro-4-trifluoromethylphenyl)-2-chloro-4-chlorodifluoromethylsulfinylimidazole;
1-(2,6-dichloro-4-trifluoromethylphenyl)-2-chloro-4-chlorodifluoromethylsulfonylimidazole;
1-(2,6-dichloro-4-trifluoromethylphenyl)-5-methylsulfonyl-4-dichlorofluoromethylsulfinylimidazole;
1-(2,6-dichloro-4-trifluoromethylphenyl)-5-methylsulfinyl-4-dichlorofluoromethylsulfinylimidazole;
1-(6-chloro-2-methylsulfenyl-4-trifluoromethylphenyl)-2-chloro-4-dichlorofluoromethylsulfenylimidazole;
1-(6-chloro-2-methylsulfenyl-4-trifluoromethylphenyl)-2-chloro-4-dichlorofluoromethylsulfinylimidazole;
1-(2,6-dichloro-4-trifluoromethylphenyl)-2-chloro-5-methylsulfenyl-4-trifluoromethylsulfenylimidazole;
1-(2,6-dichloro-4-trifluoromethylphenyl)-5-bromo-4-trifluoromethylsulfenylimidazole;
1-(2,6-dichloro-4-trifluoromethylphenyl)-2-methyl-4-chlorodifluoromethylsulfenylimidazole;
1-(2,6-dichloro-4-trifluoromethylphenyl)-5-chloro-4-trifluoromethylsulfenylimidazole;
1-(2,6-dichloro-4-trifluoromethylphenyl)-2,5-dichloro-4-dichlorofluoromethylsulfenylimidazole;
1-(2,6-dichloro-4-trifluoromethylphenyl)-4-chlorodifluoromethylsulfenylimidazole;
1-(2-chloro-4-trifluoromethylphenyl)-4-dichlorofluoromethylsulfinylimidazole;
1-(2-chloro-4-trifluoromethylphenyl)-4-trifluoromethylsulfinylimidazole;
1-(2-chloro-4-trifluoromethylphenyl)-4-trifluoromethylsulfonylimidazole;
1-(2,6-dichloro-4-bromophenyl)-4-dichlorofluoromethylsulfenylimidazole;
1-(2,6-dichloro-4-bromophenyl)-4-dichlorofluoromethylsulfinylimidazole;
1-(2,6-dichloro-4-bromophenyl)-4-chlorodifluoromethylsulfenylimidazole;
1-(2,6-dichloro-4-trifluoromethoxyphenyl)-4-trifluoromethylsulfinylimidazole;
1-(2,6-dichloro-4-trifluoromethoxyphenyl)-4-chlorodifluoromethylsulfenylimidazole;
1-(2,6-dichloro-4-trifluoromethoxyphenyl)-4-chlorodifluoromethylsulfinylimidazole;
1-(2,6-dichloro-4-trifluoromethoxyphenyl)-4-dichlorofluoromethylsulfonylimidazole; or
1-(2,6-dichloro-4-trifluoromethoxyphenyl)-2-bromo-4-dichlorofluoromethylsulfenylimidazole.

15. The method of claim 12, wherein the compound of formula (IIa) is:
1-(2-bromo-6-chloro-4-trifluoromethoxyphenyl)-4-dichlorofluoromethylsulfinylimidazole;
1-(2,6-dichchloro-4-trifluoromethoxyphenyl)-2-methyl-4-dichlorofluoromethylsulfenylimidazole;
1-(2,6-dichloro-4-trifluoromethoxyphenyl)-2-methyl-4-dichlorofluoromethylsulfonylimidazole;
1-(2,6-dichloro-4-trifluoromethoxyphenyl)-2-methyl-4-dichlorofluoromethylsulfinylimidazole;
1-(2,6-dichloro-4-trifluoromethylphenyl)-2-cyano-4-dichlorofluoromethylsulfenylimidazole;
1-(2,6-dichloro-4-trifluoromethylphenyl)-5-bromo-2-methyl-4-dichlorofluoromethylsulfenylimidazole;
1-(2,6-dichloro-4-trifluoromethylphenyl)-5-bromo-2-methyl-4-dichlorofluoromethylsulfinylimidazole;
1-(2,4,6-trichlorophenyl)-2-methyl-4-dichlorofluoromethylsulfenylimidazole;
1-(2,4,6-trichlorophenyl)-2-methyl-4-dichlorofluoromethylsulfinylimidazole;
1-(2,4,6-trichlorophenyl)-5-chloro-4-dichlorofluoromethylsulfenylimidazole;
1-(2,4,6-trichlorophenyl)-5-bromo-4-dichlorofluoromethylsulfenylimidazole;
1-(2,4,6-trichlorophenyl)-5-bromo-4-dichlorofluoromethylsulfinylimidazole;
1-(2,4,6-trichlorophenyl)-5-bromo-4-chlorodifluoromethylsulfenylimidazole;
1-(2,4,6-trichlorophenyl)-5-bromo-4-chlorodifluoromethylsulfinylimidazole;
1-(2,4,6-trichlorophenyl)-5-chloro-4-chlorodifluoromethylsulfenylimidazole;
1-(2,4,6-trichlorophenyl)-5-chloro-4-chlorodifluoromethylsulfinylimidazole;
1-(2,4,6-trichlorophenyl)-5-chloro-4-dichlorofluoromethylsulfinylimidazole;
1-(2-bromo-4,6-dichlorophenyl)-4-dichlorofluoromethylsulfenylimidazole;
1-(2-bromo-4,6-dichlorophenyl)-5-bromo-4-dichlorofluoromethylsulfenylimidazole;
1-(2-bromo-4,6-dichlorophenyl)-5-bromo-4-trifluoromethylsulfenylimidazole;

1-(2-bromo-4,6-dichlorophenyl)-4-dichlorofluoromethylsulfinylimidazole;

1-(2,4,6-trichlorophenyl)-5-bromo-4-dichlorofluoromethylsulfonylimidazole;

1-(2-bromo-4,6-dichlorophenyl)-5-bromo-4-dichlorofluoromethylsulfinylimidazole;

1-(2-bromo-4,6-dichlorophenyl)-5-bromo-4-trifluoromethylsulfinylimidazole;

1-(2-bromo-4,6-dichlorophenyl)-5-bromo-4-dichlorofluoromethylsulfonylimidazole;

1-(2-bromo-4,6-dichlorophenyl)-5-bromo-4-trifluoromethylsulfonylimidazole;

1-(2,4,6-trichlorophenyl)-5-chloro-4-chlorofluoromethylsulfenylimidazole; or 1-(2,4,6-trichlorophenyl)-5-bromo-2-methyl-4-dichlorofluoromethylsulfinylimidazole.

16. A method for the control of: arthropods; nematodes; or helminth or protozoan pests at a locus which comprises treatment of the locus with an effective amount of a compound of formula (IIb), wherein the various substituents X, Y, Z, $R_2$, $R_3$, $R_4$, $R_5$ and $R_6$ are as defined in claim 8.

17. The method of claim 16, wherein the compound of formula (IIb) is:

1-(2,6-dichloro-4-fluorophenyl)-5-methylsulfenyl-4-dichlorofluoromethylsulfenylimidazole;

1-(2,4,6-trichlorophenyl)-5-methylsulfenyl-4-dichlorofluoromethylsulfenylimidazole;

1-(2,6-dichloro-4-fluorophenyl)-5-bromo-4-dichlorofluoromethylsulfenylimidazole;

1-(2,6-dichloro-4-fluorophenyl)-5-methylsulfenyl-4-dichlorofluoromethylsulfenylimidazole;

1-(2,6-dichloro-4-fluorophenyl)-5-bromo-4-trifluoromethylsulfenylimidazole;

1-(2,6-dichloro-4-fluorophenyl)-5-chloro-4-dichlorofluoromethylsulfenylimidazole;

1-(2,6-dichloro-4-fluorophenyl)-5-bromo-4-chlorodifluoromethylsulfenylimidazole;

1-(2,4,6-trichlorophenyl)-5-ethoxymethylideneimino-4-dichlorofluoromethylsulfenylimidazole;

1-(2-bromo-4,6-dichlorophenyl)-5-methylsulfenyl-4-dichlorofluoromethylsulfenylimidazole;

1-(2-bromo-4,6-dichlorophenyl)-5-methylsulfenyl-4-trifluoromethylsulfenylimidazole;

1-(2,6-dibromo-4-fluorophenyl)-5-bromo-4-chlorodifluoromethylsulfenylimidazole;

1-(2,6-dichloro-4-fluorophenyl)-5-bromo-4-trifluoromethylsulfonylimidazole;

1-(2,6-dichloro-4-trifluoromethylphenyl)-2-methyl-5-methylsulfenyl-4-dichlorofluoromethylsulfenylimidazole;

1-(2,6-dichloro-4-fluorophenyl)-5-bromo-4-dichlorofluoromethylsulfinylimidazole;

1-(2,6-dichloro-4-fluorophenyl)-5-bromo-4-dichlorofluoromethylsulfonylimidazole;

1-(4-bromo-2,6-dichlorophenyl)-5-methylsulfenyl-4-dichlorofluoromethylsulfenylimidazole; or 1-(2,4,6-trichlorophenyl)-5-methylsulfenyl-4-chlorodifluoromethylsulfenylimidazole.

18. The method of claim 11, wherein the locus comprises agricultural or horticultural plants or a medium in which the plants grow and the pests are arthropod or nematode pests of the plants, and the treatment is by applying to the plants or to the medium in which they grow an effective amount of the compound of formula (I).

19. The method of claim of 18, wherein the compound is applied to the locus, in which the arthropod or nematode pests are controlled, at a rate of about 0.005 kg to about 15 kg of compound per hectare of locus treated.

20. The method of claim 19, wherein the compound is applied to the locus at a rate of about 0.02 kg to about 2 kg of compound per hectare.

21. The method of claim 18, wherein said pests are mites, aphids, insects or plant nematodes or combinations thereof, which comprises incorporating the compound into soil in which the plants are planted or are to be planted, or applying the compound to the plant's seeds, to the plant's roots, to the plant's foliage.

22. The method of claim 21, wherein: said insects are soil insects in the Coleoptera order, Lepidoptera order or Diptera order; said mites are in the subclass Acari; and said aphids are in the super family Aphidoidea.

23. The method of claim 11, wherein said method is employed in the field of veterinary medicine or livestock husbandry or in the maintenance of public health against arthropods, helminths or protozoa which are parasitic internally or externally upon warm-blooded vertebrates.

24. The method of claim 23, wherein said arthropods are insects in the Diptera order or mites in the subclass Acari or both.

25. A composition for the control of arthropod, nematode, helminth, or protozoan pests comprising; a compatible component and an effective amount of a compound of formula (I) as defined in claim 1.

26. The composition of claim 25, which contains 0.05 to 95% weight of one or more compounds of formula (I) as active ingredient and 1 to 95% by weight of one or more agronomically or medicinally acceptable solid or liquid carriers.

27. The composition of claim 26, further comprising 0.5 to 50% by weight of one or more compatible components, which are agronomically or medicinally acceptable diluents, adjuvants or surface active-agents.

28. A composition for the control of arthropod, nematode, helminth, or protozoan pests comprising a compatible component and an effective amount of a compound of formula (I) as defined in claim 2.

29. A composition for the control of arthropod, nematode, helminth, or protozoan pests comprising a compatible component and an effective amount of a compound of formula (I) as defined in claim 8.

30. The composition of claim 28, wherein the compound of formula (I) is:

1-(2,6-dichloro-4-trifluoromethylphenyl)-2-chloro-5-methylsulfenyl-4-chlorodifluoromethylsulfenylimidazole;

1-(2,6-dichloro-4-trifluoromethylphenyl)-2-chloro-4-trifluoromethylsulfinylimidazole;

1-(2,6-dichloro-4-trifluoromethylphenyl)-5-bromo-4-dichlorofluoromethylsulfenylimidazole;

1-(2,6-dichloro-4-trifluoromethylphenyl)-2-chloro-4-dichlorofluoromethylsulfenylimidazole;

1-(2,6-dichloro-4-trifluoromethylphenyl)-2-bromo-4-dichlorofluoromethylsulfenylimidazole;

1-(2,6-dichloro-4-trifluoromethylphenyl)-4-trifluoromethylsulfinylimidazole;

1-(2,6-dichloro-4-trifluoromethylphenyl)-2-chloro-4-dichlorofluoromethylsulfinylimidazole;

1-(2,6-dichloro-4-trifluoromethylphenyl)-2-chloro-4-dichlorofluoromethylsulfonylimidazole;

1-(2,6-dichloro-4-trifluoromethylphenyl)-2-bromo-4-chlorodifluoromethylsulfinylimidazole;

1-(2,6-dichloro-4-trifluoromethylphenyl)-2-bromo-4-chlorodifluoromethylsulfenylimidazole;
1-(2,6-dichloro-4-trifluoromethylphenyl)-2-chloro-4-chlorodifluoromethylsulfenylimidazole;
1-(6-chloro-2-methylsulfenyl-4-trifluoromethylphenyl)-2-bromo-4-chlorodifluoromethylsulfonylimidazole;
1-(6-chloro-2-methylsulfenyl-4-trifluoromethylphenyl)-2-chloro-4-dichlorofluoromethylsulfonylimidazole;
1-(2,6-dichloro-4-trifluoromethylphenyl)-4-dichlorofluoromethylsulfenylimidazole;
1-(2,6-dichloro-4-trifluoromethylphenyl)-4-dichlorofluoromethylsulfinylimidazole;
1-(2,6-dichloro-4-trifluoromethylphenyl)-4-dichlorofluoromethylsulfonylimidazole;
1-(2,6-dichloro-4-trifluoromethylphenyl)-2-methyl-4-dichlorofluoromethylsulfenylimidazole;
1-(2,6-dichloro-4-trifluoromethylphenyl)-2-methyl-4-dichlorofluoromethylsulfinylimidazole;
1-(2,6-dichloro-4-trifluoromethylphenyl)-2-methyl-4-dichlorofluoromethylsulfonylimidazole;
1-(2,4,6-trichlorophenyl)-4-dichlorofluoromethylsulfenylimidazole;
1-(2,4,6-trichlorophenyl)-4-dichlorofluoromethylsulfinylimidazole;
1-(2,6-dichloro-4-trifluoromethoxyphenyl)-4-dichlorofluoromethylsulfinylimidazole;
1-(2,6-dichloro-4-trifluoromethylphenyl)-4-chlorodifluoromethylsulfinylimidazole;
1-(2,6-dichloro-4-trifluoromethylphenyl)-2-methyl-4-chlorodifluoromethylsulfinylimidazole;
1-(2,6-dichloro-4-trifluoromethylphenyl)-2-methyl-4-chlorodifluoromethylsulfonylimidazole;
1-(2,4,6-trichlorophenyl)-4-chlorodifluoromethylsulfenylimidazole; or
1-(2,4,6-trichlorophenyl)-4-chlorodifluoromethylsulfinylimidzole.

31. The composition of claim 28, wherein the compound of formula (I) is:
1-(2,6-dichloro-4-trifluoromethylphenyl)-2-chloro-4-trifluoromethylsulfonylimidazole;
1-(2,6-dichloro-4-trifluoromethylphenyl)-5-methylsulfenyl-4-dichlorofluoromethylsulfenylimidazole;
1-(2,6-dichloro-4-trifluoromethylphenyl)-4-trifluoromethylsulfonylimidazole;
1-(2,6-dichloro-4-trifluoromethylphenyl)-5-bromo-4-trifluoromethylsulfonylimidazole;
1-(2,6-dichloro-4-trifluoromethylphenyl)-2-bromo-4-dichlorofluoromethylsulfinylimidazole;
1-(2,6-dichloro-4-trifluoromethylphenyl)-5-bromo-4-dichlorofluoromethylsulfonylimidazole;
1-(2,6-dichloro-4-trifluoromethylphenyl)-2-bromo-4-dichlorofluoromethylsulfonylimidazole;
1-(2,6-dichloro-4-trifluoromethylphenyl)-2-bromo-4-chlorodifluoromethylsulfonylimidazole;
1-(2,6-dichloro-4-trifluoromethylphenyl)-2-chloro-4-chlorodifluoromethylsulfinylimidazole;
1-(2,6-dichloro-4-trifluoromethylphenyl)-2-chloro-4-chlorodifluoromethylsulfonylimidazole;
1-(2,6-dichloro-4-trifluoromethylphenyl)-5-methylsulfonyl-4-dichlorofluoromethylsulfinylimidazole;
1-(2,6-dichloro-4-trifluoromethylphenyl)-5-methylsulfinyl-4-dichlorofluoromethylsulfinylimidazole;
1-(6-chloro-2-methylsulfenyl-4-trifluoromethylphenyl)-2-chloro-4-dichlorofluoromethylsulfenylimidazole;
1-(6-chloro-2-methylsulfenyl-4-trifluoromethylphenyl)-2-chloro-4-dichlorofluoromethylsulfinylimidazole;
1-(2,6-dichloro-4-trifluoromethylphenyl)-2-chloro-5-methylsulfenyl-4-trifluoromethylsulfenylimidazole;
1-(2,6-dichloro-4-trifluoromethylphenyl)-5-bromo-4-trifluoromethylsulfenylimidazole;
1-(2,6-dichloro-4-trifluoromethylphenyl)-2-methyl-4-chlorodifluoromethylsulfenylimidazole;
1-(2,6-dichloro-4-trifluoromethylphenyl)-5-chloro-4-trifluoromethylsulfenylimidazole;
1-(2,6-dichloro-4-trifluoromethylphenyl)-2,5-dichloro-4-dichlorofluoromethylsulfenylimidazole;
1-(2,6-dichloro-4-trifluoromethylphenyl)-4-chlorodifluoromethylsulfenylimidazole;
1-(2-chloro-4-trifluoromethylphenyl)-4-dichlorofluoromethylsulfinylimidazole;
1-(2-chloro-4-trifluoromethylphenyl)-4-trifluoromethylsulfinylimidazole;
1-(2-chloro-4-trifluoromethylphenyl)-4-trifluoromethylsulfonylimidazole;
1-(2,6-dichloro-4-bromophenyl)-4-dichlorofluoromethylsulfenylimidazole;
1-(2,6-dichloro-4-bromophenyl)-4-dichlorofluoromethylsulfinylimidazole;
1-(2,6-dichloro-4-bromophenyl)-4-chlorodifluoromethylsulfenylimidazole;
1-(2,6-dichloro-4-trifluoromethoxyphenyl)-4-trifluoromethylsulfinylimidazole;
1-(2,6-dichloro-4-trifluoromethoxyphenyl)-4-chlorodifluoromethylsulfenylimidazole;
1-(2,6-dichloro-4-trifluoromethoxyphenyl)-4-chlorodifluoromethylsulfinylimidazole;
1-(2,6-dichloro-4-trifluoromethoxyphenyl)-4-dichlorofluoromethylsulfonylimidazole; or
1-(2,6-dichloro-4-trifluoromethoxyphenyl)-2-bromo-4-dichlorofluoromethylsulfenylimidazole.

32. The composition of claim 28, wherein the compound of formula (I) is:
1-(2-bromo-6-chloro-4-trifluoromethoxyphenyl)-4-dichlorofluoromethylsulfinylimidazole;
1-(2,6-dichchloro-4-trifluoromethoxyphenyl)-2-methyl-4-dichlorofluoromethylsulfenylimidazole;
1-(2,6-dichloro-4-trifluoromethoxyphenyl)-2-methyl-4-dichlorofluoromethylsulfonylimidazole;
1-(2,6-dichloro-4-trifluoromethoxyphenyl)-2-methyl-4-dichlorofluoromethylsulfinylimidazole;
1-(2,6-dichloro-4-trifluoromethylphenyl)-2-cyano-4-dichlorofluoromethylsulfenylimidazole;
1-(2,6-dichloro-4-trifluoromethylphenyl)-5-bromo-2-methyl-4-dichlorofluoromethylsulfenylimidazole;
1-(2,6-dichloro-4-trifluoromethylphenyl)-5-bromo-2-methyl-4-dichlorofluoromethylsulfinylimidazole;
1-(2,4,6-trichlorophenyl)-2-methyl-4-dichlorofluoromethylsulfenylimidazole;
1-(2,4,6-trichlorophenyl)-2-methyl-4-dichlorofluoromethylsulfinylimidazole;
1-(2,4,6-trichlorophenyl)-5-chloro-4-dichlorofluoromethylsulfenylimidazole;
1-(2,4,6-trichlorophenyl)-5-bromo-4-dichlorofluoromethylsulfenylimidazole;
1-(2,4,6-trichlorophenyl)-5-bromo-4-dichlorofluoromethylsulfinylimidazole;
1-(2,4,6-trichlorophenyl)-5-bromo-4-chlorodifluoromethylsulfenylimidazole;
1-(2,4,6-trichlorophenyl)-5-bromo-4-chlorodifluoromethylsulfinylimidazole;
1-(2,4,6-trichlorophenyl)-5-chloro-4-chlorodifluoromethylsulfenylimidazole;
1-(2,4,6-trichlorophenyl)-5-chloro-4-chlorodifluoromethylsulfinylimidazole;
1-(2,4,6-trichlorophenyl)-5-chloro-4-dichlorofluoromethylsulfinylimidazole;

1-(2-bromo-4,6-dichlorophenyl)-4-dichlorofluoromethylsulfenylimidazole;
1-(2-bromo-4,6-dichlorophenyl)-5-bromo-4-dichlorofluoromethylsulfenylimidazole;
1-(2-bromo-4,6-dichlorophenyl)-5-bromo-4-trifluoromethylsulfenylimidazole;
1-(2-bromo-4,6-dichlorophenyl)-4-dichlorofluoromethylsulfinylimidazole;
1-(2,4,6-trichlorophenyl)-5-bromo-4-dichlorofluoromethylsulfonylimidazole;
1-(2-bromo-4,6-dichlorophenyl)-5-bromo-4-dichlorofluoromethylsulfinylimidazole;
1-(2-bromo-4,6-dichlorophenyl)-5-bromo-4-trifluoromethylsulfinylimidazole;
1-(2-bromo-4,6-dichlorophenyl)-5-bromo-4-dichlorofluoromethylsulfonylimidazole;
1-(2-bromo-4,6-dichlorophenyl)-5-bromo-4-trifluoromethylsulfonylimidazole;
1-(2,4,6-trichlorophenyl)-5-chloro-4-chlorofluoromethylsulfenylimidazole; or
1-(2,4,6-trichlorophenyl)-5-bromo-2-methyl-4-dichlorofluoromethylsulfinylimidazole.

33. The composition of claim 29, wherein the compound of formula (I) is:
1-(2,6-dichloro-4-fluorophenyl)-5-methylsulfenyl-4-dichlorofluoromethylsulfenylimidazole;
1-(2,4,6-trichlorophenyl)-5-methylsulfenyl-4-dichlorofluoromethylsulfenylimidazole;
1-(2,6-dichloro-4-fluorophenyl)-5-bromo-4-dichlorofluoromethylsulfenylimidazole;
1-(2,6-dichloro-4-fluorophenyl)-5-methylsulfenyl-4-dichlorofluoromethylsulfinylimidazole;
1-(2,6-dichloro-4-fluorophenyl)-5-bromo-4-trifluoromethylsulfenylimidazole;
1-(2,6-dichloro-4-fluorophenyl)-5-chloro-4-dichlorofluoromethylsulfenylimidazole;
1-(2,6-dichloro-4-fluorophenyl)-5-bromo-4-chlorodifluoromethylsulfenylimidazole;
1-(2,4,6-trichlorophenyl)-5-ethoxymethylideneimino-4-dichlorofluoromethylsulfenylimidazole;
1-(2-bromo-4,6-dichlorophenyl)-5-methylsulfenyl-4-dichlorofluoromethylsulfenylimidazole;
1-(2-bromo-4,6-dichlorophenyl)-5-methylsulfenyl-4-trifluoromethylsulfenylimidazole;
1-(2,6-dibromo-4-fluorophenyl)-5-bromo-4-chlorodifluoromethylsulfenylimidazole;
1-(2,6-dichloro-4-fluorophenyl)-5-bromo-4-trifluoromethylsulfonylimidazole;
1-(2,6-dichloro-4-trifluoromethylphenyl)-2-methyl-5-methylsulfenyl-4-dichlorofluoromethylsulfenylimidazole;
1-(2,6-dichloro-4-fluorophenyl)-5-bromo-4-dichlorofluoromethylsulfinylimidazole;
1-(2,6-dichloro-4-fluorophenyl)-5-bromo-4-dichlorofluoromethylsulfonylimidazole;
1-(4-bromo-2,6-dichlorophenyl)-5-methylsulfenyl-4-dichlorofluoromethylsulfenylimidazole; or
1-(2,4,6-trichlorophenyl)-5-methylsulfenyl-4-chlorodifluoromethylsulfenylimidazole.

* * * * *